US012350006B2

(12) United States Patent
Van Tassel et al.

(10) Patent No.: US 12,350,006 B2
(45) Date of Patent: *Jul. 8, 2025

(54) SYSTEM AND METHOD FOR WIRELESS COMMUNICATION OF ANALYTE DATA

(71) Applicant: Dexcom, Inc., San Diego, CA (US)

(72) Inventors: Robert Patrick Van Tassel, Alpine, CA (US); Benjamin Elrod West, San Diego, CA (US); Mark S. Deraves, Carlsbad, CA (US); Vincent P. Crabtree, San Diego, CA (US); William A. Pender, Dania Beach, FL (US); Douglas William Burnette, San Diego, CA (US); John Francis Loughlin, San Diego, CA (US); Sean S. Nihalani, Cardiff, CA (US); James Stephen Amidei, Escondido, CA (US); Stephen Alan Reichert, San Diego, CA (US); Sebastian Bohm, San Diego, CA (US); Krishna Prashant Daita, San Diego, CA (US); Brian Christopher Smith, San Diego, CA (US); Michael A. Ploof, Del Mar, CA (US)

(73) Assignee: Dexcom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/935,051

(22) Filed: Sep. 23, 2022

(65) Prior Publication Data
US 2023/0051514 A1    Feb. 16, 2023

Related U.S. Application Data

(63) Continuation of application No. 16/882,259, filed on May 22, 2020, now Pat. No. 11,457,810, which is a
(Continued)

(51) Int. Cl.
*H04W 76/14* (2018.01)
*A61B 5/00* (2006.01)
(Continued)

(52) U.S. Cl.
CPC ............ *A61B 5/002* (2013.01); *A61B 5/0004* (2013.01); *A61B 5/14532* (2013.01);
(Continued)

(58) Field of Classification Search
CPC ..... H04L 63/101; H04L 67/141; H04L 69/18; H04W 4/38; H04W 12/33; H04W 48/10;
(Continued)

(56) References Cited

U.S. PATENT DOCUMENTS 6,001,067 A    12/1999  Shults et al.
6,424,847 B1   7/2002   Mastrototaro et al.
(Continued)

FOREIGN PATENT DOCUMENTS

CN    101601041 A    12/2009
CN    102613958 A    8/2012
(Continued)

OTHER PUBLICATIONS

International Preliminary Report on Patentability for Application No. PCT/US2020/034275, mailed Dec. 9, 2021, 19 pages.
(Continued)

*Primary Examiner* — Harun Chowdhury
(74) *Attorney, Agent, or Firm* — PATTERSON + SHERIDAN, LLP

(57) ABSTRACT

Systems, methods, apparatuses, and devices, for the wireless communication of analyte data are provided. In some embodiments, a method and calibration station for calibrating a continuous analyte sensor system is provided. Methods and testing systems for testing a continuous analyte sensor system is provided. Continuous analyte sensor systems,
(Continued)

display devices and peripheral devices configured for wireless communication of analyte, connection, alarm and/or alert data and associated methods are provided.

16 Claims, 41 Drawing Sheets

Related U.S. Application Data continuation of application No. 16/881,592, filed on May 22, 2020, now Pat. No. 11,471,052.

(60) Provisional application No. 62/853,957, filed on May 29, 2019.

(51) Int. Cl.
*A61B 5/145* (2006.01)
*H04L 9/40* (2022.01)
*H04L 67/141* (2022.01)
*H04W 48/10* (2009.01)
*H04W 76/10* (2018.01)
*H04W 84/18* (2009.01)

(52) U.S. Cl.
CPC ............ *A61B 5/746* (2013.01); *H04L 63/101* (2013.01); *H04L 67/141* (2013.01); *H04W 48/10* (2013.01); *H04W 76/10* (2018.02); *H04W 76/14* (2018.02); *A61B 5/14503* (2013.01); *A61B 2560/0223* (2013.01); *A61B 2562/08* (2013.01); *H04W 84/18* (2013.01)

(58) Field of Classification Search
CPC ..... H04W 76/10; H04W 76/14; H04W 76/25; H04W 84/18; H04W 88/04
USPC ................ 370/254, 328, 401; 455/41.1–41.2
See application file for complete search history.

(56) References Cited

U.S. PATENT DOCUMENTS

| | | | |
|---|---|---|---|
| 6,477,395 B2 | 11/2002 | Schulman et al. | |
| 6,484,046 B1 | 11/2002 | Say et al. | |
| 6,512,939 B1 | 1/2003 | Colvin et al. | |
| 6,565,509 B1 | 5/2003 | Say et al. | |
| 6,579,690 B1 | 6/2003 | Bonnecaze et al. | |
| 6,931,327 B2 | 8/2005 | Goode, Jr. et al. | |
| 7,310,544 B2 | 12/2007 | Brister et al. | |
| 2005/0027463 A1 | 2/2005 | Goode, Jr. et al. | |
| 2005/0043598 A1 | 2/2005 | Goode, Jr. et al. | |
| 2005/0154271 A1 | 7/2005 | Rasdal et al. | |
| 2005/0192557 A1 | 9/2005 | Brauker et al. | |
| 2005/0203360 A1 | 9/2005 | Brauker et al. | |
| 2006/0020187 A1 | 1/2006 | Brister et al. | |
| 2006/0222566 A1 | 10/2006 | Brauker et al. | |
| 2007/0016381 A1 | 1/2007 | Kamath et al. | |
| 2007/0027385 A1 | 2/2007 | Brister et al. | |
| 2007/0032706 A1 | 2/2007 | Kamath et al. | |
| 2007/0197890 A1 | 8/2007 | Boock et al. | |
| 2007/0203966 A1 | 8/2007 | Brauker et al. | |
| 2007/0208245 A1 | 9/2007 | Brauker et al. | |
| 2007/0208246 A1 | 9/2007 | Brauker et al. | |
| 2008/0033254 A1 | 2/2008 | Kamath et al. | |
| 2008/0108942 A1 | 5/2008 | Brister et al. | |
| 2008/0119703 A1 | 5/2008 | Brister et al. | |
| 2009/0240120 A1 | 9/2009 | Mensinger et al. | |
| 2012/0232520 A1 | 9/2012 | Sloan et al. | |
| 2012/0255875 A1 | 10/2012 | Vicente et al. | |
| 2013/0076531 A1 | 3/2013 | San Vicente et al. | |
| 2014/0002237 A1 | 1/2014 | Infante et al. | |
| 2014/0012511 A1 | 1/2014 | Mensinger et al. | |
| 2014/0169261 A1* | 6/2014 | Ming ................... H04W 88/04 370/315 |
| 2015/0123810 A1* | 5/2015 | Hernandez-Rosas ........ H04W 76/14 340/870.02 |
| 2016/0261974 A1 | 9/2016 | Arrizza | |
| 2016/0345879 A1 | 12/2016 | Brauker et al. | |
| 2017/0281060 A1* | 10/2017 | Wedekind ............... H04L 69/18 |
| 2017/0311116 A1 | 10/2017 | Aga et al. | |
| 2017/0325724 A1 | 11/2017 | Wang et al. | |
| 2018/0027104 A1 | 1/2018 | Mandapaka et al. | |
| 2018/0027106 A1 | 1/2018 | Mandapaka et al. | |
| 2018/0027412 A1* | 1/2018 | Mandapaka .......... H04W 76/25 713/151 |
| 2018/0110077 A1 | 4/2018 | Mandapaka et al. | |
| 2018/0172664 A1* | 6/2018 | Love ....................... H04W 4/38 |
| 2018/0182491 A1 | 6/2018 | Belliveau et al. | |
| 2019/0132801 A1 | 5/2019 | Kamath et al. | |
| 2020/0077891 A1 | 3/2020 | Chavan et al. | |
| 2020/0375455 A1 | 12/2020 | Van Tassel et al. | |
| 2020/0375457 A1 | 12/2020 | Van Tassel et al. | |

FOREIGN PATENT DOCUMENTS

| | | |
|---|---|---|
| CN | 104781820 A | 7/2015 |
| CN | 105706423 A | 6/2016 |
| CN | 107095680 A | 8/2017 |
| CN | 107567017 A | 1/2018 |
| CN | 107847140 A | 3/2018 |
| CN | 109219801 A | 1/2019 |
| CN | 109475331 A | 3/2019 |
| CN | 109716854 A | 5/2019 |
| JP | 2018514826 A | 6/2018 |
| JP | 2019537848 A | 12/2019 |
| WO | 2013090731 A1 | 6/2013 |
| WO | 2016053909 A1 | 4/2016 |
| WO | 2019035073 A2 | 2/2019 |

OTHER PUBLICATIONS

International Search Report and Written Opinion for Application No. PCT/US2020/034275, mailed Sep. 29, 2020, 7 pages.

* cited by examiner

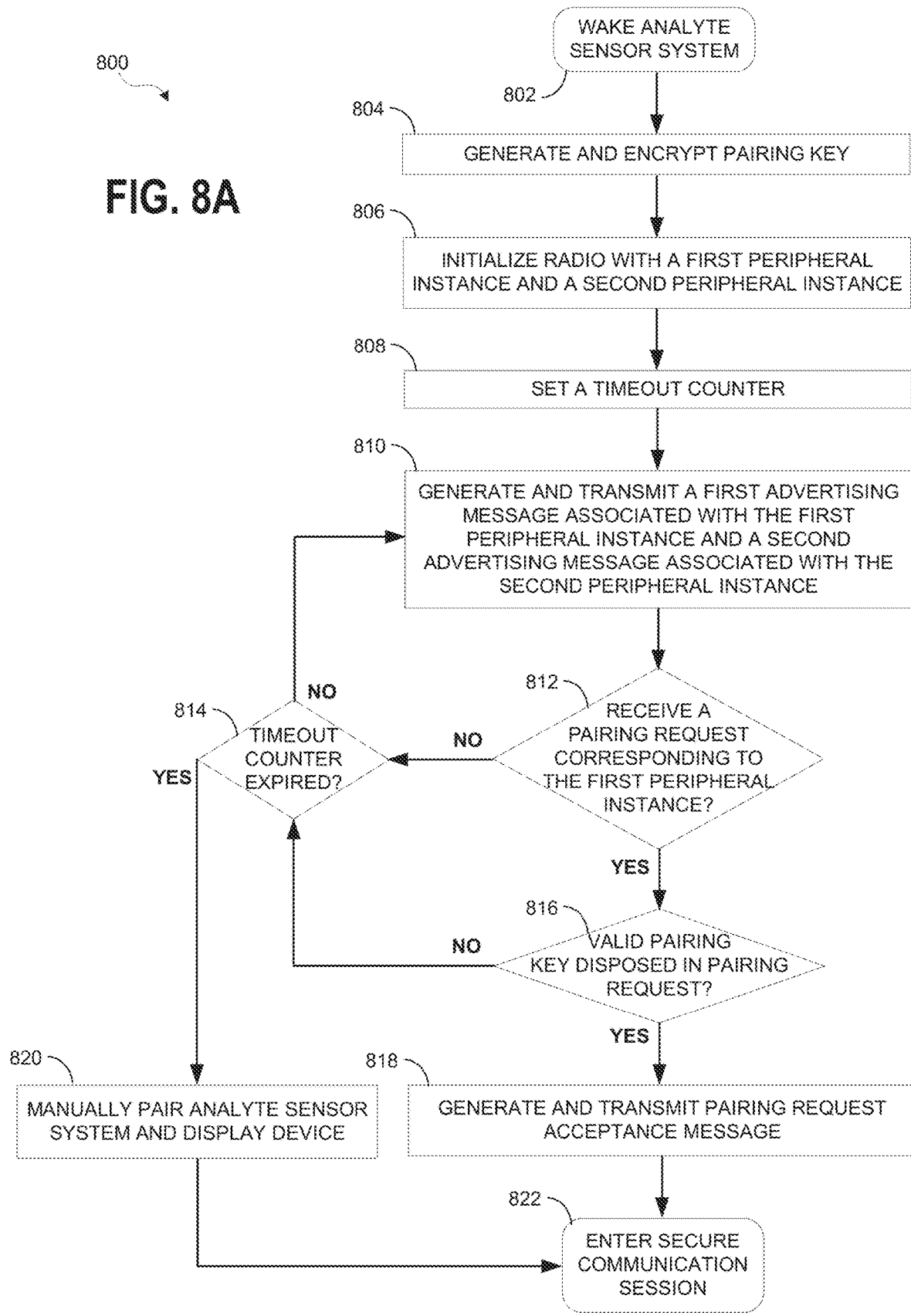

SYSTEM AND METHOD FOR WIRELESS COMMUNICATION OF ANALYTE DATA

CROSS-REFERENCE TO RELATED APPLICATIONS

This application is a continuation of U.S. patent application Ser. No. 16/882,259, filed May 22, 2020, which is a continuation of U.S. patent application Ser. No. 16/881,592, filed May 22, 2020, which claims the benefit of U.S. Provisional Application No. 62/853,957, filed May 29, 2019. The aforementioned applications are incorporated by reference herein in their entirety, and are hereby expressly made a part of this specification.

TECHNICAL FIELD

The present disclosure relates generally to continuous monitoring of analyte values received from an analyte sensor system. More particularly, the present disclosure is directed to systems, methods, apparatuses, and devices, for the wireless communication of analyte data.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) can be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically requires uncomfortable finger pricking methods. Due to the lack of comfort and convenience, a diabetic will normally only measure his or her glucose level two to four times per day. Unfortunately, these time intervals are spread so far apart that the diabetic will likely be alerted to a hyperglycemic or hypoglycemic condition too late, sometimes incurring dangerous side effects as a result. In fact, it is not only unlikely that a diabetic will take a timely SMBG value but will not know if his blood glucose value is going up (higher) or down (lower), due to limitations of conventional methods.

Consequently, a variety of non-invasive, transdermal (e.g., transcutaneous) and/or implantable electrochemical sensors are being developed for continuously detecting and/or quantifying blood glucose values. These devices generally transmit raw or minimally processed data for subsequent analysis at a remote device, which can include a display. The transmission to wireless display devices can be wireless.

With respect to the wireless transmission of glucose and other analyte data gathered using an implanted sensor, battery life of the transmitter acting in conjunction with the sensor is typically a concern. To conserve battery life or to increase the efficiency associated with the transmission of glucose and other analyte data, transmissions can, for example, need to be intermittent. The intermittent transmission of monitored data can introduce reliability issues, however. In some cases, reliability is thus sacrificed for battery life in conventional sensor systems.

SUMMARY

A method for calibrating a continuous analyte sensor system is provided. The method includes scanning an identification tag encoding information identifying the analyte sensor system. The method includes retrieving calibration data for a sensor of the analyte sensor system based at least in part on the information identifying the analyte sensor system. The method includes disposing the analyte sensor system sufficiently close to a calibration station for a short-range communication controller of the calibration station to induce a short-range antenna of the analyte sensor system to cause at least a portion of the analyte sensor system to transition to an operational mode. The method includes transferring at least the sensor calibration data from the calibration station to the continuous analyte sensor system via short-range communications responsive to a command, thereby facilitating calibration of the continuous analyte sensor system.

In some embodiments, the method includes causing the analyte sensor system to revert to a sleep mode after the sensor calibration data is stored in a storage of the analyte sensor system. In some embodiments, the identification tag is a 2-dimensional (2D) barcode encoding at least a lot number of an applicator and a serial number of the sensor of the analyte sensor system in a single string. In some embodiments, the sensor calibration data comprises an initial slope determined for the sensor, a final slope determined for the sensor, and an indication of a date on which the initial slope and the final slope was determined. In some embodiments, the command comprises an 0x7a near-field communication command configured to transmit each of a lot number of an applicator, a serial number of the sensor, the initial slope, the final slope and the indication of the date in a single message. In some embodiments, the sensor calibration data is retrieved form a database in which the sensor calibration data is indexed according to the lot number of the applicator and the serial number of the sensor.

A calibration station configured for calibrating a continuous analyte sensor system is provided. The calibration station includes an identification tag scanner configured to scan an identification tag encoding information identifying the analyte sensor system. The calibration station includes a processor configured to retrieve calibration data for a sensor of the analyte sensor system based at least in part on the information identifying the analyte sensor system. The calibration station includes a short-range communication controller configured to induce a short-range antenna of the analyte sensor system to cause at least a portion of the analyte sensor system to transition to an operational mode when the analyte sensor system is disposed sufficiently close to the calibration station, and transfer at least the sensor calibration data to the analyte sensor system via short-range communications responsive to a command, thereby facilitating calibration of the analyte sensor system.

In some embodiments, the short-range communication controller is further configured to send at least one signal to the analyte sensor system that causes the analyte sensor system to revert to a sleep mode after the sensor calibration data is stored in a storage of the analyte sensor system. In some embodiments, the identification tag is a 2-dimensional (2D) barcode encoding at least a lot number of an applicator and a serial number of the sensor of the analyte sensor system in a single string. In some embodiments, the sensor calibration data comprises an initial slope determined for the sensor, a final slope determined for the sensor, and an indication of a date on which the initial slope and the final slope was determined. In some embodiments, the command comprises an 0x7a NFC command configured to transmit each of a lot number of an applicator, a serial number of the sensor, the initial slope, the final slope and the indication of the date in a single message. In some embodiments, the sensor calibration data is retrieved from a database in which the sensor calibration data is indexed according to the lot number of the applicator and the serial number of the sensor.

A method for testing a continuous analyte sensor system is provided. The method includes waking at least a portion of an analyte sensor system from a sleep mode. The method include receiving, utilizing a first transceiver chip, a data packet transmitted from a second transceiver chip, the data packet comprising a request for the analyte sensor system to perform one or more tasks designed to verify anticipated operation of the analyte sensor system. The method includes processing the request. The method includes transmitting, utilizing the first transceiver chip, a response returning a result of the request to the second transceiver chip. The method includes receiving, utilizing the first transceiver chip, a message transmitted from the second transceiver chip, the message comprising instructions that cause one or more components of the analyte sensor system to revert to a sleep mode.

In some embodiments, the first transceiver chip is embedded in the analyte sensor system and the second transceiver chip is embedded in a factory testing station configured to test operation of the analyte sensor system. In some embodiments, each of the request, the response, and the message are communicated on a frequency channel that is pre-programmed into each of the first transceiver chip and the second transceiver chip. In some embodiments, the request, the response and the message are communicated without any prior connection or authentication processes occurring between the first transceiver chip and the second transceiver chip.

A method for testing a continuous analyte sensor system is provided. The method includes transmitting to a first transceiver chip, utilizing a second transceiver chip, a data packet comprising a request for the analyte sensor system to perform one or more tasks designed to verify anticipated operation of the analyte sensor system. The method includes receiving, utilizing the second transceiver chip, a response returning a result of the request from the first transceiver chip. The method includes transmitting, utilizing the second transceiver chip, a message to the first transceiver chip, the message comprising instructions that cause one or more components of the analyte sensor system to revert to a sleep mode.

In some embodiments, the first transceiver chip is embedded in the analyte sensor system and the second transceiver chip is embedded in a factory testing station configured to test operation of the analyte sensor system. In some embodiments, each of the request, the response, and the message are communicated on a frequency channel that is pre-programmed into each of the first transceiver chip and the second transceiver chip. In some embodiments, the request, the response and the message are communicated without any prior connection or authentication processes occurring between the first transceiver chip and the second transceiver chip.

A testing system for testing a continuous analyte sensor system is provided. The testing system includes the analyte sensor system comprising a first transceiver chip. The testing system includes a factory testing station comprising a second transceiver chip. The analyte sensor system is configured to wake at least a portion of the analyte sensor system from a sleep mode. The analyte sensor system is configured to receive, utilizing the first transceiver chip, a data packet transmitted from the second transceiver chip, the data packet comprising a request for the analyte sensor system to perform one or more tasks designed to verify anticipated operation of the analyte sensor system. The analyte sensor system is configured to process the request. The analyte sensor system is configured to transmit, utilizing the first transceiver chip, a response returning a result of the request to the second transceiver chip. The analyte sensor system is configured to receive, utilizing the first transceiver chip, a message transmitted from the second transceiver chip, the message comprising instructions that cause one or more components of the analyte sensor system to revert to a sleep mode. The factory testing station is configured to transmit the data packet to the first transceiver chip utilizing the second transceiver chip. The factory testing station is configured to receive the response from the first transceiver chip utilizing the second transceiver chip. The factory testing station is configured to transmit the message to the first transceiver chip utilizing the second transceiver chip.

In some embodiments, each of the first transceiver chip and the second transceiver chip are pre-programmed to communicate each of the request, the response, and the message on a pre-determined frequency channel. In some embodiments, the first transceiver chip and the second transceiver chip communicate the request, the response and the message without any prior connection or authentication processes.

A continuous analyte sensor system configured for wireless communication of analyte data is provided. The system includes a sensor comprising a plurality of terminals, the sensor configured to generate a current through the plurality of terminals based on an analyte concentration of a host. The system includes a shorting element configured to electrically short the plurality of terminals when the sensor is disposed in a packaging. The system includes a sensor electronics module configured to wake periodically, measure the current through the plurality of terminals, determine that the measured current is below a predetermined threshold; and generate a signal configured to wake at least one additional component of the analyte sensor system based on the determination.

In some embodiments, the shorting element comprises at least one of an electrically conductive wire, an electrically conductive sheet, or an electrically conductive foam comprising at least a portion of the packaging.

A method for wireless communication of continuous analyte data is provided. The method includes generating a pairing key. The method includes initializing a transceiver radio with a first peripheral instance and a second peripheral instance. The method includes generating and transmitting a first advertisement message associated with the first peripheral instance. The method includes generating and transmitting a second advertisement message associated with the second peripheral instance and comprising the pairing key. The method includes determining that a pairing request corresponding to the first peripheral instance has been received. The method includes determining that the pairing request comprises the pairing key. The method includes generating and transmitting a pairing request acceptance message based on the pairing request comprising the pairing key.

In some embodiments, the method includes encrypting the pairing key, wherein the second advertisement message comprises the encrypted pairing key and the pairing request comprises a decrypted version of the encrypted pairing key. In some embodiments, the first advertisement message comprises one or more of an indication of a manufacturer of an analyte sensor system, an address identifying the analyte sensor system, an indication that the first peripheral instance is connectable, and an indication of out-of-band authentication. In some embodiments, the second advertisement message comprises one or more of an indication of the manufacturer of the analyte sensor system, the address identifying the analyte sensor system, an indication that the second peripheral instance is not connectable, and a payload comprising the pairing key. In some embodiments, the first peripheral instance and the second peripheral instance are both associated with a same analyte sensor system. In some embodiments, the first advertisement message and the second advertisement message are transmitted during a same pairing session.

A continuous analyte sensor system is provided. The system includes an analyte sensor. The system includes a transceiver radio. The system includes one or more processors configured to generate a pairing key. The one or more processors are configured to initialize the transceiver radio with a first peripheral instance and a second peripheral instance. The one or more processors are configured to generate and transmit, via the transceiver radio, a first advertisement message associated with the first peripheral instance. The one or more processors are configured to generate and transmit, via the transceiver radio, a second advertisement message associated with the second peripheral instance and comprising the pairing key. The one or more processors are configured to determine that a pairing request corresponding to the first peripheral instance has been received via the transceiver radio. The one or more processors are configured to determine that the pairing request comprises the pairing key. The one or more processors are configured to generate and transmit, via the transceiver radio, a pairing request acceptance message based on the pairing request comprising the pairing key.

A method for wireless communication of continuous analyte data is provided. The method includes monitoring one or more communication channels for one or more advertising messages indicative of an analyte sensor system initiating a pairing operation with a peripheral device. The method includes determining that a first advertisement message has been received from the analyte sensor system, the first advertisement message comprising an indication of a predetermined manufacturer of the analyte sensor system and an address identifying the analyte sensor system. The method includes determining that a second advertisement message comprising the indication of the predetermined manufacturer, the address identifying the analyte sensor system, and a pairing key has been received from the analyte sensor system. The method includes extracting the pairing key from the second advertisement message. The method includes generating and transmitting a pairing request message comprising the extracted pairing key. The method includes receiving a pairing request acceptance message based on the pairing request message.

In some embodiments, the pairing key within the second advertisement message is encrypted and the pairing request comprises a decrypted version of the encrypted pairing key, the method including decrypting the pairing key to obtain the decrypted version of the encrypted pairing key. In some embodiments, the first advertisement message further comprises one or more of an indication that a first peripheral instance of the analyte sensor system is connectable, and an indication of out-of-band authentication. In some embodiments, the second advertisement message further comprises an indication that a second peripheral instance of the analyte sensor system is not connectable, the pairing key being disposed in a payload of the second advertisement message. In some embodiments, the first advertisement message and the second advertisement message are received during a same pairing session.

A peripheral device is provided. The device includes a display, a transceiver radio, and one or more processors configured to monitor one or more communication channels for one or more advertising messages indicative of an analyte sensor system initiating a pairing operation with the peripheral device. The one or more processors are configured to determine that a first advertisement message has been received from the analyte sensor system, the first advertisement message comprising an indication of a predetermined manufacturer of the analyte sensor system and an address identifying the analyte sensor system. The one or more processors are configured to determine that a second advertisement message comprising the indication of the predetermined manufacturer, the address identifying the analyte sensor system, and a pairing key has been received from the analyte sensor system. The one or more processors are configured to extract the pairing key from the second advertisement message. The one or more processors are configured to generate and transmit, via the transceiver radio, a pairing request message comprising the extracted pairing key. The one or more processors are configured to receive, via the transceiver radio, a pairing request acceptance message based on the pairing request message.

A method for wireless communication of continuous analyte data is provided. The method includes transmitting an advertisement message for establishing a communication channel. The method includes receiving a random number encrypted utilizing a first public key over the communication channel. The method includes decrypting the encrypted random number utilizing a first private key associated with the first public key. The method includes re-encrypting the decrypted random number utilizing a second public key. The method includes transmitting the re-encrypted random number over the communication channel. The method includes transmitting sensor data encrypted utilizing the second public key.

In some embodiments, the first private key is one of a first plurality of unique private keys configured to decrypt data previously encrypted utilizing the first public key and the second private key is one of a second plurality of unique private keys configured to decrypt data previously encrypted utilizing the second public key. In some embodiments, the first public key and the second public key are publicly available keys, and the first private key and the second private key are not publicly available keys. In some embodiments, the method includes receiving at least one of the first private key and the second public key from a server.

A continuous analyte sensor system is provided. The system includes an analyte sensor, a transceiver radio, and one or more processors configured to cause an advertisement message for establishing a communication channel to be transmitted. The one or more processors are configured to receive a random number encrypted utilizing a first public key over the communication channel. The one or more processors are configured to decrypt the encrypted random number utilizing a first private key associated with the first public key. The one or more processors are configured to re-encrypt the random number utilizing a second public key. The one or more processors are configured to cause the re-encrypted random number to be transmitted over the communication channel. The one or more processors are configured to cause sensor data encrypted utilizing the second public key to be transmitted.

A method for wireless communication of continuous analyte data is provided. The method includes receiving an advertisement message for establishing a communication channel. The method includes generating a random number. The method includes encrypting the random number utilizing a first public key. The method includes transmitting the encrypted random number utilizing the communication channel. The method includes receiving the random number re-encrypted utilizing a second public key. The method includes decrypting the re-encrypted random number utilizing a second private key. The method includes comparing the decrypted random number to the random number originally generated. The method includes authenticating a communication session based on a determination that the decrypted random number and the random number originally generated are the same. The method includes receiving sensor data encrypted utilizing the second public key.

In some embodiments, the first private key is one of a first plurality of unique private keys configured to decrypt data previously encrypted utilizing the first public key and the second private key is one of a second plurality of unique private keys configured to decrypt data previously encrypted utilizing the second public key. In some embodiments, the first public key and the second public key are publicly available keys, and the first private key and the second private key are not publicly available keys.

A peripheral device is provided. The device includes a display, a transceiver radio; and one or more processors configured to receive an advertisement message for establishing a communication channel. The one or more processors are configured to generate a random number. The one or more processors are configured to encrypt the random number utilizing a first public key. The one or more processors are configured to transmit the encrypted random number utilizing the communication channel. The one or more processors are configured to receive the random number re-encrypted utilizing a second public key. The one or more processors are configured to decrypt the re-encrypted random number utilizing a second private key. The one or more processors are configured to compare the decrypted random number to the random number originally generated. The one or more processors are configured to authenticate a communication session based on a determination that the decrypted random number and the random number originally generated are the same. The one or more processors are configured to receive sensor data encrypted utilizing the second public key.

A method for wireless communication of continuous analyte data is provided. The method includes successively coupling each of a plurality of filtering circuits to an antenna, each of the filtering circuits configured to pass a respective signal received by the antenna in a respective frequency channel. The method includes measuring a respective amount of power received on each respective frequency channel while the analyte sensor system is not wirelessly communicating. The method includes comparing the measured respective amounts of power received on each respective frequency channel. The method includes selecting the respective frequency channel having the lowest measured amount of power for the antenna to transmit one or more signals.

In some embodiments, each of the plurality of filtering circuits comprises a bandpass filter. In some embodiments, successively coupling each of the plurality of filtering circuits to the antenna comprises successively closing a respective switch coupling a respective one of the filtering circuits to the antenna. In some embodiments, selecting the respective frequency channel having the lowest measured amount of power for the antenna to transmit one or more signals comprises sending at least one signal causing a frequency selection circuit of a transmitter to select the respective frequency channel.

A continuous analyte sensor system is provided. The system includes an antenna and a plurality of filtering circuits couplable to the antenna, each of the filtering circuits configured to pass a respective signal received by the antenna in a respective frequency channel. The system includes one or more processors configured to successively couple each of the plurality of filtering circuits to the antenna. The one or more processors are configured to measure a respective amount of power received on each respective frequency channel while the analyte sensor system is not wirelessly communicating. The one or more processors are configured to compare the measured respective amounts of power received on each respective frequency channel. The one or more processors are configured to select the respective frequency channel having the lowest measured amount of power for the antenna to transmit one or more signals.

A method for wireless communication of analyte data by a continuous analyte sensor system is provided. The method includes preconfiguring the analyte sensor system to periodically wake from a low-power passive monitoring mode according to a predetermined interval for waking the analyte sensor system. The method includes receiving a wake signal from a display device before expiration of the predetermined interval while the analyte sensor system is in the low-power passive monitoring mode, thereby causing the analyte sensor system to wake before expiration of the predetermined interval. The method includes transmitting an advertisement message in response to the wake signal. The method includes receiving a pairing request from the display device. The method includes transmitting a pairing request acceptance message to the display device. The method includes transmitting sensor data to the display device.

In some embodiments, the transmitting sensor data to the display device occurs at a time before the predetermined interval for waking the analyte sensor system has expired. In some embodiments, the wake signal has a predetermined pattern, magnitude or modulation configured to cause the analyte sensor system to wake from the low-power passive monitoring mode.

A continuous analyte sensor system is provided. The system includes an analyte sensor and a transceiver radio. The system includes one or more processors configured to preconfigure the analyte sensor system to periodically wake from a low-power passive monitoring mode according to a predetermined interval for waking the analyte sensor system. The one or more processors are configured to receive a wake signal from a display device before expiration of the predetermined interval while the analyte sensor system is in a low-power passive monitoring mode, thereby causing the analyte sensor system to wake before expiration of the predetermined interval. The one or more processors are configured to cause an advertisement message to be transmitted in response to the wake signal. The one or more processors are configured to receive a pairing request from the display device. The one or more processors are configured to cause a pairing request acceptance message to be transmitted to the display device and cause transmission of sensor data to the display device.

A method for wireless communication of continuous analyte data by a display device is provided. The method includes transmitting a wake signal to an analyte sensor system that is in a low-power passive monitoring mode. The method includes receiving an advertisement message responsive to the wake signal. The method includes transmitting a pairing request to the analyte sensor system. The method includes receiving a pairing request acceptance message responsive to the pairing request. The method includes receiving sensor data from the analyte sensor system.

In some embodiments, the receiving sensor data from the analyte sensor system occurs at a time before a predetermined interval for waking the analyte sensor system has expired. In some embodiments, the wake signal has a predetermined pattern, magnitude or modulation configured to cause the analyte sensor system to wake from the low-power passive monitoring mode.

A display device is provided. The device includes a display and a transceiver radio. The device includes one or more processors configured to cause a wake signal to be transmitted to an analyte sensor system that is in a low-power passive monitoring mode. The one or more processors are configured to receiving an advertisement message responsive to the wake signal. The one or more processors are configured to causing a pairing request to be transmitted to the analyte sensor system. The one or more processors are configured to receiving a pairing request acceptance message responsive to the pairing request. The one or more processors are configured to receiving sensor data from the analyte sensor system.

A method for wireless communication of continuous analyte data is provided. The method includes physically moving a short-range wireless communication protocol-enabled display device sufficiently close to a sticker physically disposed on one of an analyte sensor system or a packaging for the analyte sensor system, comprising a short-range wireless communications tag having pre-programmed thereon a pairing key, such that the display device is able to retrieve the pairing key from the tag via the short-range wireless communication protocol. The method includes pairing the display device with the analyte sensor system for a wireless protocol different from the short-range wireless communication protocol utilizing the retrieved pairing key.

In some embodiments, the pairing key is associated with the analyte sensor system. In some embodiments, the physically moving the NFC-enabled display device sufficiently close to the sticker comprises tapping the display device on the sticker.

A display device is provided. The device includes a display, a short-range wireless communication protocol-enabled radio and a radio enabled for wireless communication utilizing a wireless protocol different from the short-range wireless communication protocol. The device includes one or more processors configured to retrieve, utilizing the short-range wireless communication protocol-enabled radio, a pairing key from a short-range wireless communications tag embedded in a sticker based on the display device being physically moved sufficiently close to the sticker, the tag being pre-programmed with the pairing key and the pairing key being associated with an analyte sensor system. The one or more processors are configured to perform a pairing operation with the analyte sensor system for the wireless communication protocol different from the short-range wireless communication protocol utilizing the retrieved pairing key.

In some embodiments, the display device being physically moved sufficiently close to the sticker comprises tapping the display device on the sticker.

A method for wireless communication of continuous analyte data is provided. The method includes detecting an advertisement message from an analyte sensor system. The method includes attempting to establish a connection with the analyte sensor system responsive to the advertisement message. The method includes determining that the attempt to establish the connection with the analyte sensor system has failed. The method includes generating an alert indicating that the analyte sensor system has been detected but an attempt to establish the connection with the analyte sensor system has failed.

In some embodiments, the alert comprises at least one suggested user intervention for improving the probability of establishing the connection with the analyte sensor system on a subsequent connection attempt.

A display device is provided. The device includes a display and a transceiver radio. The device includes one or more processors configured to detect an advertisement message from an analyte sensor system. The one or more processors are configured to attempt to establish a connection with the analyte sensor system responsive to the advertisement message. The one or more processors are configured to determine that the attempt to establish the connection with the analyte sensor system has failed. The one or more processors are configured to generate an alert indicating that the analyte sensor system has been detected but an attempt to establish the connection with the analyte sensor system has failed.

A method for wireless communication of continuous analyte data is provided. The method includes transmitting a wake signal to an analyte sensor system. The method includes receiving a transmitter ID corresponding to the analyte sensor system. The method includes comparing the received transmitter ID to a range of transmitter IDs corresponding to currently deployed analyte sensor systems. The method includes establishing a wireless connection with the analyte sensor system based on a determination that the received transmitter ID is within the range of transmitter IDs corresponding to analyte sensor systems currently deployed. The method includes receiving at least logged analyte concentration data from the analyte sensor system. The method includes generating one or more reports based on at least the logged analyte concentration data from the analyte sensor system.

In some embodiments, the wake signal is transmitted utilizing an electromagnet.

A device is provided, including a transceiver radio and an electromagnet. The device includes one or more processors configured to cause the electromagnet to transmit a wake signal to an analyte sensor system. The one or more processors are configured to receive a transmitter ID corresponding to the analyte sensor system. The one or more processors are configured to compare the received transmitter ID to a range of transmitter IDs corresponding to currently deployed analyte sensor systems. The one or more processors are configured to establish a wireless connection with the analyte sensor system based on a determination that the received transmitter ID is within the range of transmitter IDs corresponding to currently deployed analyte sensor systems. The one or more processors are configured to receive at least analyte concentration data logged by the analyte sensor system during a prior sensor session. The one or more processors are configured to generate one or more reports based on at least the logged analyte concentration data.

A method for wireless communication of continuous analyte data is provided. The method includes receiving a wake signal from a heath care provider device. The method includes transmitting a transmitter ID corresponding to an analyte sensor system. The method includes establishing a wireless connection with the health care provider device based on the transmitted transmitter ID being within a range of transmitter IDs corresponding to currently deployed analyte sensor systems. The method includes transmitting at least logged analyte concentration data to the health care provider device.

In some embodiments, the method includes generating analyte concentration data during a sensor session. In some embodiments, the method includes logging the analyte concentration data during the sensor session. In some embodiments, the wake signal is received by a magnetic sensor at a time after the sensor session has concluded.

A continuous analyte sensor system is provided. The system includes an analyte sensor configured to generate analyte concentration data during a sensor session. The system includes a storage configured to log the analyte concentration data during the sensor session. The system includes a magnetic sensor configured to receive a wake signal from a heath care provider device. The system includes a transceiver radio. The system includes one or more processors configured to cause the transceiver radio to transmit a transmitter ID corresponding to the analyte sensor system. The one or more processors are configured to establish a wireless connection with the health care provider device based on the transmitted transmitter ID being within a range of transmitter IDs corresponding to currently deployed analyte sensor systems. The one or more processors are configured to cause the transceiver radio to transmit at least the logged analyte concentration data to the health care provider device.

In some embodiments, the magnetic sensor receives the wake signal at a time after the sensor session has concluded.

A method for wireless communication of continuous analyte data is provided. The method includes periodically collecting raw data from an analyte sensor for a duration of a sensor session. The method includes storing the raw data. The method includes delaying conversion of the raw data to estimated analyte values until at least after the sensor session has concluded.

In some embodiments, the sensor session corresponds to an intended usable life of the analyte sensor system.

A continuous analyte sensor system is provided. The system includes an analyte sensor configured to periodically generate raw data for a duration of a sensor session. The system includes a storage configured to store the raw data during the sensor session. The system includes one or more processors configured to delay conversion of the raw data to estimated analyte values until at least after the sensor session has concluded.

A method for wireless communication of continuous analyte data is provided. The method includes measuring at least one analyte concentration value by an analyte sensor system during a sensor session. The method includes transmitting the at least one analyte concentration value to a device associated with a health care provider utilizing a cellular network connection.

In some embodiments, the at least one analyte concentration value is not displayed to a user of the analyte sensor system. In some embodiments, the at least one analyte concentration value is transmitted to the device associated with the health care provider after the sensor session has concluded.

A continuous analyte sensor system is provided. The system includes an analyte sensor configured to measure at least one analyte concentration value during a sensor session. The system includes a cellular network enabled transceiver radio. The system includes one or more processors configured to cause the cellular-network enabled transceiver radio to transmit the at least one analyte concentration value to a device associated with a health care provider utilizing a cellular network connection.

A method for wireless communication of data is provided. The method includes receiving, by an analyte sensor system, power via a near field communication from a first device. The method includes powering up at least a portion of an analyte sensor system utilizing the received power. The method includes transmitting data from the analyte sensor system to the first device, utilizing a first communication protocol, for use in troubleshooting a suspected malfunction of the analyte sensor system.

In some embodiments, the first communication protocol comprises a Bluetooth low energy protocol.

A continuous analyte sensor system is provided. The system includes a near field communication circuit configured to receive power, via a near field communication, from a first device. The system includes a transceiver radio configured to be powered up by the received power. The system includes one or more processors configured to cause the transceiver radio to transmit data to the first device, utilizing a first communication protocol, for use in troubleshooting a suspected malfunction of the analyte sensor system.

A method for wireless communication of continuous analyte data is provided. The method includes disposing a display device sufficiently close to an analyte sensor system for a short-term wireless communication protocol controller of the display device to transmit power, utilizing the short-term wireless communication protocol, to the analyte sensory system, thereby powering up at least a portion of the analyte sensor system. The method includes receiving data from the analyte sensor system via a first communication protocol. The method includes re-transmitting the data to a second device accessible to a customer service representative, via a second communication protocol, for troubleshooting a suspected malfunction of the analyte sensor system.

In some embodiments, the first communication protocol comprises a Bluetooth low energy protocol. In some embodiments, the second communication protocol is Wi-Fi.

A display device is provided. The device includes a short-term communication protocol controller configured to transmit power, utilizing the short-term communication protocol, to an analyte sensory system when the display device is disposed sufficiently close to the analyte sensor system, thereby powering up at least a portion of the analyte sensor system. The device includes a transceiver radio configured to receive data from the analyte sensor system via a first communication protocol. The device includes one or more processors configured to cause the transceiver radio to re-transmit the data to a second device accessible to a customer service representative, via a second communication protocol, for troubleshooting a suspected malfunction of the analyte sensor system.

A method for wireless communication of continuous analyte concentration data is provided. The method includes transmitting at least one of a wakeup signal and a first security code, as modulated visible light, to an analyte sensor system. The method includes receiving a second security code encrypted utilizing the first security code from the analyte sensor system. The method includes verifying the encrypted second security code. The method includes establishing a secure communication channel with the analyte sensor system responsive to the verifying. The method includes receiving analyte concentration data from the analyte sensor system over the secure communication channel.

In some embodiments, the encrypted second security code is received utilizing a communication protocol different from the modulated visible light. In some embodiments, the communication protocol is a Bluetooth Low Energy protocol. In some embodiments, the analyte concentration data is received encrypted utilizing the second security code and wherein the secure communication channel comprises a Bluetooth Low Energy communication channel. In some embodiments, the wakeup signal and the first security code are transmitted as modulated visible light utilizing a display. In some embodiments, the modulated visible light comprises one or more patterns of color, brightness or contrast displayed on the display.

A display device is provided. The device includes a display configured to transmit at least one of a wakeup signal and a first security code, as modulated visible light, to an analyte sensor system. The device includes a transceiver radio configured to receiving a second security code encrypted utilizing the first security code from the analyte sensor system. The device includes one or more processors configured to verify the encrypted second security code. The one or more processors are configured to establish a secure communication channel with the analyte sensor system responsive to the verifying. The one or more processors are configured to receive analyte concentration data from the analyte sensor system over the secure communication channel.

A method for wireless communication of continuous analyte concentration data is provided. The method includes receiving at least one of a wakeup signal and a first security code, as modulated visible light, from a display device. The method includes transmitting a second security code encrypted utilizing the first security code from an analyte sensor system. The method includes establishing a secure communication channel with the display device. The method includes transmitting analyte concentration data over the secure communication channel.

In some embodiments, the encrypted second security code is transmitted utilizing a communication protocol different from the modulated visible light. In some embodiments, the communication protocol is a Bluetooth Low Energy protocol. In some embodiments, the analyte concentration data is transmitted encrypted utilizing the second security code and wherein the secure communication channel comprises a Bluetooth Low Energy communication channel. In some embodiments, the wakeup signal and the first security code are received as modulated visible light utilizing a light sensor. In some embodiments, the modulated visible light comprises one or more patterns of color, brightness or contrast displayed on a display of the display device.

A continuous analyte sensor system is provided. The system includes a light sensor configured to receive at least one of a wakeup signal and a first security code, as modulated visible light, from a display device. The system includes a transceiver radio configured to transmit a second security code encrypted utilizing the first security code. The system includes one or more processors configured to establish a secure communication channel with the analyte sensor system. The one or more processors are configured to cause the transceiver radio to transmit analyte concentration data over the secure communication channel.

A method for wireless communication with a continuous analyte sensor system is provided. The method includes receiving from a user, on a first display device, an input indicative of a request to pair a second display device to the analyte sensor system. The method includes transmitting a first signal to the analyte sensory system indicating that the second display device has requested pairing. The method includes receiving a second signal from the second display device indicating the user has initiated a pairing process between the second display device and the analyte sensor system. The method includes, responsive to receiving the second signal from the second display device, transmitting a transmitter ID corresponding to the analyte sensor system to the second display device.

In some embodiments, the first display device comprises a smartphone, and the second display device comprises a smartwatch. In some embodiments, the second display device is configured to utilize the transmitter ID to pair with the analyte sensor system.

A first display device is provided. The device includes an input interface configured to receive from a user an input indicative of a request to pair a second display device to an analyte sensor system. The device includes a transceiver radio configured to transmit a first signal to the analyte sensory system indicating that the second display device has requested pairing. The device includes one or more processors configured to receive a second signal from the second display device indicating the user has initiated a pairing process between the second display device and the analyte sensor system. The one or more processors are configured to responsive to receiving the second signal from the second display device, cause the transceiver radio to transmit a transmitter ID corresponding to the analyte sensor system to the second display device.

A method for wireless communication with a continuous analyte sensor system is provided. The method includes receiving one or more advertisement messages from the analyte sensor system transmitted responsive to a user selection on a first display device to pair a second display device with the analyte sensor system. The method includes displaying a notification of a pairing process responsive to receiving the one or more advertisement messages. The method includes, responsive to receiving an input for initiating the pairing process from the user, transmitting a signal indicating the input has been received from the user to the first display device. The method includes receiving a transmitter ID corresponding to the analyte sensor system from the first display device. The method includes establishing a secure connection with the analyte sensor system utilizing the transmitter ID corresponding to the analyte sensor system.

In some embodiments, the first display device comprises a smartphone, and the second display device comprises a smartwatch. In some embodiments, the second display device is configured to utilize the transmitter ID to pair with the analyte sensor system.

A display device is provided. The device includes a transceiver radio configured to receive one or more advertisement messages from an analyte sensor system transmitted responsive to a selection by a user on another display device to pair the display device with the analyte sensor system. The device includes a display configured to display a notification of a pairing process responsive to the transceiver radio receiving the one or more advertisement messages. The device includes one or more processors configured to responsive to receiving an input for initiating the pairing process from the user, cause the transceiver radio to transmit a signal indicating the input has been received from the user to the other display device. The one or more processors are configured to receive a transmitter ID corresponding to the analyte sensor system from the first display device. The one or more processors are configured to establish a secure connection with the analyte sensor system utilizing the transmitter ID corresponding to the analyte sensor system.

A method for wireless communication of continuous analyte concentration data is provided. The method includes transmitting one or more first advertising messages utilizing a first set of parameters during a predetermined communication interval if a whitelist of previously authenticated devices has at least one unfilled entry. The method includes transmitting one or more second advertising messages utilizing a second set of parameters during the predetermined communication interval if the whitelist lists at least one device. The method includes establishing a first communication session between an analyte sensor system and a first device and a second communication session between the analyte sensor system and a second device during the predetermined communication interval based on at least one of the first advertising messages and the second advertising messages. The method includes transmitting analyte concentration data to the first device and to the second device utilizing at least one of the first communication session and the second communication session during the predetermined communication interval.

In some embodiments, the one or more first advertising messages advertise availability of the analyte sensor system for connection with one or more devices that are not currently listed on the whitelist and the one or more second advertising messages advertise availability of the analyte sensor system for connection with one or more devices currently listed on the whitelist.

In some embodiments, the one or more first advertising messages are transmitted after the one or more second advertising messages. In some embodiments, the one or more first advertising messages are transmitted before the one or more second advertising messages. In some embodiments, the method includes not transmitting the one or more first advertising messages during the predetermined communication interval if the whitelist does not have at least one unfilled entry. In some embodiments, the method includes not transmitting the one or more second advertising messages during the predetermined communication interval if the whitelist does not currently list any devices. In some embodiments, the method includes not transmitting the one or more second advertising messages during the predetermined communication interval if all devices currently listed on the whitelist connected to the analyte sensor system responsive to the one or more first advertising messages.

In some embodiments, the first set of parameters define one or more of a first duration of a first advertising interval for transmitting the one or more first advertising messages, a first periodic interval for transmission of the one or more first advertising messages, and a first power for transmission of the one or more first advertising messages. In some embodiments, the second set of parameters define one or more of a second duration of a second advertising interval for transmitting the one or more second advertising messages, a second periodic interval for transmission of the one or more second advertising messages, and a second power for transmission of the one or more second advertising messages. In some embodiments, the first power for transmission of the one or more first advertising messages is lower than the second power for transmission of the one or more second advertising messages. In some embodiments, devices utilized by consumers and devices utilized by medical professionals are both eligible for inclusion in the whitelist. In some embodiments, the whitelist comprises 3 or more entries.

A continuous analyte sensor system configured for wireless communication of analyte concentration data is provided. The system includes a transceiver radio configured to transmit one or more first advertising messages utilizing a first set of parameters during a predetermined communication interval if a whitelist of previously authenticated devices has at least one unfilled entry. The transceiver radio is configured to transmit one or more second advertising messages utilizing a second set of parameters during the predetermined communication interval if the whitelist lists at least one device. The system includes one or more processors configured to establish a first communication session between the analyte sensor system and a first device and a second communication session between the analyte sensor system and a second device based on at least one of the first advertising messages and the second advertising messages. The one or more processors are configured to cause the transceiver radio to transmit analyte concentration data to the first device and to the second device utilizing at least one of the first communication session and the second communication session during the predetermined communication interval.

In some embodiments, the one or more processors are configured to cause the transceiver radio to not transmit the one or more first advertising messages during the predetermined communication interval if the whitelist does not have at least one unfilled entry. In some embodiments, the one or more processors are configured to cause the transceiver radio to not transmit the one or more second advertising messages during the predetermined communication interval if the whitelist does not currently list any devices. In some embodiments, the one or more processors are configured to cause the transceiver radio to not transmit the one or more second advertising messages during the predetermined communication interval if all devices currently listed on the whitelist connected to the analyte sensor system responsive to the one or more first advertising messages.

A method of communicating continuous analyte sensor data is provided. The method includes establishing a first communication session with a first display device and a second communication session with a second display device, the second display device becoming unavailable for communication with the first device and with the analyte sensor system for a time period subsequent to establishing the second communication session. The method includes transmitting analyte sensor data to the first display device via the first communication session. The method includes storing the analyte sensor data at least during the time period. The method includes transmitting the stored analyte sensor data to the second display device utilizing the second communication session responsive to the second display device becoming available for communication with the analyte sensor system after the time period.

A continuous analyte sensor system is provided. The system includes a transceiver radio configured to establish a first communication session with a first display device and a second communication session with a second display device. The transceiver radio is configured to transmit analyte sensor data to the first display device via the first communication session. The system includes a storage configured to store the analyte sensor data at least during a time period, subsequent to establishing the second communication session, during which the second display device becomes unavailable for communication with the first device and with the analyte sensor system. The system includes one or more processor configured to cause the transceiver radio to transmit the stored analyte sensor data to the second display device utilizing the second communication session responsive to the second display device becoming available for communication with the analyte sensor system after the time period.

A method of communicating continuous analyte sensor data is provided. The method includes establishing a first communication session between a first display device and an analyte sensor system and a third communication session between the first display device and a second display device, the second display device having established a second communication session with the analyte sensor. The method includes receiving analyte sensor data from the analyte sensor system via the first communication session, wherein the second display device becomes unavailable for communication with the first display device and with the analyte sensor system for a time period subsequent to establishment of the second communication session. The method includes storing the analyte sensor data at least during the time period. The method includes transmitting the stored analyte sensor data to the second display device utilizing the third communication session responsive to the second display device becoming available for communication over the third communication session after the time period.

A first display device is provided. The device includes a transceiver radio configured to establish a first communication session with an analyte sensor system and a third communication session with a second display device, the second display device having established a second communication session with the analyte sensor. The transceiver radio is configured to receive analyte sensor data from the analyte sensor system via the first communication session, wherein the second display device becomes unavailable for communication with the first device and with the analyte sensor system for a time period subsequent to establishment of the second communication session. The device includes memory configured to store the analyte sensor data at least during the time period. The device includes one or more processors configured to transmit the stored analyte sensor data to the second device utilizing the third communication session responsive to the second device becoming available for communication over the third communication session after the time period.

A method of communicating continuous analyte sensor data is provided. The method includes establishing a first communication session with an analyte sensor system and a second communication session with a first display device. The method includes becoming unavailable for communication with the first display device and with the analyte sensor system for a time period subsequent to establishment of the first communication session. The method includes receiving analyte sensor data, previously stored by at least one of the first display device and the analyte sensor system during the time period, over at least one of the first communication session and the second communication session responsive to becoming available for communication over at least one of the first communication session and the second communication session after the time period.

A first display device is provided. The device includes a transceiver radio configured to establish a first communication session with an analyte sensor system and a second communication session with a first display device, wherein the first display device becomes unavailable for communication with the first device and with the analyte sensor system for a time period subsequent to establishment of the first communication session. The transceiver radio is configured to receive analyte sensor data, previously stored by at least one of the first device and the analyte sensor system during the time period, over at least one of the first communication session and the second communication session responsive to becoming available for communication over at least one of the first communication session and the second communication session after the time period.

A method of communicating continuous analyte sensor data is provided. The method includes determining that a first communication session between an analyte sensor system and a display device is to be closed. The method includes delaying the closing of the first communication session at least until after advertising messages have been transmitted.

In some embodiments, the determination that the first communication session is to be closed is made responsive to the first communication session being inactive for a predetermined period of time. In some embodiments, the determination that the first communication session is to be closed is made responsive to a mode of the analyte sensor system changing. In some embodiments, the mode of the analyte sensor changing comprises the analyte sensor system transitioning from performing an active glucose monitoring session to ending the active glucose monitoring session. In some embodiments, the method includes, responsive to the determining, preventing the first communication session from being closed based on receiving a plurality of heartbeat signals over the first communication session after the determining. In some embodiments, the plurality of heartbeat signals are separated from one another by a first interval and the method includes receiving a second plurality of heartbeat signals over the first communication session before the determining, the second plurality of heartbeat signals separated from one another by a second interval longer than the first interval.

A continuous analyte sensor system is provided. The system includes one or more processors configured to determine that a first communication session between with a display device is to be closed and delaying the closing of the first communication session at least until after the one or more advertising messages have been transmitted.

BRIEF DESCRIPTION OF THE DRAWINGS

Further aspects of the present disclosure will be more readily appreciated upon review of the detailed description of the various disclosed embodiments, described below, when taken in conjunction with the accompanying figures.

FIG. 8A is an operational flow diagram illustrating various operations that can be performed in accordance with embodiments of the disclosure;

Figure 1A:
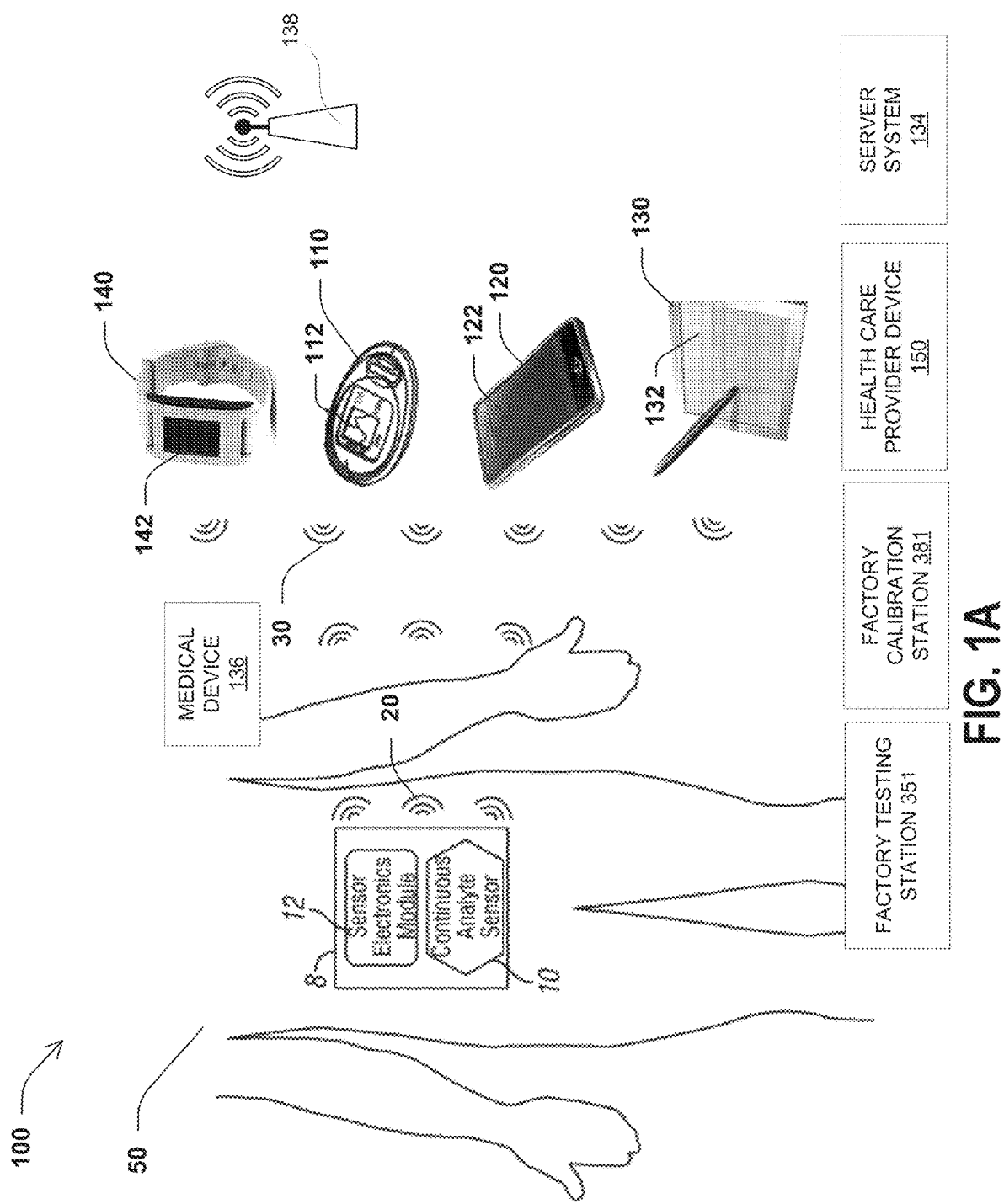
FIG. 1A illustrates aspects of an example system that can be used in connection with implementing embodiments of the disclosure.

The figures are described in greater detail in the description and examples below, are provided for purposes of illustration only, and merely depict typical or example embodiments of the disclosure. The figures are not intended to be exhaustive or to limit the disclosure to the precise form disclosed. It should also be understood that the disclosure can be practiced with modification or alteration, and that the disclosure can be limited only by the claims and the equivalents thereof.

DETAILED DESCRIPTION

Embodiments of the present disclosure are directed to systems, methods, and devices for wireless communication of analyte data. In various deployments described herein, the analyte data can be glucose data generated by an analyte sensor system configured to connect to display devices and the like. Implementing aspects of the present disclosure, as described in detail herein, can reduce the power consumption of the analyte sensor system by increasing the efficiency thereof with respect to wireless communications between the analyte sensor system and other devices. Moreover, implementing aspects of the present disclosure can also allow for reduced power consumption while maintaining and/or improving performance with respect to the reliability, speed, and accuracy of wireless communications, as well as the connection protocols associated therewith. In particular, some such aspects of the disclosure relate to, for example, authentication and encryption, connection protocols, advertisement message structure and content, device pairing, data transmission, data logging and the like.

The details of some example embodiments of the systems, methods, and devices of the present disclosure are set forth in this description and in some cases, in other portions of the disclosure. Other features, objects, and advantages of the disclosure will be apparent to one of skill in the art upon examination of the present disclosure, description, figures, examples, and claims. It is intended that all such additional systems, methods, devices, features, and advantages be included within this description (whether explicitly or by reference), be within the scope of the present disclosure, and be protected by one or more of the accompanying claims.

Overview

In some embodiments, a system is provided for continuous measurement of an analyte in a host. The system can include: a continuous analyte sensor configured to continuously measure a concentration of the analyte in the host, and a sensor electronics module physically connected to the continuous analyte sensor during sensor use. In certain embodiments, the sensor electronics module includes electronics configured to process a data stream associated with an analyte concentration measured by the continuous analyte sensor, in order to generate sensor information that includes raw sensor data, transformed sensor data, and/or any other sensor data, for example. The sensor electronics module can further be configured to generate sensor information that is customized for respective display devices, such that different display devices can receive different sensor information.

The term "analyte" as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensor heads, devices, and methods is analyte. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free 13-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica,* enterovirus, *Giardia duodenalisa, Helicobacter pylori,* hepatitis B virus, herpes virus, HIV-1, IgE (atopic disease), influenza virus, *Leishmania donovani,* leptospira, measles/mumps/rubella, *Mycobacterium leprae, Mycoplasma pneumoniae,* Myoglobin, *Onchocerca volvulus,* parainfluenza virus, *Plasmodium falciparum,* poliovirus, *Pseudomonas aeruginosa,* respiratory syncytial virus, *rickettsia* (scrub typhus), *Schistosoma mansoni, Toxoplasma gondii, Trepenoma pallidium, Trypanosoma cruzi/rangeli,* vesicular *stomatis* virus, *Wuchereria bancrofti,* yellow fever virus); specific antigens (hepatitis B virus, HIV-1); succinylacetone; sulfadoxine; theophylline; thyrotropin (TSH); thyroxine (T4); thyroxine-binding globulin; trace elements; transferring; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 7-Hydroxytryptamine (5HT), and 7-Hydroxyindoleacetic acid (FHIAA).

Alerts

In certain embodiments, one or more alerts are associated with a sensor electronics module. For example, each alert can include one or more alert conditions that indicate when the respective alert has been triggered. For example, a hypoglycemic alert can include alert conditions indicating a minimum glucose level. The alert conditions can also be based on transformed sensor data, such as trending data, and/or sensor data from multiple different sensors (e.g. an alert can be based on sensor data from both a glucose sensor and a temperature sensor). For example, a hypoglycemic alert can include alert conditions indicating a minimum required trend in the host's glucose level that must be present before triggering the alert. The term "trend," as used herein refers generally to data indicating some attribute of data that is acquired over time, e.g., such as calibrated or filtered data from a continuous glucose sensor. A trend can indicate amplitude, rate of change, acceleration, direction, etc., of data, such as sensor data, including transformed or raw sensor data.

In certain embodiments, each of the alerts is associated with one or more actions that are to be performed in response to triggering of the alert. Alert actions can include, for example, activating an alarm, such as displaying information on a display of the sensor electronics module or activating an audible or vibratory alarm coupled to the sensor electronics module, and/or transmitting data to one or more display devices external to the sensor electronics module. For any delivery action that is associated with a triggered alert, one or more delivery options define the content and/or format of the data to be transmitted, the device to which the data is to be transmitted, when the data is to be transmitted, and/or a communication protocol for delivery of the data.

In certain embodiments, multiple delivery actions (each having respective delivery options) can be associated with a single alert such that displayable sensor information having different content and formatting, for example, is transmitted to respective display devices in response to triggering of a single alert. For example, a mobile telephone can receive a data package including minimal displayable sensor information (that can be formatted specifically for display on the mobile telephone), while a desktop computer can receive a data package including most (or all) of the displayable sensor information that is generated by the sensor electronics module in response to triggering of a common alert. Advantageously, the sensor electronics module is not tied to a single display device, rather it is configured to communicate with a plurality of different display devices directly, systematically, simultaneously (e.g., via broadcasting), regularly, periodically, randomly, on-demand, in response to a query, based on alerts or alarms, and/or the like.

In some embodiments, clinical risk alerts are provided that include alert conditions that combine intelligent and dynamic estimative algorithms that estimate present or predicted danger with greater accuracy, more timeliness in pending danger, avoidance of false alarms, and less annoyance for the patient. In general, clinical risk alerts include dynamic and intelligent estimative algorithms based on analyte value, rate of change, acceleration, clinical risk, statistical probabilities, known physiological constraints, and/or individual physiological patterns, thereby providing more appropriate, clinically safe, and patient-friendly alarms. U.S. Patent Publication No. 2007/0208246, which is incorporated herein by reference in its entirety, describes some systems and methods associated with the clinical risk alerts (or alarms) described herein. In some embodiments, clinical risk alerts can be triggered for a predetermined time period to allow for the user to attend to his/her condition. Additionally, the clinical risk alerts can be de-activated when leaving a clinical risk zone so as not to annoy the patient by repeated clinical alarms (e.g., visual, audible or vibratory), when the patient's condition is improving. In some embodiments, dynamic and intelligent estimation determines a possibility of the patient avoiding clinical risk, based on the analyte concentration, the rate of change, and other aspects of the dynamic and intelligent estimative algorithms. If there is minimal or no possibility of avoiding the clinical risk, a clinical risk alert will be triggered. However, if there is a possibility of avoiding the clinical risk, the system is configured to wait a predetermined amount of time and re-analyze the possibility of avoiding the clinical risk. In some embodiments, when there is a possibility of avoiding the clinical risk, the system is further configured to provide targets, therapy recommendations, or other information that can aid the patient in proactively avoiding the clinical risk.

In some embodiments, the sensor electronics module is configured to search for one or more display devices within communication range of the sensor electronics module and to wirelessly communicate sensor information (e.g., a data package including displayable sensor information, one or more alarm conditions, and/or other alarm information) thereto. Accordingly, the display device is configured to display at least some of the sensor information and/or alarm the host (and/or caretaker), wherein the alarm mechanism is located on the display device.

In some embodiments, the sensor electronics module is configured to provide one or a plurality of different alarms via the sensor electronics module and/or via transmission of a data package indicating an alarm should be initiated by one or a plurality of display devices (e.g., sequentially and/or simultaneously). In certain embodiments, the sensor electronics module merely provides a data field indicating that an alarm conditions exists and the display device, upon reading the data field indicating the existence of the alarm condition, can decide to trigger an alarm. In some embodiments, the sensor electronics module determines which of the one or more alarms to trigger based on one or more alerts that are triggered. For example, when an alert trigger indicates severe hypoglycemia, the sensor electronics module can perform multiple actions, such as activating an alarm on the sensor electronics module, transmitting a data package to a monitoring device indicating activation of an alarm on the display, and transmitting a data package as a text message to a care provider. As an example, a text message can appear on a custom monitoring device, cell phone, pager device, and/or the like, including displayable sensor information that indicates the host's condition (e.g., "severe hypoglycemia").

In some embodiments, the sensor electronics module is configured to wait a time period for the host to respond to a triggered alert (e.g., by pressing or selecting a snooze and/or off function and/or button on the sensor electronics module and/or a display device), after which additional alerts are triggered (e.g., in an escalating manner) until one or more alerts are responded to. In some embodiments, the sensor electronics module is configured to send control signals (e.g., a stop signal) to a medical device associated with an alarm condition (e.g., hypoglycemia), such as an insulin pump, wherein the stop alert triggers a stop of insulin delivery via the pump.

In some embodiments, the sensor electronics module is configured to directly, systematically, simultaneously (e.g., via broadcasting), regularly, periodically, randomly, on-demand, in response to a query (from the display device), based on alerts or alarms, and/or the like, transmit alarm information. In some embodiments, the system further includes a repeater such that the wireless communication distance of the sensor electronics module can be increased, for example, to 10, 20, 30, 70 75, 100, 150, or 200 meters or more, wherein the repeater is configured to repeat a wireless communication from the sensor electronics module to the display device located remotely from the sensor electronics module. A repeater can be useful to families having children with diabetes. For example, to allow a parent to carry, or place in a stationary position, a display device, such as in a large house wherein the parents sleep at a distance from the child.

Display Devices

In some embodiments, the sensor electronics module is configured to search for and/or attempt wireless communication with a display device from a list of display devices. In some embodiments, the sensor electronics module is configured to search for and/or attempt wireless communication with a list of display devices in a predetermined and/or programmable order (e.g., grading and/or escalating), for example, wherein a failed attempt at communication with and/or alarming with a first display device triggers an attempt at communication with and/or alarming with a second display device, and so on. In one example embodiment, the sensor electronics module is configured to search for and attempt to alarm a host or care provider sequentially using a list of display devices, such as: (1) a default display device or a custom analyte monitoring device; (2) a mobile phone via auditory and/or visual methods, such as, text message to the host and/or care provider, voice message to the host and/or care provider, and/or 911); (3) a tablet; (4) a smart watch.

Depending on the embodiment, one or more display devices that receive data packages from the sensor electronics module are "dummy displays", wherein they display the displayable sensor information received from the sensor electronics module without additional processing (e.g., prospective algorithmic processing necessary for real-time display of sensor information). In some embodiments, the displayable sensor information comprises transformed sensor data that does not require processing by the display device prior to display of the displayable sensor information. Some display devices can include software including display instructions (software programming comprising instructions configured to display the displayable sensor information and optionally query the sensor electronics module to obtain the displayable sensor information) configured to enable display of the displayable sensor information thereon. In some embodiments, the display device is programmed with the display instructions at the manufacturer and can include security and/or authentication to avoid plagiarism of the display device. In some embodiments, a display device is configured to display the displayable sensor information via a downloadable program (for example, a downloadable Java Script, app, etc. via the internet such as but not limited to an Appstore or Google Play), such that any display device that supports downloading of a program (for example, any display device that supports Java applets) therefore can be configured to display displayable sensor information (e.g., mobile phones, tablets, PDAs, PCs and the like).

In some embodiments, certain display devices can be in direct wireless communication with the sensor electronics module, but intermediate network hardware, firmware, and/or software can be included within the direct wireless communication. In some embodiments, a repeater (e.g., a Bluetooth repeater) can be used to re-transmit the transmitted displayable sensor information to a location farther away than the immediate range of the telemetry module of the sensor electronics module, wherein the repeater enables direct wireless communication when substantive processing of the displayable sensor information does not occur. In some embodiments, a receiver (e.g., Bluetooth receiver) can be used to re-transmit the transmitted displayable sensor information, possibly in a different format, such as in a text message onto a TV screen, wherein the receiver enables direct wireless communication when substantive processing of the sensor information does not occur. In certain embodiments, the sensor electronics module directly wirelessly transmits displayable sensor information to one or a plurality of display devices, such that the displayable sensor information transmitted from the sensor electronics module is received by the display device without intermediate processing of the displayable sensor information.

In certain embodiments, one or more display devices include built-in authentication mechanisms, wherein authentication is required for communication between the sensor electronics module and the display device. In some embodiments, to authenticate the data communication between the sensor electronics module and display devices, a challenge-response protocol, such as key authentication is provided, where the challenge is a request for the key or a hash or other value based on or derived from the key, and the valid response is the correct key or a hash or other value based on or derived from the key, such that pairing of the sensor electronics module with the display devices can be accomplished by the user and/or manufacturer via the key. This can be referred to in some cases as two-way authentication. The key can be a software or hardware level key. Additionally, the key can be a password (e.g., randomly generated or set by a user or other entity), and/or can be derived from uniquely identifying features (e.g., fingerprint or retinal information) or information, etc.

In some embodiments, one or more display devices are configured to query the sensor electronics module for displayable sensor information, wherein the display device acts as a master device requesting sensor information from the sensor electronics module (e.g., a slave device) on-demand, for example, in response to a query. Although in some cases the display device acts as a master and the sensor electronics module acts as a slave, in other cases, these roles can be reversed. For example, the roles can reverse depending on the nature of the communication and so on. In some embodiments, the sensor electronics module is configured for periodic, systematic, regular, and/or periodic transmission of sensor information to one or more display devices (for example, every 30 seconds, 1, 2, 7, or 10 minutes or more). In some embodiments, the sensor electronics module is configured to transmit data packages associated with a triggered alert (e.g., triggered by one or more alert conditions). However, any combination of the above described statuses of data transmission can be implemented with any combination of paired sensor electronics module and display device(s), or between display devices themselves. For example, one or more display devices can be configured for querying the sensor electronics module database and for receiving alarm information triggered by one or more alarm conditions being met. Additionally, the sensor electronics module can be configured for periodic transmission of sensor information to one or more display devices (the same or different display devices as described in the previous example), whereby a system can include display devices that function differently regarding how sensor information is obtained.

In some embodiments, a display device is configured to query the data storage memory in the sensor electronics module for certain types of data content, including direct queries into a database in the sensor electronics module's memory and/or requests for configured or configurable packages of data content therefrom; namely, the data stored in the sensor electronics module is configurable, queryable, predetermined, and/or pre-packaged, based on the display device with which the sensor electronics module is communicating. In some additional or alternative embodiments, the sensor electronics module generates the displayable sensor information based on its knowledge of which display device is to receive a particular transmission. Additionally, some display devices are capable of obtaining calibration information and wirelessly transmitting the calibration information to the sensor electronics module, such as through manual entry of the calibration information, automatic delivery of the calibration information, and/or an integral reference analyte monitor incorporated into the display device. U.S. Patent Publication Nos. 2006/0222566, 2007/0203966, 2007/0208245, and 2005/0154271, all of which are incorporated herein by reference in their entirety, describe systems and methods for providing an integral reference analyte monitor incorporated into a display device and/or other calibration methods that can be implemented with embodiments disclosed herein. In some embodiments, such senor electronics modules may be factory calibrated such that calibration information need not be transmitted to the sensor electronics module.

In general, a plurality of display devices (e.g., a custom analyte monitoring device (which can also be referred to as an analyte display device), a mobile phone, a tablet, a smart watch, a reference analyte monitor, a drug delivery device, a medical device and a personal computer) can be configured to wirelessly communicate with the sensor electronics module. The plurality of display devices can be configured to display at least some of the displayable sensor information wirelessly communicated from the sensor electronics module. The displayable sensor information can include sensor data, such as raw data and/or transformed sensor data, such as analyte concentration values, rate of change information, trend information, alert information, sensor diagnostic information and/or calibration information, for example.

Continuous Sensor

With reference to FIG. 1A, in some embodiments, analyte sensor 10 includes a continuous glucose sensor, for example, a subcutaneous, transdermal (e.g., transcutaneous), or intravascular device. In some embodiments, such a sensor or device can analyze a plurality of intermittent blood samples. The glucose sensor can use any method of glucose-measurement, including enzymatic, chemical, physical, electrochemical, spectrophotometric, polarimetric, calorimetric, iontophoretic, radiometric, immunochemical, and the like.

A glucose sensor can use any known method, including invasive, minimally invasive, and non-invasive sensing techniques (e.g., fluorescent monitoring), to provide a data stream indicative of the concentration of glucose in a host. The data stream is typically a raw data signal, which is converted into a calibrated and/or filtered data stream that is used to provide a useful value of glucose to a user, such as a patient or a caretaker (e.g., a parent, a relative, a guardian, a teacher, a doctor, a nurse, or any other individual that has an interest in the wellbeing of the host).

A glucose sensor can be any device capable of measuring the concentration of glucose. According to one example embodiment described below, an implantable glucose sensor can be used. However, it should be understood that the devices and methods described herein can be applied to any device capable of detecting a concentration of glucose and providing an output signal that represents the concentration of glucose (e.g., as a form of analyte data).

In certain embodiments, analyte sensor 10 is an implantable glucose sensor, such as described with reference to U.S. Pat. No. 8,001,067 and U.S. Patent Publication No. US-2005-0027463-A1. In embodiments, analyte sensor 10 is a transcutaneous glucose sensor, such as described with reference to U.S. Patent Publication No. US-2006-0020187-A1. In embodiments, analyte sensor 10 is configured to be implanted in a host vessel or extracorporeally, such as is described in U.S. Patent Publication No. US-2007-0027385-A1, co-pending U.S. Patent Publication No. US-2008-0119703-A1 filed Oct. 4, 2006, U.S. Patent Publication No. US-2008-0108942-A1 filed on Mar. 26, 2007, and U.S. Patent Application No. US-2007-0197890-A1 filed on Feb. 14, 2007. In embodiments, the continuous glucose sensor includes a transcutaneous sensor such as described in U.S. Pat. No. 8,565,509 to Say et al., for example. In embodiments, analyte sensor 10 is a continuous glucose sensor that includes a subcutaneous sensor such as described with reference to U.S. Pat. No. 8,579,690 to Bonnecaze et al. or U.S. Pat. No. 8,484,046 to Say et al., for example. In embodiments, the continuous glucose sensor includes a refillable subcutaneous sensor such as described with reference to U.S. Pat. No. 8,512,939 to Colvin et al., for example. The continuous glucose sensor can include an intravascular sensor such as described with reference to U.S. Pat. No. 8,477,395 to Schulman et al., for example. The continuous glucose sensor can include an intravascular sensor such as described with reference to U.S. Pat. No. 8,424,847 to Mastrototaro et al., for example.

Figure 2A:
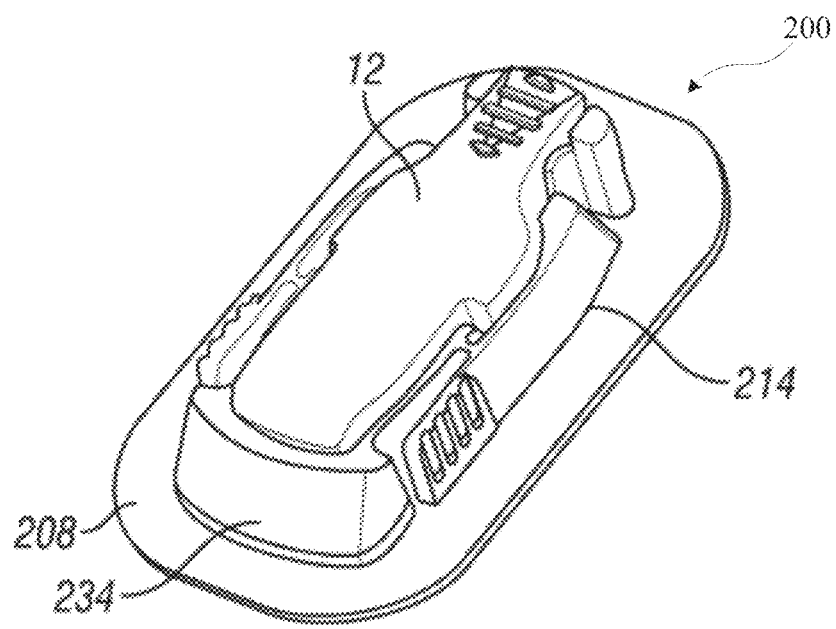
FIG. 2A is a perspective view of an example enclosure that can be used in connection with implementing embodiments of an analyte sensor system.
Figure 2B:
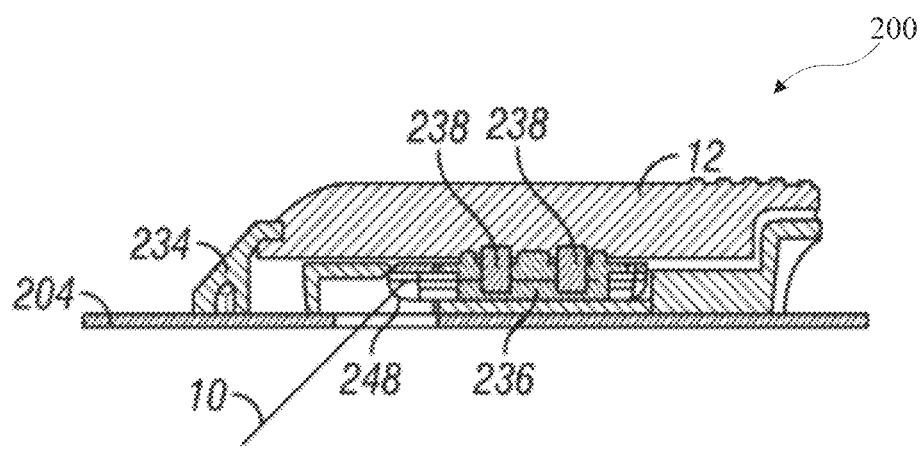
FIG. 2B is a cross-sectional view of an example enclosure that can be used in connection with implementing embodiments of an analyte sensor system.

FIGS. 2A and 2B are perspective and cross-sectional views of enclosure 200 that can be used in connection with implementing embodiments of analyte sensor system 8, according to certain aspects of the present disclosure. Enclosure 200 includes mounting unit 214 and sensor electronics module 12 attached thereto in certain embodiments. Enclosure 200 is shown in a functional position, including mounting unit 214 and sensor electronics module 12 matingly engaged therein. In some embodiments, mounting unit 214, also referred to as a housing or sensor pod, includes base 234 adapted for fastening to a host's or user's skin. Base 234 can be formed from a variety of hard or soft materials and can include a low profile for minimizing protrusion of the device from the host during use. In some embodiments, base 234 is formed at least partially from a flexible material, which can provide numerous advantages over other transcutaneous sensors, which, unfortunately, can suffer from motion-related artifacts associated with the host's movement when the host is using the device. Mounting unit 214 and/or sensor electronics module 12 can be located over the sensor insertion site to protect the site and/or provide a minimal footprint (utilization of surface area of the host's skin).

In some embodiments, a detachable connection between mounting unit 214 and sensor electronics module 12 is provided, which enables improved manufacturability, namely, the potentially relatively inexpensive mounting unit 214 can be disposed of when refurbishing or maintaining analyte sensor system 8, while the relatively more expensive sensor electronics module 12 can be reusable with multiple sensor systems. In some embodiments, sensor electronics module 12 is configured with signal processing (programming), for example, configured to filter, calibrate, and/or execute other algorithms useful for calibration and/or display of sensor information. However, an integral (non-detachable) sensor electronics module can be configured.

In some embodiments, contacts 238 are mounted on or in a subassembly hereinafter referred to as contact subassembly 236 configured to fit within base 234 of mounting unit 214 and hinge 248 that allows contact subassembly 236 to pivot between a first position (for insertion) and a second position (for use) relative to mounting unit 214. The term "hinge" as used herein is a broad term and is used in its ordinary sense, including, without limitation, to refer to any of a variety of pivoting, articulating, and/or hinging mechanisms, such as an adhesive hinge, a sliding joint, and the like; the term hinge does not necessarily imply a fulcrum or fixed point about which the articulation occurs. In some embodiments, contacts 238 are formed from a conductive elastomeric material, such as a carbon black elastomer, through which sensor 10 extends.

With further reference to FIGS. 2A, in certain embodiments, mounting unit 214 is provided with adhesive pad 208, disposed on the mounting unit's back surface and includes a releasable backing layer. Thus, removing the backing layer and pressing at last a portion of base 234 of mounting unit 214 onto the host's skin adheres mounting unit 214 to the host's skin. Additionally, or alternatively, an adhesive pad can be placed over some or all of analyte sensor system 8 and/or sensor 10 after sensor insertion is complete to ensure adhesion, and optionally to ensure an airtight seal or watertight seal around the wound exit-site (or sensor insertion site) (not shown). Appropriate adhesive pads can be chosen and designed to stretch, elongate, conform to, and/or aerate the region (e.g., host's skin). The embodiments described with reference to FIGS. 2A and 2B are described in more detail with reference to U.S. Pat. No. 7,310,544, which is incorporated herein by reference in its entirety. Configurations and arrangements can provide water resistant, waterproof, and/or hermetically sealed properties associated with the mounting unit/sensor electronics module embodiments described herein.

Various methods and devices that are suitable for use in conjunction with aspects of some embodiments are disclosed in U.S. Patent Publication No. US-2009-0240120-A1, which is incorporated herein by reference in its entirety for all purposes.

EXAMPLE CONFIGURATIONS

Referring again to FIG. 1A, system 100 that can be used in connection with implementing aspects of an analyte sensor system is depicted. In some cases, system 100 can be used to implement various systems described herein. System 100 in embodiments includes analyte sensor system 8, display devices 110, 120, 130, and 140 according to certain aspects of the present disclosure. Analyte sensor system 8 in the illustrated embodiment includes sensor electronics module 12 and continuous analyte sensor 10 associated with the sensor electronics module 12. Sensor electronics module 12 can be in wireless communication (e.g., directly or indirectly) with one or more of display devices 110, 120, 130, and 140. In embodiments, system 100 also includes medical device 136, health care provider device 150, server system 134, factory testing station 351, and factory calibration station 381. Sensor electronics module 12 can also be in wireless communication (e.g., directly or indirectly) with medical device 136, health care provider device 150, server system 134. Likewise, in some examples, display devices 110-140 can also be in wireless communication (e.g., directly or indirectly) with medical device 136, health care provider device 150, server system 134. Various couplings shown in FIG. 1A can be facilitated with wireless access point 138, as also mentioned below.

In certain embodiments, sensor electronics module 12 includes electronic circuitry associated with measuring and processing the continuous analyte sensor data, including prospective algorithms associated with processing and calibration of the sensor data. Sensor electronics module 12 can be physically connected to continuous analyte sensor 10 and can be integral with (non-releasably attached to) or releasably attachable to continuous analyte sensor 10. Sensor electronics module 12 can include hardware, firmware, and/or software that enables measurement of levels of the analyte via a glucose sensor. For example, sensor electronics module 12 can include a potentiostat, a power source for providing power to the sensor, other components useful for signal processing and data storage, and a telemetry module for transmitting data from the sensor electronics module to one or more display devices. Electronics can be affixed to a printed circuit board (PCB), or the like, and can take a variety of forms. For example, the electronics can take the form of an integrated circuit (IC), such as an Application-Specific Integrated Circuit (ASIC), a microcontroller, and/or a processor.

Sensor electronics module 12 can include sensor electronics that are configured to process sensor information, such as sensor data, and generate transformed sensor data and displayable sensor information. Examples of systems and methods for processing sensor analyte data are described in more detail herein and in U.S. Pat. Nos. 7,310,544 and 8,931,327 and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0208245, all of which are incorporated herein by reference in their entirety for all purposes.

Referring again to FIG. 1A, display devices 110, 120, 130, and/or 140 are configured for displaying (and/or alarming) the displayable sensor information that can be transmitted by sensor electronics module 12 (e.g., in a customized data package that is transmitted to the display devices based on their respective preferences). Each of display devices 110, 120, 130, or 140 can include a display such as a touchscreen display 112, 122, 132, or 142 for displaying sensor information and/or analyte data to a user and/or receiving inputs from the user. For example, a graphical user interface can be presented to the user for such purposes. In some embodiments, the display devices can include other types of user interfaces such as voice user interface instead of or in addition to a touchscreen display for communicating sensor information to the user of the display device and/or receiving user inputs. In some embodiments, one, some, or all of the display devices is configured to display or otherwise communicate the sensor information as it is communicated from the sensor electronics module (e.g., in a data package that is transmitted to respective display devices), without any additional prospective processing required for calibration and real-time display of the sensor data.

Figure 1B:
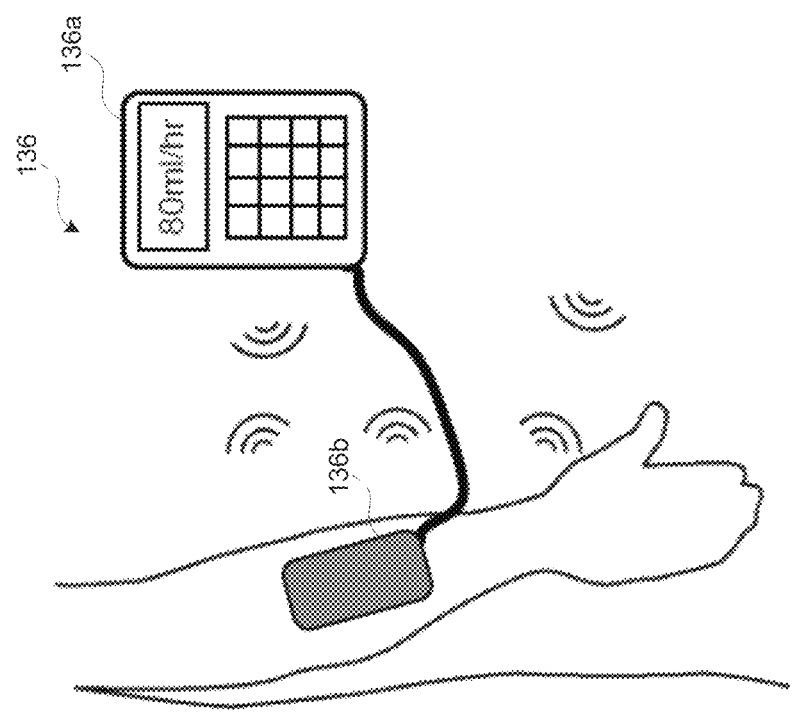
FIG. 1B illustrates aspects of an example system that can be used in connection with implementing embodiments of the disclosure.

Medical device 136 can be a passive device in example embodiments of the disclosure. For example, medical device 136 can be an insulin pump for administering insulin to a user, as shown in FIG. 1B. For a variety of reasons, it can be desirable for such an insulin pump to receive and track glucose values transmitted from analyte sensor system 8. One reason is to provide the insulin pump a capability to suspend/activate insulin administration based on a glucose value being below/above a threshold value. One solution that allows a passive device (e.g., medical device 136) to receive analyte data (e.g., glucose values) without being bonded to analyte sensor system 8 is to include the analyte data in the advertisement messages transmitted from analyte sensor system 8. The data included in the advertisement messages can be encoded so that only a device that has the identification information associated with analyte sensor system 8 can decode the analyte data. Medical device 136 can include input/output portion 136a, in which, for example, glucose and other values can be displayed and input can be received via buttons, wireless connection, or other mechanisms. Medical device 136 can also include attachment portion 136b that interfaces with the user to, for example, administrate insulin responsive to the input received at input/output portion 136a. In some cases, attachment portion 136b can provide sensory alerts or other notifications to the user based on, for example, the input received and/or values calculated at input/output portion 136a.

Health care provider device 150 can be utilized by health care providers to track, log, and/or otherwise analyze data provided by one or more analyte sensor systems, as disclosed herein. Several example embodiments of health care provider device 150 will be described in more detail in connection with FIGS. 26-27B below.

Factory calibration station 381 can be utilized to calibrate one or more analyte sensor systems, as disclosed herein. Several example embodiments of factory calibration station 381 will be described in more detail in connection with FIGS. 3D and 5 below.

Factory testing station 351 can be utilized to test one or more analyte sensor systems, as disclosed herein. Several example embodiments of factory testing station 351 will be described in more detail in connection with FIGS. 3E, 6A and 6B below.

With further reference to FIG. 1A, the plurality of display devices can include a custom display device specially designed for displaying certain types of displayable sensor information associated with analyte data received from sensor electronics module 12 (e.g., a numerical value and an arrow, in some embodiments). Analyte display device 110 is an example of such a custom device. In some embodiments, one of the plurality of display devices is a smartphone, such as mobile phone 120 based on an Android, iOS or other operating system, and configured to display a graphical representation of the continuous sensor data (e.g., including current and historic data). Other display devices can include other hand-held devices, such as tablet 130, smart watch 140, medical device 136 (e.g., an insulin delivery device or a blood glucose meter), and/or a desktop or laptop computer.

Because different display devices provide different user interfaces, content of the data packages (e.g., amount, format, and/or type of data to be displayed, alarms, and the like) can be customized (e.g., programmed differently by the manufacture and/or by an end user) for each particular display device. Accordingly, in the embodiment of FIG. 1A, a plurality of different display devices can be in direct wireless communication with a sensor electronics module (e.g., such as an on-skin sensor electronics module 12 that is physically connected to the continuous analyte sensor 10) during a sensor session to enable a plurality of different types and/or levels of display and/or functionality associated with the displayable sensor information, which is described in more detail elsewhere herein.

As further illustrated in FIG. 1A, system 100 can also include wireless access point (WAP) 138 that can be used to couple one or more of analyte sensor system 8, the plurality display devices, server system 134, and medical device 136 to one another. For example, WAP 138 can provide Wi-Fi and/or cellular connectivity within system 100. Near Field Communication (NFC) can also be used among devices of system 100. Server system 134 can be used to collect analyte data from analyte sensor system 8 and/or the plurality of display devices, for example, to perform analytics thereon, generate universal or individualized models for glucose levels and profiles, and so on.

Figure 3A:
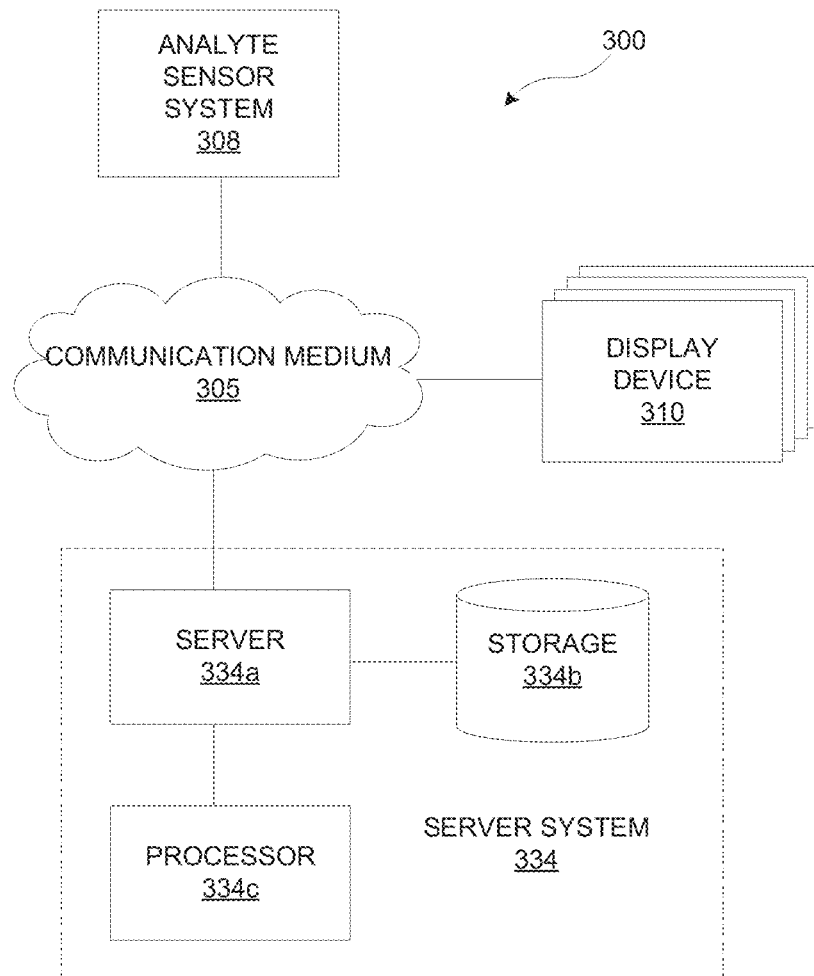
FIG. 3A illustrates aspects of an example system that can be used in connection with implementing embodiments of the disclosure.

Referring now to FIG. 3A, system 300 is depicted. System 300 can be used in connection with implementing embodiments of the disclosed systems, methods, and devices. By way of example, the various below-described components of FIG. 3A can be used to provide wireless communication of glucose data, for example between an analyte sensor system and a plurality of display devices, medical devices, servers and so on.

As shown in FIG. 3A, system 100 can include analyte sensor system 308 and one or more display devices 310. Additionally, in the illustrated embodiment, system 300 includes server system 334, which in turn includes server 334a coupled to processor 334c and storage 334b. Analyte sensor system 308 can be coupled to display devices 310 and/or server system 334 via communication medium 305.

As will be described in detail herein, analyte sensor system 308 and display devices 310 can exchange messaging via communication medium 305, and communication medium 305 can also be used to deliver analyte data to display devices 310 and/or server system 334. Display devices 310 can include a variety of electronic computing devices, such as, for example, a smartphone, tablet, laptop, wearable device such as a smartwatch, etc. Display devices 310 can also include analyte display device 110, medical device 136, health care provider device 150, server system 134, factory testing station 351, and factory calibration station 381. Here, it will be noted that a graphical user interface (GUI) of display device 310 can perform such functions as accepting user input and displaying menus as well as information derived from analyte data. The GUI can be provided by various operating systems known in the art, such as, for example, iOS, Android, Windows Mobile, Windows, Mac OS, Chrome OS, Linux, Unix, a gaming platform OS (e.g., Xbox, PlayStation, Wii), etc. In various embodiments, communication medium 305 can be based on one or more wireless communication protocols such as Bluetooth, Bluetooth Low Energy (BLE), ZigBee, Wi-Fi, 802.11 protocols, Infrared (IR), Radio Frequency (RF), 2G, 3E, 4G, 7G etc., and/or wired protocols and media.

In various embodiments, the elements of system 300 can be used to perform various processes described herein and/or can be used to execute various operations described herein regarding one or more disclosed systems and methods. Upon studying the present disclosure, one of skill in the art will appreciate that system 300 can include multiple analyte sensor systems, communication media 305 for communication utilizing the same or different communication protocols, and/or server systems 334.

As mentioned, communication medium 305 can be used to connect or communicatively couple analyte sensor system 308, display devices 310, and/or server system 334 to one another or to a network, and communication medium 305 can be implemented in a variety of forms. For example, communication medium 305 can include an Internet connection, such as a local area network (LAN), a wide area network (WAN), a fiber optic network, internet over power lines, a hard-wired connection (e.g., a bus), and the like, or any other kind of network connection. Communication medium 305 can be implemented using any combination of routers, cables, modems, switches, fiber optics, wires, radio (e.g., microwave/RF links), and the like. Further, communication medium 305 can be implemented using various wireless standards, such as Bluetooth®, BLE, Wi-Fi, 3EPP standards (e.g., 2G GSM/GPRS/EDGE, 3E UMTS/CDMA2000, 4G LTE/LTE-U, 5G), etc. Upon reading the present disclosure, one of skill in the art will recognize other ways to implement communication medium 305 for communications purposes.

Server 334a can receive, collect, or monitor information, including analyte data and related information, from analyte sensor system 308 and/or display device 310, such as input responsive to the analyte data or input received in connection with an analyte monitoring application running on analyte sensor system or display device 310. In such cases, server 334a can be configured to receive such information via communication medium 305. This information can be stored in storage 334b and can be processed by processor 334c. For example, processor 334c can include an analytics engine capable of performing analytics on information that server 334a has collected, received, etc. via communication medium 305. In embodiments, server 334a, storage 334b, and/or processor 334c can be implemented as a distributed computing network, such as a Hadoop® network, or as a relational database or the like.

Server 334a can include, for example, an Internet server, a router, a desktop or laptop computer, a smartphone, a tablet, a processor, a module, or the like, and can be implemented in various forms, including, for example, an integrated circuit or collection thereof, a printed circuit board or collection thereof, or in a discrete housing/package/rack or multiple of the same. In embodiments, server 334a at least partially directs communications made over communication medium 305. Such communications include the delivery and/or messaging (e.g., advertisement, command, or other messaging) and analyte data. For example, server 334a can process and exchange messages between analyte sensor system 308 and display devices 310 related to frequency bands, timing of transmissions, security, alarms, and so on. Server 334a can update and/or provide information stored on analyte sensor system 308 and/or display devices 310, for example, by delivering applications, security codes, transmitter IDs, pairing keys, etc. thereto. Server 334a can send/receive information to/from analyte sensor system 308 and/or display devices 310 in real time or sporadically. Further, server 334a can implement cloud computing capabilities for analyte sensor system 308 and/or display devices 310.

Figure 3B:
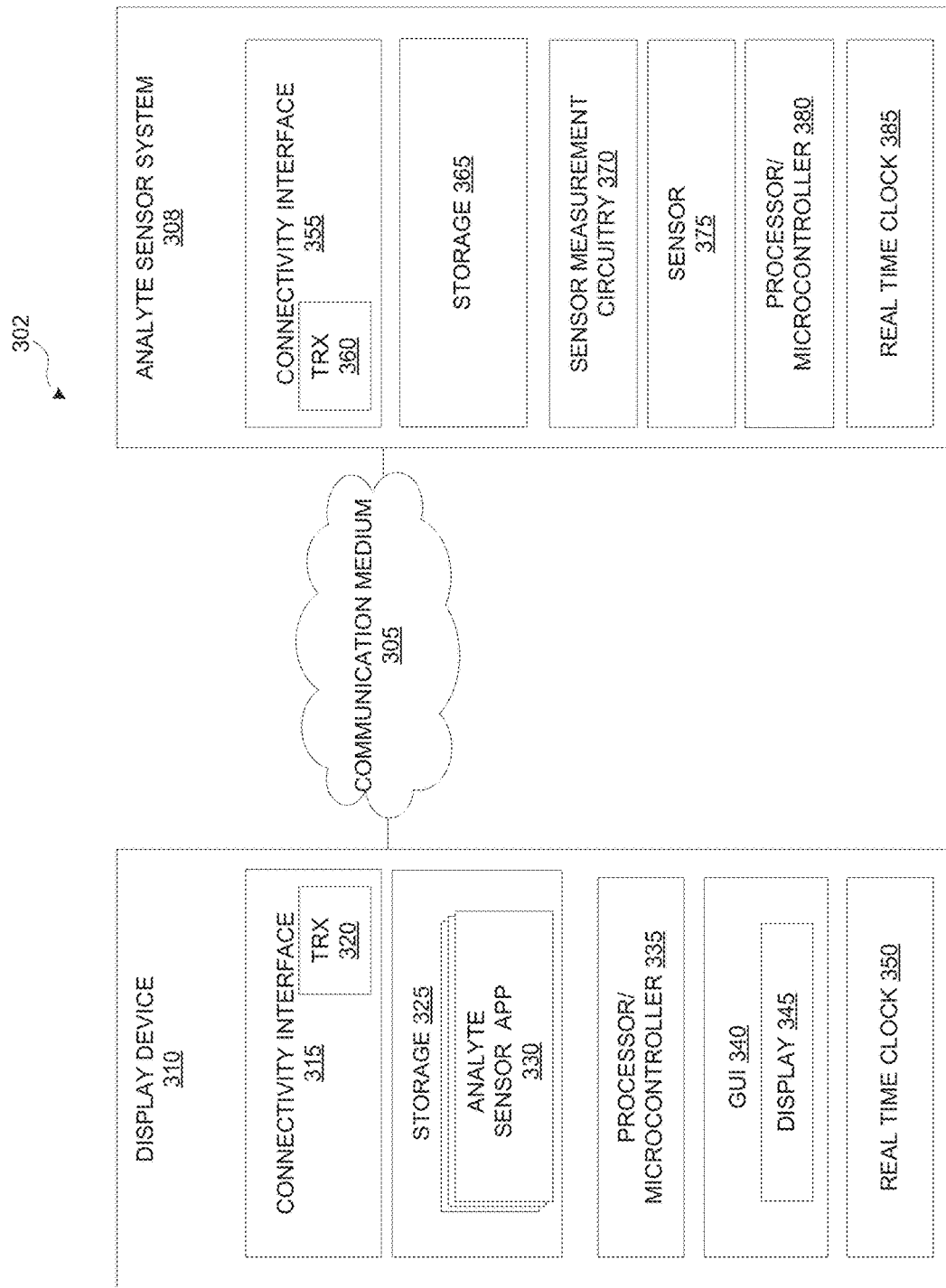
FIG. 3B illustrates aspects of an example system that can be used in connection with implementing embodiments of the disclosure.

FIG. 3B depicts system 302, which includes examples of additional aspects of the present disclosure that can be used in connection implementing an analyte sensor system. As illustrated in FIG. 3B, system 302 can include analyte sensor system 308. As shown, analyte sensor system 308 can include analyte sensor 375 (e.g., which can also be designated with the numeral 10 in FIG. 1A) coupled to sensor measurement circuitry 370 for processing and managing sensor data. Sensor measurement circuitry 370 can be coupled to processor/microprocessor 380 (e.g., which can be part of the sensor electronics module 12 in FIG. 1A). In some embodiments, processor 380 can perform part or all of the functions of the sensor measurement circuitry 370 for obtaining and processing sensor measurement values from sensor 375. Processor 380 can be further coupled to a radio unit or transceiver 360 (e.g., which can be part of the sensor electronics module 12 in FIG. 1A) for sending sensor data and receiving requests, commands and/or temporary power from an external device, such as display device 310, which can be used to display or otherwise provide the sensor data (or analyte data) to a user. As used herein, the terms "radio," "radio unit," "transceiver," "radio transceiver" and "transceiver radio" are used interchangeably and generally refer to a device, circuitry or module that can wirelessly transmit and receive data. In addition, according to some embodiments, transceiver 360 can further comprise an NFC antenna and associated circuitry configured to receive power from another device, e.g., display device 310, via a near field communication, which analyte sensor system 308 can utilized to temporarily power one or more of its components necessary for communicating with another device, for example, in cases where an internal battery of analyte sensor system 308 (not shown) has insufficient power or is otherwise unable to adequately power such components. Analyte sensor system 308 can further include storage 365 (e.g., which can be part of the sensor electronics module 12 in FIG. 1A) and real time clock (RTC) 380 (e.g., which can be part of the sensor electronics module 12 in FIG. 1A) for storing and tracking sensor data.

As alluded to above, wireless communication protocols can be used to transmit and receive data between analyte sensor system 308 and the display device 310 via communication medium 305. Such wireless protocols can be designed for use in a wireless network that is optimized for periodic and small data transmissions (that can be transmitted at low rates if necessary) to and from multiple devices in a close range (e.g., a personal area network (PAN)). For example, one such protocol can be optimized for periodic data transfers where transceivers can be configured to transmit data for short intervals and then enter low power modes for long intervals. The protocol can have low overhead requirements both for normal data transmissions and for initially setting up communication channels (e.g., by reducing overhead) to reduce power consumption. In some embodiments, burst broadcasting schemes (e.g., one-way communication) can be used. This can eliminate overhead required for acknowledgement signals and allow for periodic transmissions that consume little power. In other embodiments, passive or active proximity-based protocols can be employed to reduce overhead (e.g., overhead associated with typical pairing operations) and/or increase security, with NFC being one specific example.

The protocols can further be configured to establish communication channels with multiple devices while implementing interference avoidance schemes. In some embodiments, the protocol can make use of adaptive isochronous network topologies that define various time slots and frequency bands for communication with several devices. The protocol can thus modify transmission windows and frequencies in response to interference and to support communication with multiple devices. Accordingly, the wireless protocol can use time and frequency division multiplexing (TDMA) based schemes. The wireless protocol can also employ direct sequence spread spectrum (DSSS) and frequency-hopping spread spectrum schemes. Various network topologies can be used to support short-distance and/or low-power wireless communication such as peer-to-peer, start, tree, or mesh network topologies such as Wi-Fi, Bluetooth and Bluetooth Low Energy (BLE). The wireless protocol can operate in various frequency bands such as an open ISM band such as 2.4 GHz. Furthermore, to reduce power usage, the wireless protocol can adaptively configure data rates according to power consumption.

With further reference to FIG. 3B, system 302 can include display device 310 communicatively coupled to analyte sensor system 308 via communication medium 305. In the illustrated embodiment, display device 310 includes connectivity interface 315 (which in turn includes transceiver 320), storage 325 (which in turn stores analyte sensor application 330 and/or additional applications), processor/microprocessor 335, graphical user interface (GUI) 340 that can be presented using display 345 of display device 310, and real time clock (RTC) 350. A bus (not shown here) can be used to interconnect the various elements of display device 310 and transfer data between these elements.

Display device 310 can be used for alerting and providing sensor information or analyte data to a user and can include a processor/microprocessor 335 for processing and managing sensor data. Display device 310 can include display 345, storage 325, analyte sensor application 330, and real time clock 350 for displaying, storing, and tracking sensor data. Display device 310 can further include a radio unit or transceiver 320 coupled to other elements of display device 310 via connectivity interface 315 and/or a bus. Transceiver 320 can be used for receiving sensor data and for sending requests, instructions, data, and/or power to analyte sensor system 308. Transceiver 320 can further employ a communication protocol. Storage 325 can also be used for storing an operating system for display device 310 and/or a custom (e.g., proprietary) application designed for wireless data communication between a transceiver and display device 310. Storage 325 can be a single memory device or multiple memory devices and can be a volatile or non-volatile memory for storing data and/or instructions for software programs and applications. The instructions can be executed by processor 335 to control and manage transceiver 320.

In some embodiments, when a standardized communication protocol is used, commercially available transceiver circuits can be utilized that incorporate processing circuitry to handle low level data communication functions such as the management of data encoding, transmission frequencies, handshake protocols, and the like. In these embodiments, processor 335, 380 does not need to manage these activities, but rather provides desired data values for transmission, and manages high level functions such as power up or down, set a rate at which messages are transmitted, and the like. Instructions and data values for performing these high-level functions can be provided to the transceiver circuits via a data bus and transfer protocol established by the manufacturer of the transceiver 320, 360.

Components of analyte sensor system 308 can require replacement periodically. For example, analyte sensor system 308 can include an implantable sensor 375 that can be attached to a sensor electronics module, e.g., sensor electronics module 12, that includes sensor measurement circuitry 370, processor 380, storage 365, and transceiver 360, and a battery (not shown). Sensor 375 can require periodic replacement (e.g., every 7 to 30 days). The sensor electronics module can be configured to be powered and active for much longer than sensor 375 (e.g., for three to six months or more) until the battery needs replacement. Replacing these components can be difficult and require the assistance of trained personnel. Reducing the need to replace such components, particularly the battery, significantly improves the convenience and cost of using analyte sensor system 308, including to the user. In some embodiments, when a sensor electronic module is used for the first time (or reactivated once a battery has been replaced in some cases), it can be connected to sensor 375 and a sensor session can be established. As will be further described below, there can be a process for initially establishing communication between display device 310 and the sensor electronics module, e.g., sensor electronics module 12, when the module is first used or re-activated (e.g., the battery is replaced). Once display device 310 and sensor electronics module have established communication, display device 310 and the sensor electronics module can periodically and/or continuously be in communication over the life of several sensors 375 until, for example, the battery needs to be replaced. Each time sensor 375 is replaced, a new sensor session can be established. The new sensor session can be initiated through a process completed using display device 310 and the process can be triggered by notifications of a new sensor via the communication between the sensor electronics module and display device 310 that can be persistent across sensor sessions.

Analyte sensor system 308 typically gathers analyte data from sensor 375 and transmits the same to display device 310. Data points regarding analyte values can be gathered and transmitted over the life of sensor 375 (e.g., in the range of 1 to 30 days or more). New measurements can be transmitted often enough to adequately monitor glucose levels. Rather than having the transmission and receiving circuitry of each of analyte sensor system 308 and display device 310 continuously communicating, analyte sensor system 308 and display device 310 can regularly and/or periodically establish a communication channel between them. Thus, analyte sensor system 308 can in some cases communicate via wireless transmission with display device 310 (e.g., a hand-held computing device, medical device, or proprietary device) at predetermined time intervals. The duration of the predetermined time interval can be selected to be long enough so that analyte sensor system 308 does not consume too much power by transmitting data more frequently than needed, yet frequent enough to provide substantially real-time sensor information (e.g., measured glucose values or analyte data) to display device 310 for output (e.g., via display 345) to a user. While the predetermined time interval is every five minutes in some embodiments, it is appreciated that this time interval can be varied to be any desired length of time.

With continued reference to FIG. 3B, as shown, connectivity interface 315 interfaces display device 310 to communication medium 305, such that display device 310 can be communicatively coupled to analyte sensor system 308 via communication medium 305. Transceiver 320 of connectivity interface 315 can include multiple transceiver modules and/or circuitry operable on different wireless standards. Transceiver 320 can be used to receive analyte data and associated commands and messages from analyte sensor system 308. In some embodiments, transceiver 320 can comprise a near field communication (NFC) controller configured to transmit an NFC signal for communicating with and/or temporarily providing power to another device, for example, analyte sensor system 308, as will be described in more detail in connection with one or more embodiments below. Additionally, connectivity interface 315 can in some cases include additional components for controlling radio and/or wired connections, such as baseband and/or Ethernet modems, audio/video codecs, BLE, Bluetooth, and/or cellular connections and so on.

Storage 325 can include volatile memory (e.g. RAM) and/or non-volatile memory (e.g. flash storage), can include any of EPROM, EEPROM, cache, or can include some combination/variation thereof. In various embodiments, storage 325 can store user input data and/or other data collected by display device 310 (e.g., input from other users gathered via analyte sensor application 330). Storage 325 can also be used to store volumes of analyte data received from analyte sensor system 308 for later retrieval and use, e.g., for determining trends and triggering alerts. Additionally, storage 325 can store analyte sensor application 330 that, when executed using processor 335, for example, receives input (e.g., by a conventional hard/soft key or a touch screen, voice detection, or other input mechanism), and allows a user to interact with the analyte data and related content via GUI 340, as will be described in further detail herein.

In various embodiments, a user can interact with analyte sensor application 330 via GUI 340, which can be provided by display 345 of display device 310. By way of example, display 345 can be a touchscreen display that accepts various hand gestures as inputs. Application 330 can process and/or present analyte-related data received by display device 310, according to various operations described herein, and present such data via display 345. Additionally, application 330 can be used to obtain, access, display, control, and/or interface with analyte data and related messaging and processes associated with analyte sensor system 308, as is described in further detail herein.

Application 330 can be downloaded, installed, and initially configured/setup on display device 310. For example, display device 310 can obtain application 330 from server system 334, or from another source accessed via a communication medium (e.g., communication medium 305), such as an application store or the like. Following installation and setup, application 330 can be used to access and/or interface with analyte data (e.g., whether stored on server system 334, locally from storage 325, or from analyte sensor system 308). By way of illustration, application 330 can present a menu that includes various controls or commands that can be executed in connection with the operating of analyte sensor system 308 and one or more display devices 310. Application 330 can also be used to interface with or control other display devices 310, for example, to deliver or make available thereto analyte data, including for example by receiving/sending analyte data directly to the other display device 310 and/or by sending an instruction for analyte sensor system 308 and the other display device 310 to be connected, etc., as will be described herein. Additionally, application 330 in some implementations can interact with one or more additional applications supported by display device 310, for example to retrieve or supply relevant data. Such applications can include, by way of example, fitness/lifestyle monitoring applications, social media applications, and so on.

Analyte sensor application 330 can include various code/functional modules, such as, for example, a display module, a menu module, a list module, and so on as will become clear in light of the description of various functionalities herein (e.g., in connection with disclosed methods). These modules can be implemented separately or in combination. Each module can include computer-readable media and have computer-executable code stored thereon, such that the code can be operatively coupled to and/or executed by processor 335 (which, e.g., can include a circuitry for such execution) to perform specific functions (e.g., as described herein with regard to various operations and flow charts etc.) with respect to interfacing with analyte data and performing tasks related thereto. As will be further described below, a display module can present (e.g., via display 345) various screens to a user, with the screens containing graphical representations of information provided by application 330. In further embodiments, application 330 can be used to display to the user an environment for viewing and interacting with various display devices that can be connectable to analyte sensor system 308, as well as with analyte sensor system 308 itself. Sensor application 330 can include a native application modified with a software design kit (e.g., depending on the operating system) in order to carry out the functionalities/features described herein.

Referring again to FIG. 3B, display device 310 also includes processor/microcontroller 335. Processor 335 can include processor sub-modules, including, by way of example, an applications processor that interfaces with and/or controls other elements of display device 310 (e.g., connectivity interface 315, application 330, GUI 340, display 345, RTC 350, etc.). Processor 335 can include a controller and/or microcontroller that provides various controls (e.g., interfaces with buttons and switches) related to device management, such as, for example, lists of available or previously paired devices, information related to measurement values, information related to network conditions (e.g., link quality and the like), information related to the timing, type, and/or structure of messaging exchanged between analyte sensor system 308 and display device 310, and so on. Additionally, the controller can include various controls related to the gathering of user input, such as, for example, a user's finger print (e.g., to authorize the user's access to data or to be used for authorization/encryption of data, including analyte data), as well as analyte data.

Processor 335 can include circuitry such as logic circuits, memory, a battery and power circuitry, and other circuitry drivers for periphery components and audio components. Processor 335 and any sub-processors thereof can include logic circuits for receiving, processing, and/or storing data received and/or input to display device 310, and data to be transmitted or delivered by display device 310. Processor 335 can be coupled by a bus to display 345 as well as connectivity interface 315 and storage 325 (including application 330). Hence, processor 335 can receive and process electrical signals generated by these respective elements and thus perform various functions. By way of example, processor 335 can access stored content from storage 325 at the direction of application 330 and process the stored content for display and/or output by display 345. Additionally, processor 335 can process the stored content for transmission via connectivity interface 315 and communication medium 305 to other display devices 310, analyte sensor system 308, or server system 334. Display device 310 can include other peripheral components not shown in detail in FIG. 3B.

In further embodiments, processor 335 can further obtain, detect, calculate, and/or store data input by a user via display 345 or GUI 340, or data received from analyte sensor system 308 (e.g., analyte sensor data or related messaging), over a period of time. Processor 335 can use this input to gauge the user's physical and/or mental response to the data and/or other factors (e.g., time of day, location, etc.). In various embodiments, the user's response or other factors can indicate preferences with respect to the use of certain display devices 310 under certain conditions, and/or the use of certain connection/transmission schemes under various conditions, as will be described in further detail herein.

It should be noted at this juncture that like-named elements as between display device 310 and analyte sensor system 308 can include similar features, structures, and/or capabilities. Therefore, with respect to such elements, the description of display device 310 above can in some cases be applied to analyte sensor system 308.

Figure 3C:
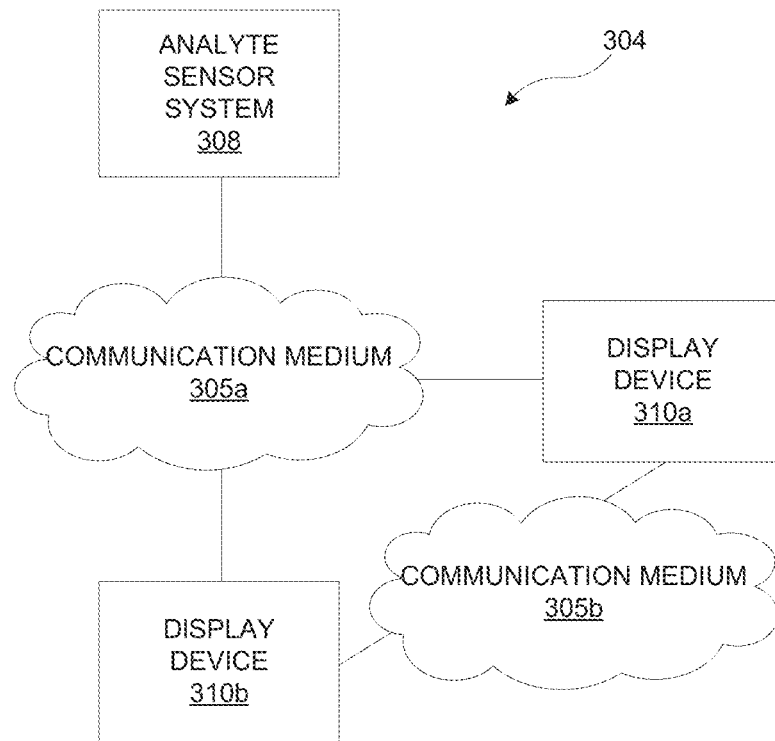
FIG. 3C illustrates aspects of an example system that can be used in connection with implementing embodiments of the disclosure.

Turning now to FIG. 3C, system 304 is depicted in accordance with embodiments of the present disclosure. As shown, system 304 includes analyte sensor system 308 communicatively coupled with display devices 310a, 310b via communication medium 305a. Display device 310a is also communicatively coupled to display device 310b via communication medium 305b. By way of example, FIG. 3C illustrates that in example implementations of the disclosure, display device 310a can connect to analyte sensor system 308 using a first connection scheme and a first wireless protocol (e.g., BLE or any other preferred communication protocol and/or scheme). In embodiments, display device 310b can also connect to analyte sensor system 308 using the first connection scheme and first wireless protocol (e.g., BLE) and/or utilizing a second connection scheme and a second wireless protocol different from the first connection scheme and first wireless protocol. In turn, display device 310a can also connect to display device 310b using any one of the first connection scheme and first wireless protocol, the second connection scheme and second wireless protocol and/or a third connection scheme and a third wireless protocol (e.g., Wi-Fi, NFC, etc.). Further, for example, display devices 310a and 310b can exchange analyte data with one another via communication medium 305b, where each display device 310a, 310b received the analyte data via communication medium 305a, that is, from analyte sensor system 308. Additional aspects and features represented by FIG. 3C will become apparent upon studying the entirety of the present disclosure.

Factory Calibration and Testing

Before a user can utilize analyte sensor system 308, it can first be programmed and/or factory calibrated with sensor calibration data. Such programming can include at least the loading of sensor calibration data for sensor 375 and/or sensor measurement circuitry 370 (FIG. 3B) onto storage 365 so that sensor measurement circuitry 370 can accurately measure, estimate or otherwise determine an analyte concentration for a user based on a signal from sensor 375. However, because such programming must be performed for many analyte sensor systems, in some cases thousands of units or more, it is desirable to streamline the programming and/or factory calibration process as much as practical. Accordingly, some embodiments described below provide streamlined factory calibration of sensor 375 and/or sensor measurement circuitry 370 by minimizing an amount of communication required to initiate and validate a connection between a factory calibration system and analyte sensor system 308 and by minimizing an amount of communication utilized while performing the factory calibration.

Figure 3D:
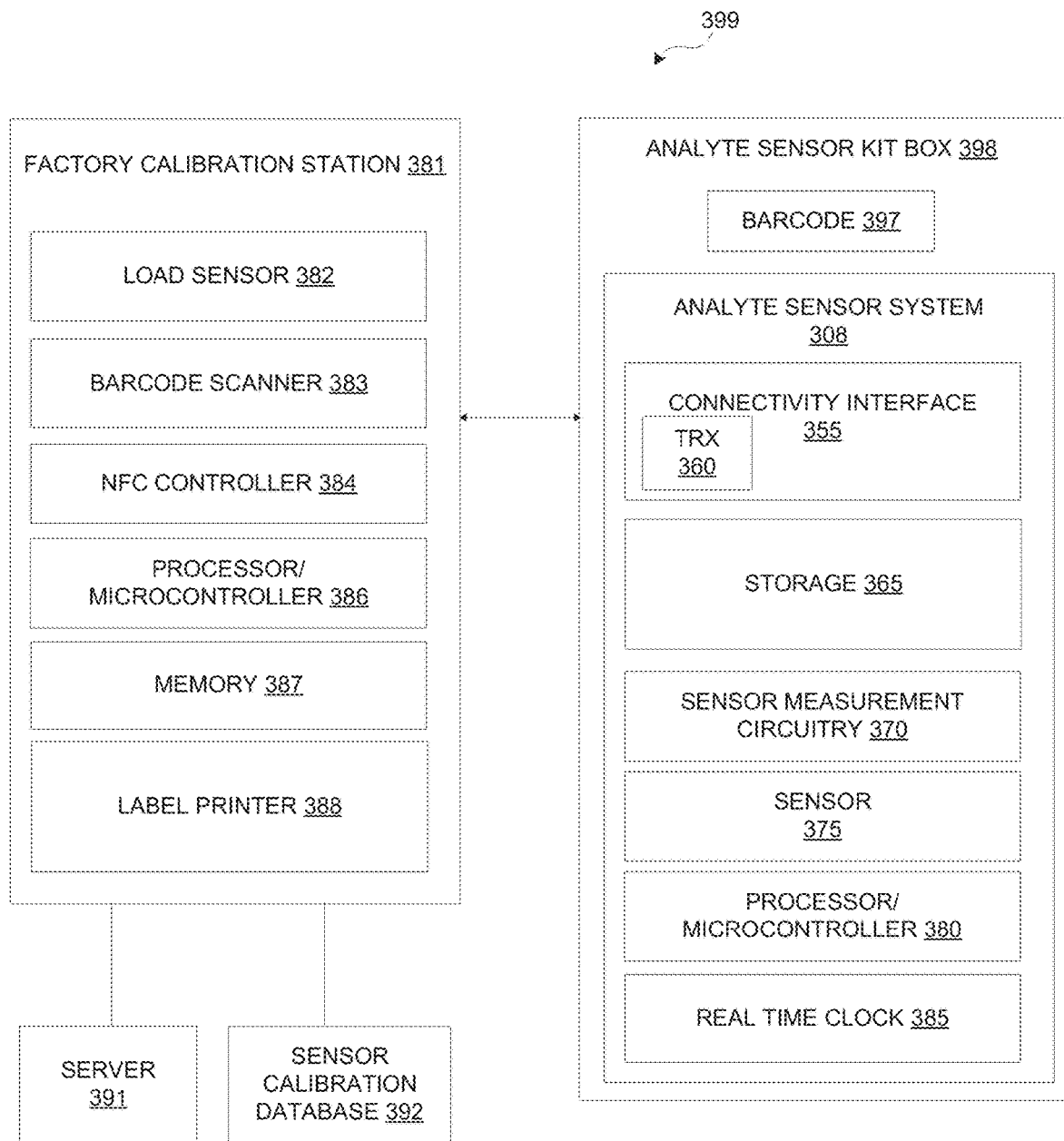
FIG. 3D illustrates aspects of an example factory calibration system that can be used in connection with implementing embodiments of the disclosure.

FIG. 3D illustrates aspects of an example factory calibration system 399 that can be used in connection with implementing embodiments of the disclosure. System 399 can comprise one or more of a factory calibration station 381, a sensor calibration database 392, a server 391 and an analyte sensor kit box 398. Several components of factory calibration station 381, sensor calibration database 392, server 391 and analyte sensor kit box 398 will be described below. However, it should be understood that factory calibration station 381, sensor calibration database 392, server 391 and analyte sensor kit box 398 can comprise more, fewer or different components than those discussed.

In some embodiments, analyte sensor system 308 can be packaged along with at least an applicator (not shown) within analyte sensor kit box 398. An identification tag 397 (e.g., a barcode, QR code or the like) can be disposed on analyte sensor system 308, the applicator, analyte sensor kit box 398, or at any location such that identification tag 397 is readily accessible by factory calibration station 381, e.g., without altering, opening or unpacking analyte sensor kit box 398. Identification tag 397 can be encoded to identify the specific sensor 375 disposed within analyte sensor system 308. For example, in some embodiments, identification tag 397 can be encoded with at least an applicator lot number corresponding to the applicator disposed within analyte sensor kit box 398 and a sensor serial number corresponding to sensor 375 disposed within analyte sensor system 308, as will be described in more detail below.

Factory calibration station 381 can comprise a processor 386 and a memory 387 configured to communicate with one or more other components of factory calibration station 381, server 391, sensor calibration database 392 and/or analyte sensor system 308. In some embodiments, memory 387 can have loaded thereon non-transitory computer-readable instructions that, when executed by processor 386, enable functionality at least as described in this disclosure.

Factory calibration station 381 can comprise a load sensor 382 configured to sense when analyte sensor kit box 398 is properly positioned on or near factory calibration station 381 for factory calibration of analyte sensor system 308. In some embodiments, load sensor 382 can comprise a scale and proper positioning of analyte sensor kit box 398 can be sensed based on load sensor 382 generating a signal indicating a load on load sensor 382 that can correspond to analyte sensor kit box 398.

Factory calibration station 381 can further comprise a identification tag scanner 383 configured to read identification tag 397. The information encoded in identification tag 397 can then be utilized by factory calibration station 381 to retrieve the unique sensor calibration data for sensor 375 from sensor calibration database 392. In some embodiments, sensor calibration data for a plurality of sensors including sensor 375 can be stored in sensor calibration database 392 in the form of a .CSV lookup table. However, the present disclosure is not so limited, and the sensor calibration data can be stored in any form.

Factory calibration station 381 can further comprise a short-range communications controller 384 configured to communicate with transmitter 360 (which can include a short-range antenna and associated circuitry) to thereby wake, e.g., transition to an operational mode, one or more components of analyte sensor system 308 when analyte sensor system 308 is brought into sufficiently close proximity to controller 384. In some embodiments, controller 384 may comprise a near-field communication (NFC) controller. Controller 384 can then transfer at least a portion of the sensor calibration data for sensor 375 retrieved from sensor calibration database 392 to analyte sensor system 308, via transmitter 360. The transferred sensor calibration data can be written and/or stored in one or more locations within storage 365 of analyte sensor system 308. In some embodiments, since NFC communication protocols are utilized, the sensor calibration data can be written to the one or more locations within storage 365 utilizing a single NFC command (e.g., 0x7A—get sensor parameters), thereby eliminating or at least substantially reducing the use of other time-consuming pairing and authenticating protocols during at least this phase of factory calibration.

Factory calibration station 381 can further comprise one or more label printers 388 configured to print one or more labels indicating data associated with the factory calibration process for analyte sensor system 308.

Factory calibration station 381 can be further configured to generate and/or communicate information regarding the factory calibration process for analyte sensor system 308 to server 391, which can be configured to generate and/or transmit one or more summary reports related to the factory calibration process of one or more analyte sensor systems.

Some embodiments describe examples of encoding of the information provided by identification tag 397 below. Identification tag 397 can be a 2-dimensional barcode encoding an applicator lot number corresponding to analyte sensory kit box 398 and a sensor serial number corresponding to sensor 375 of analyte sensor system 308 in a single string. Accordingly, upon scanning identification tag 397, identification tag scanner 383 can be configured to retrieve the applicator lot number and the sensor serial number in a single string. An example is described below for illustrative purposes only.

In some embodiments, the applicator lot number can comprise a string of numbers without letters and can be stored as an unsigned 32-bit number (U32). Utilization of U32 provides $2^{32}$ (4,294,967,296) possible unique applicator lot numbers. An example of such an applicator lot number can be 151110428. In other embodiments, the applicator lot number can comprise another combination of numbers, letters and/or other symbols.

In some embodiments, the sensor serial number can comprise an 8-digit portion of the sensor's Universal Fixture serial number and a character (e.g., A-H) indicating a starting position within the full Universal Fixture serial number at which the 8-digit sensor serial number begins. The 8-digit sensor Universal Fixture serial number and the character can be encoded together in an unsigned 32-bit number (u32), wherein the least significant 24 bits (LSB) of the U32 specify the 8-digit sensor serial number and the most significant 8 bits (MSB) of the U32 specify the universal fixture position-indicating character, for example, in ASCII format. An example of such a sensor serial number can be 700958B. In other embodiments, the sensor serial number can comprise another combination of numbers, letters and/or other symbols.

Thus, utilizing the above example applicator lot number and sensor serial number, barcode 397 can be configured to encode the following single string: 151110428700958B, where bold and underlines are used for clarity purposes only. When scanned by identification tag scanner 383, identification tag 397 would then provide the following three pieces of information: [Applicator Lot Number] [6-digit Serial Number] [Universal Fixture Position Character] as [151110428] [700958] [B], where the applicator lot number 151110428 is directly encoded as a U32, the sensor universal fixture serial number and position are separately encoded as 700958 decimal=0x0AB21E hex and ASCII "B"=86 decimal=0x42 hex, and then recombined and/or concatenated (MSB to LSB), indicated in U32 as: [8][24]=[ASCII B=86] [700958]=1107997214 ($66*2^{24}$+700958); and indicated in Hex as: [8] [24]=[0x42][0x0A][0xB2][0x1E]= 0x420AB21E.

An example use of the single 0x7A NFC command for transmitting sensor calibration data from factory calibration station 381 to analyte sensor system 308, utilizing NFC controller 384 and an NFC antenna and/or transmitter circuitry within transmitter 360, respectively, will now be described.

In some embodiments, factory calibration station 381 can cause the sensor calibration data to be written to storage 365 of analyte sensor system 308 utilizing a single NFC command 0x7A, where the sensor calibration data comprises the following parameters: an initial slope (m0) of sensor 375, a final slope (mf) of sensor 375, an applicator lot number associated with analyte sensor kit box 398, e.g., as described above, a sensor serial number for sensor 375, e.g., as described above, and a sensor calibration check date (cc). This sensor calibration data can be transmitted to analyte sensor system 308 in 20 bytes, as provided by the NFC command 0x7A, according to the following table.

TABLE 1

| Byte | Opcode 0x7A Definition | Factory Calibration Station 381 Definition | Transmitter storage 365 location |
|---|---|---|---|
| 0-3 | Sensor m0 (float) | Sensor Initial Slope m0 (float) | Transmitter Database |
| 4-7 | Sensor mf (float) | Sensor Final Slope mf (float) | Transmitter Database |
| 8-11 | Sensor Data | Applicator Lot No. (u32) | UICR Memory (rewritable) |
| 12-15 | | Sensor Serial No. (u32) | UICR Memory (rewritable) |
| 16-19 | | Sensor CalCheck Date (u32) | UICR Memory (rewritable) |

Sensor initial slope (m0) can be read from sensor calibration database 392, for example, indexed by the applicator lot number and sensor serial number read from identification tag 397. Sensor initial slope (m0) can have units of picoamperes per milligram per deciliter (pA/mg/dL) and can be programmed in a transmitter database within storage 365 via command 0x7A as a floating-point number (float) using 4 bytes (bytes 0-3), in some embodiments without encoding. Once written, this value is non-volatile and can remain in the transmitter database of storage 365 until rewritten or until the transmitter database is erased.

Sensor final slope (mf) can be read from sensor calibration database 392, for example, indexed by the applicator lot number and sensor serial number read from identification tag 397. Sensor final slope (mf) can have units of pA/mg/dL and can be programmed in the transmitter database within storage 365 via command 0x7A as a floating-point number (float) using 4 bytes (bytes 4-7), in some embodiments without encoding. Once written, this value is non-volatile and will remain in the transmitter database of storage 365 until rewritten or until the transmitter database is erased.

As previously described, the applicator lot number can have been encoded in identification tag 397 and can be programmed in user information configuration registers (UICR) memory within storage 365 via command 0x7A as an unsigned 32-bit number (u32) using 4 bytes (bytes 8-11), as previously encoded. Once written, this value is non-volatile and can remain in the transmitter UICR memory of storage 365 until rewritten or until the transmitter UICR memory is erased or reflashed.

As previously described, the sensor serial number may have been encoded in identification tag 397 and can be programmed in the user information configuration registers (UICR) memory within storage 365 via command 0x7A as an unsigned 32-bit number (u32) using 4 bytes (bytes 12-15), as previously encoded. Once written, this value is non-volatile and can remain in the transmitter UICR memory of storage 365 until rewritten or until the transmitter UICR memory is erased or reflashed.

Sensor calibration Check date (cc) can be read from sensor calibration database 392, for example, indexed by the applicator lot number and sensor serial number read from identification tag 397. Sensor calcheck date (cc) can be the UTC timestamp at which the sensor CalCheck was performed and can be programmed in the user information configuration registers (UICR) memory within storage 365 via command 0x7A as an unsigned 32-bit number (u32) using 4 bytes (bytes 16-19), as previously encoded. Once written, this value is non-volatile and can remain in the transmitter UICR memory of storage 365 until rewritten or until the transmitter UICR memory is erased or reflashed.

Figure 5:
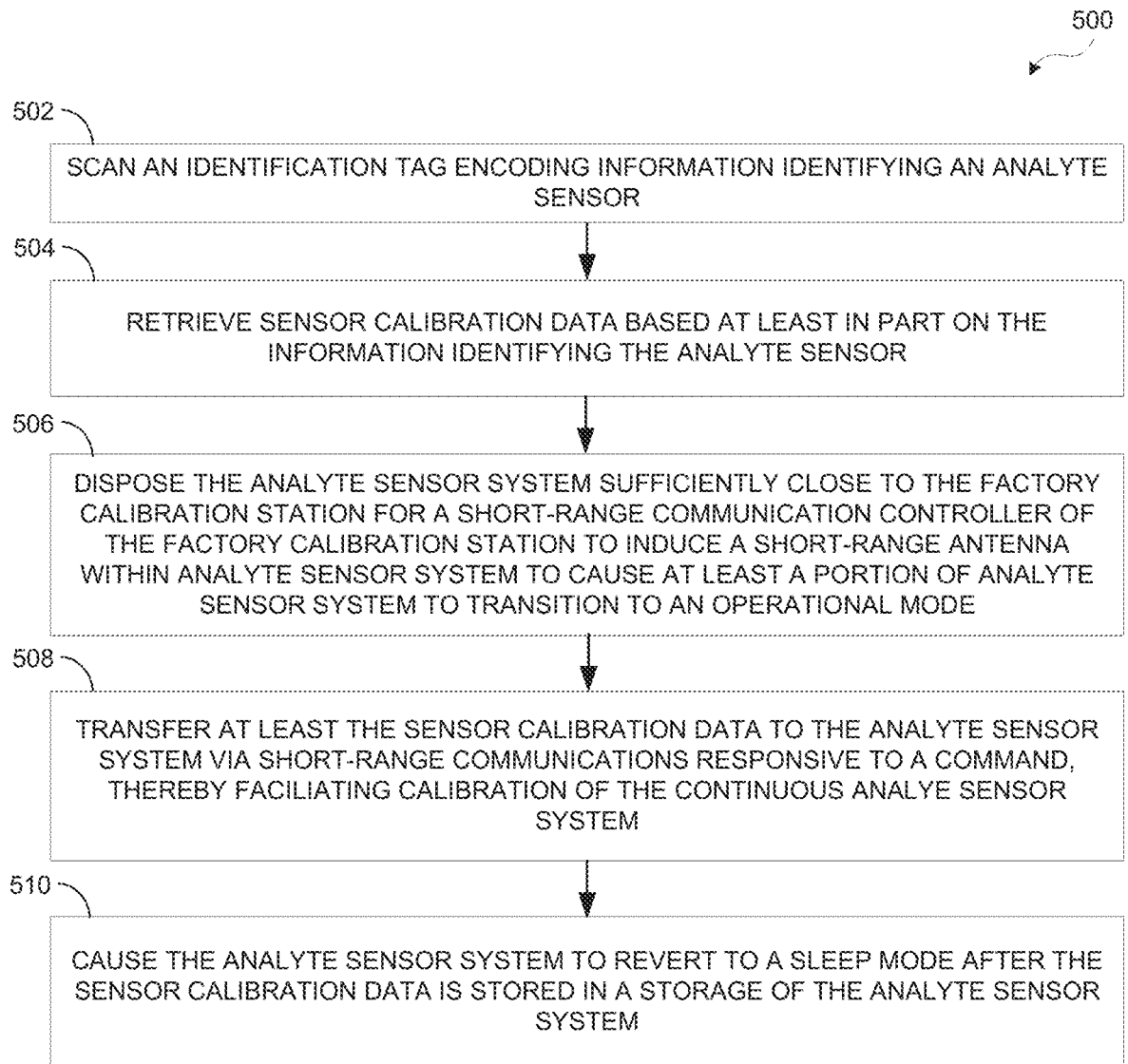
FIG. 5 is an operational flow diagram illustrating various operations that can be performed in accordance with embodiments of the disclosure.

A method 500 for calibrating an analyte sensor directed to the above-described factory calibration (e.g., FIG. 3D) will now be described in connection with FIG. 5 below.

At operation 502, method 500 includes scanning an identification tag encoding information identifying an analyte sensor. For example, factory calibration station 381 can scan identification tag 397 of analyte sensor kit box 398, utilizing identification tag scanner 383. As previously described, identification tag 397 can be a 2-dimensional (2D) barcode encoding at least an applicator lot number and a sensor serial number corresponding to analyte sensor system in a single string.

At operation 504, method 500 includes retrieving sensor calibration data based at least in part on the information identifying the analyte sensor. For example, factory calibration station 381 can retrieve sensor calibration data specifically corresponding to sensor 375 from sensor calibration database 392. Sensor calibration data can include the initial slope (m0) determined for sensor 375, the final slope (mf) determined for sensor 375 and the date (cc) on which the testing procedure that determined the initial and final slopes of sensor 275 was performed. As previously described, in some embodiments, the initial slope (m0), final slope (mf) and date (cc) for sensor 375 can be indexed in sensor calibration database 392 based on the applicator lot number and sensor serial number corresponding to sensor 375.

At operation 506, method 500 includes disposing the analyte sensor system sufficiently close to the factory calibration station for a short-range communication controller of the factory calibration station to induce a short-range antenna within analyte sensor system to cause at least a portion of analyte sensor system to transition to an operational mode. For example, moving analyte sensor kit box 398 within a predetermined distance (e.g., 10 cm) of factory calibration station 381 can allow a near field communication signal transmitted by NFC controller 384 to induce an NFC antenna within transmitter 360 of analyte sensor system 308 to generate a signal configured to wake at least one of connectivity interface 355, storage 365, sensor measurement circuitry 370, sensor 375, processor 380 and/or real time clock 385 in preparation for receiving sensor calibration data.

At operation 508, method 500 includes transferring at least the sensor calibration data to the analyte sensor system via short-range communications responsive to a command, thereby facilitating calibration of the continuous analyte sensor system. For example, utilizing NFC, factory calibration station 381 can utilize a single 0x7A NFC command to transfer the initial slope (m0), final slope (mf), testing procedure date (cc), applicator lot number and sensor serial number to analyte sensor system 308. This sensor calibration data can be stored in one or more memory locations within analyte sensor system 308, for example, storage 365.

In some embodiments, at operation 510, method 500 can further include causing the analyte sensor system to revert to a sleep mode after the sensor calibration data is stored in a storage of the analyte sensor system. For example, in some embodiments factory calibration station 381 can be configured to further send a sleep command to analyte sensor system 308, for example via NFC controller 384, upon receipt of a confirmation from analyte sensor system 308 that the 0x7A command was successfully completed. In some other embodiments, analyte sensor system 308 can be configured to automatically revert to the sleep mode after the sensor calibration data is stored in the one or more locations within storage 365. Reversion to sleep mode upon storage of the sensor calibration data can minimize or at least substantially reduce power usage of analyte sensor system 308 during and after the factory calibration process, thereby extending useful battery life during subsequent use by a patient.

Figure 3E:
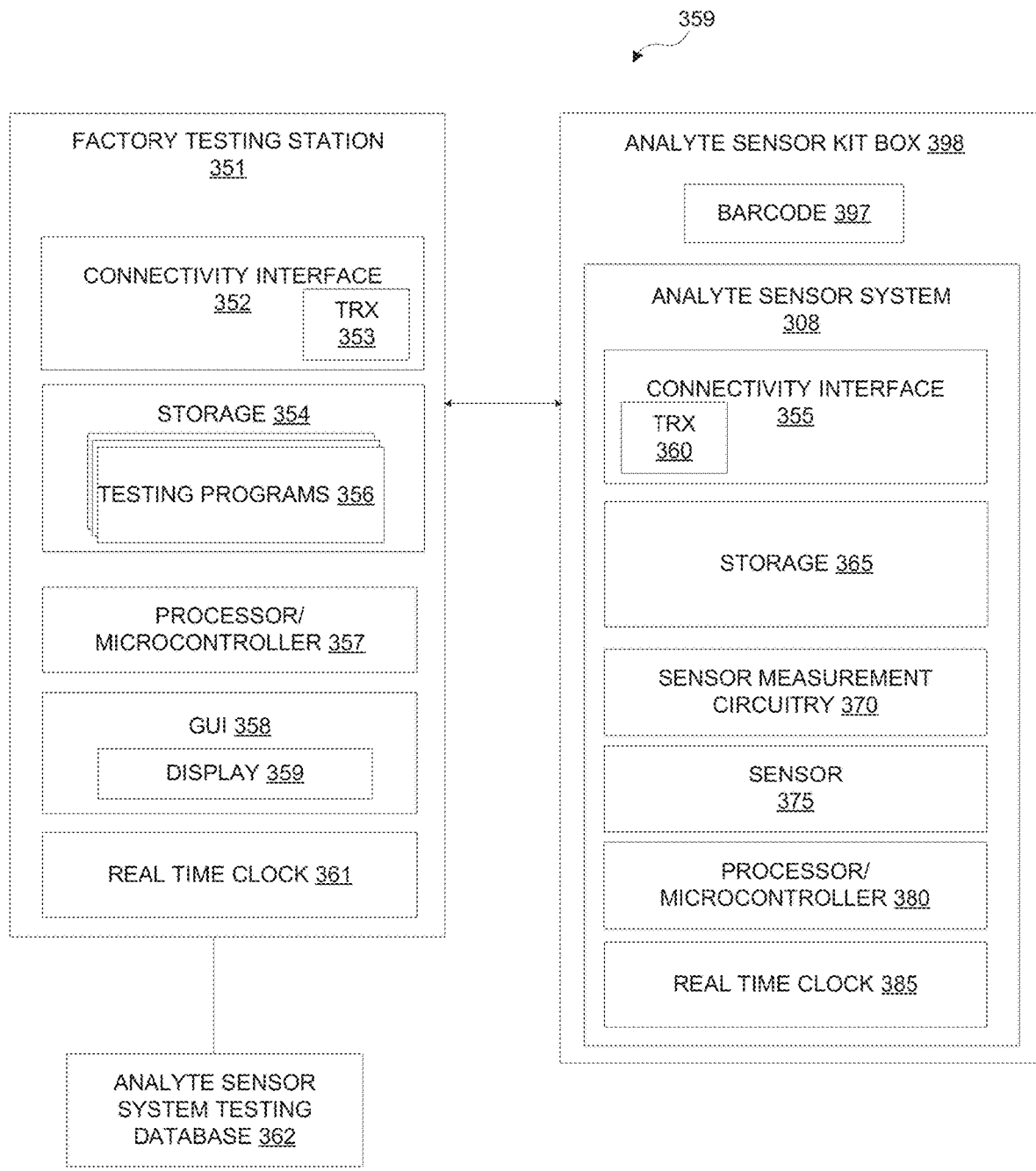
FIG. 3E illustrates aspects of an example factory testing system that can be used in connection with implementing embodiments of the disclosure.

Turning to FIG. 3E, in addition to factory calibration, analyte sensor system 308 can be tested to ensure anticipated operation. Such testing can include communication between a factory testing station 351 and analyte sensor system 308. However, such communication can include advertising, connecting and authenticating processes that take place before any meaningful testing communication is carried out, making for a time-efficient communication process. This problem is compounded when such testing protocols include writing to user information configuration registers (UICRs) within storage 365 of analyte sensor system 308, for example, since such writes can cause analyte sensor system 308 to reboot, which causes the advertising, connecting and authenticating processes to be repeated. In addition, some testing protocols can require communication with connectivity interface 355 and/or transmitter 360 of analyte sensor system 308 directly, at least for conducting some types of field failure analyses. Because such testing can be performed for many analyte sensor systems, in some cases thousands of units or more, it is desirable to streamline the factory testing process. Accordingly, some embodiments described below provide streamlined factory testing of analyte sensor system 308 that avoids the advertising, connecting and authenticating processes at least during portions of such factory testing.

System 359, shown in FIG. 3E, can comprise a factory testing station 351 and analyte sensor system 308. In some embodiments, analyte sensor system 308 can be disposed in analyte sensor kit box 398 as previously described in connection with FIG. 3D. However, the present disclosure is not so limited and analyte sensor system 308 can be tested while outside of analyte sensor kit box 398. In some embodiments, system 359 can additionally comprise an analyte sensor system testing database 357, which can store thereon instructions and/or data that can be retrieved, stored and/or used before, during and/or after one or more factory testing protocols for analyte sensor system 308.

Several components of factory testing station 351, analyte sensor system testing database 357, and analyte sensor system 308 will be described below. However, it should be understood that factory testing station 351, analyte sensor system testing database 357, and analyte sensor system 308 can comprise more, fewer or different components than those discussed.

In the illustrated embodiment, factory testing station 351 includes connectivity interface 352 (which in turn includes transceiver 353), storage 354 (which in turn stores one or more testing programs 356 and/or additional applications), processor/microprocessor 357, real time clock (RTC) 361, and in some cases, a display 359 and a graphical user interface (GUI) 358 that can be presented thereon. A bus (not shown here) can be used to interconnect the various elements of factory testing station 351 and transfer data between these elements.

Storage 354 can also be used for storing an operating system for factory testing station 351 and/or a custom (e.g., proprietary) application designed for wireless data communication between transceiver 360 of analyte sensory system 308 and transceiver 353 of factory testing station 351. Storage 354 can be a single memory device or multiple memory devices and can be a volatile or non-volatile memory for storing data and/or instructions for software programs and applications. The instructions can be executed by processor 357 to control and manage a testing process.

To facilitate prompt wireless communication between factory testing station 351 and analyte sensor system 308, each of transceiver 353 (of factory testing station 351) and transceiver 360 (of analyte sensor system 308) can comprise identical or substantially similarly designed and/or programmed radio chips (e.g., Nordic chips). Utilizing identical or substantially similarly designed and/or programmed radio chips facilitate point-to-point wireless communication between factory testing station 351 and analyte sensor system 308 without using a commercially standardized communication protocol stack, such as BLE. For example, one or more of transceiver 353, connectivity interface 352 and storage 354, and one or more of transceiver 360, connectivity interface 355, and storage 365 can each comprise firmware configured to cause transceivers 353, 360 to send and receive raw packets of data between one another during the factory testing process, which can allow such testing processes to be completed an order of magnitude faster than if a standardized communication protocol, such as BLE and its associated BLE stack, were utilized. Such non-standardized communication can be facilitated by appropriately configuring one or more registers on transceivers 353, 360 directly, without enabling, for example, a BLE stack.

In such embodiments, transceivers 353, 360 can each be preconfigured and/or preprogrammed to communicate (e.g., transmit and/or receive one or more signals) with one another on a same, programmed frequency (e.g., channel) during the testing process. Such preconfiguring eliminates any requirement for negotiating channel selection between transceivers 353, 360. For example, upon waking from a sleep mode, transceiver 360 of analyte sensor system 308 monitors a predetermined frequency channel for a data packet of a predetermined size and format. In such implementations, factory testing station 351 can be the "master" and analyte sensor system 308 can be the "slave" during the testing process. Transceiver 353 is configured to transmit and transceiver 360 is configured to receive a data packet comprising a request (e.g., an opcode) for analyte sensor system 308 to perform one or more tasks or procedures designed to verify anticipated operation of analyte sensor system 308. Upon receipt of the request packet, one or more of transceiver 360, connectivity interface 355, and processor 380 can process the request. Transceiver 360 then transmits and transceiver 353 receives a response returning a result of the request. Upon completion of the testing procedure, transceiver 353 transmits and transceiver 360 receives a message instructing one or more components of analyte sensor system 308 to revert to a sleep mode. In some embodiments, such a message can comprise an "all complete" opcode.

In some embodiments, packet transmission failures and/or collisions can be mitigated by utilizing conventional timeouts and retries. In some embodiments, multiple testing stations can be provided to operate concurrently through the utilization of RF shielding surrounding each testing station comprising a factory testing station and an analyte sensor system under test as described above. In some other embodiments, multiple testing stations can be provided to operate concurrently by pre-configuring and/or preprogramming each analyte sensor system under test to utilize a unique one of a plurality of available frequencies (e.g., channels) for the testing process. In such embodiments, each factory testing station can be configured to sync with or track the particular analyte sensor system(s) being pre-configured and/or pre-programmed to utilize the same frequency during the testing process (e.g., a kHz, MHz or GHz frequency or any frequency suitable for radio-frequency communications).

Figure 6A:
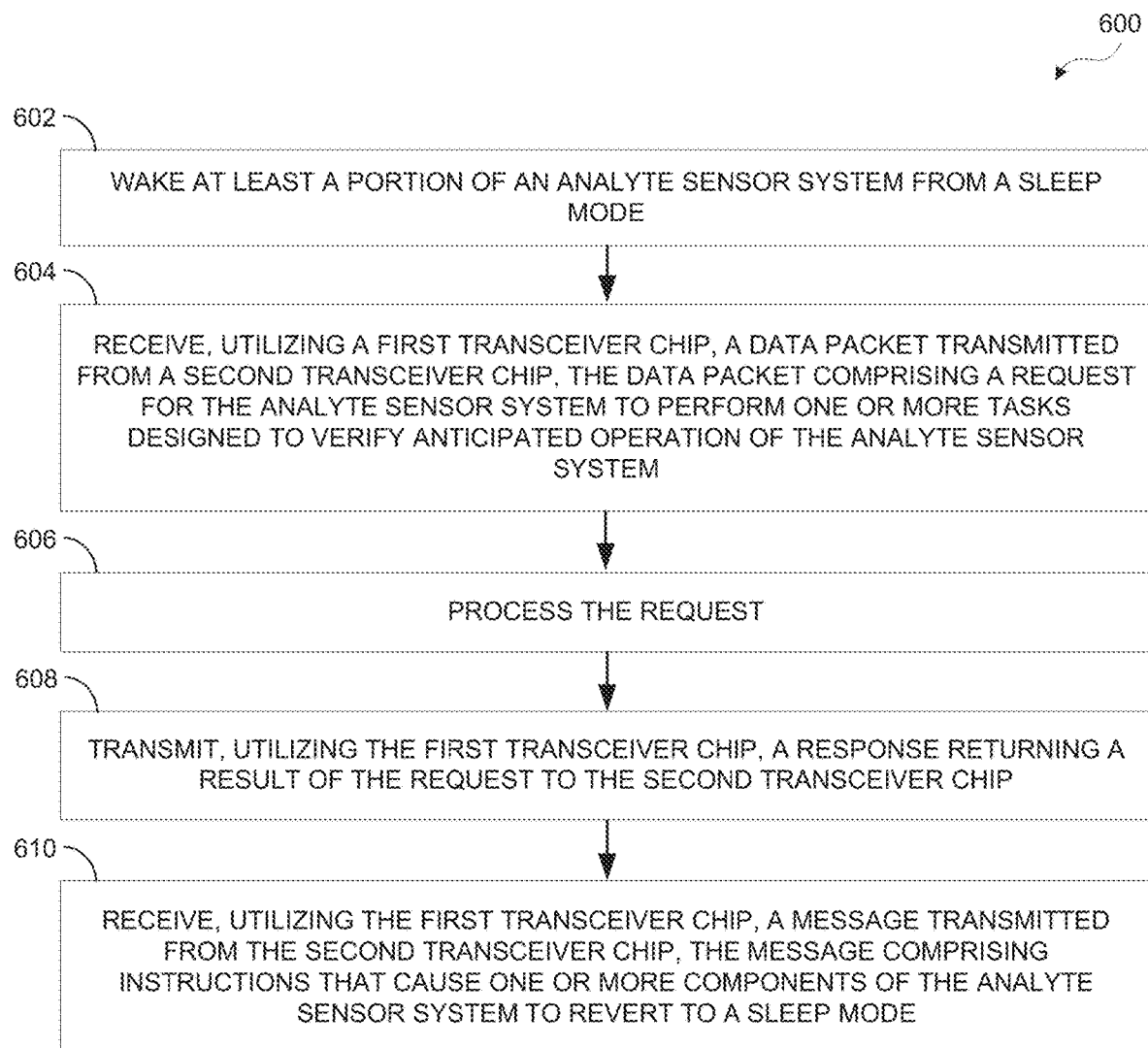
FIG. 6A is an operational flow diagram illustrating various operations that can be performed in accordance with embodiments of the disclosure.
Figure 6B:
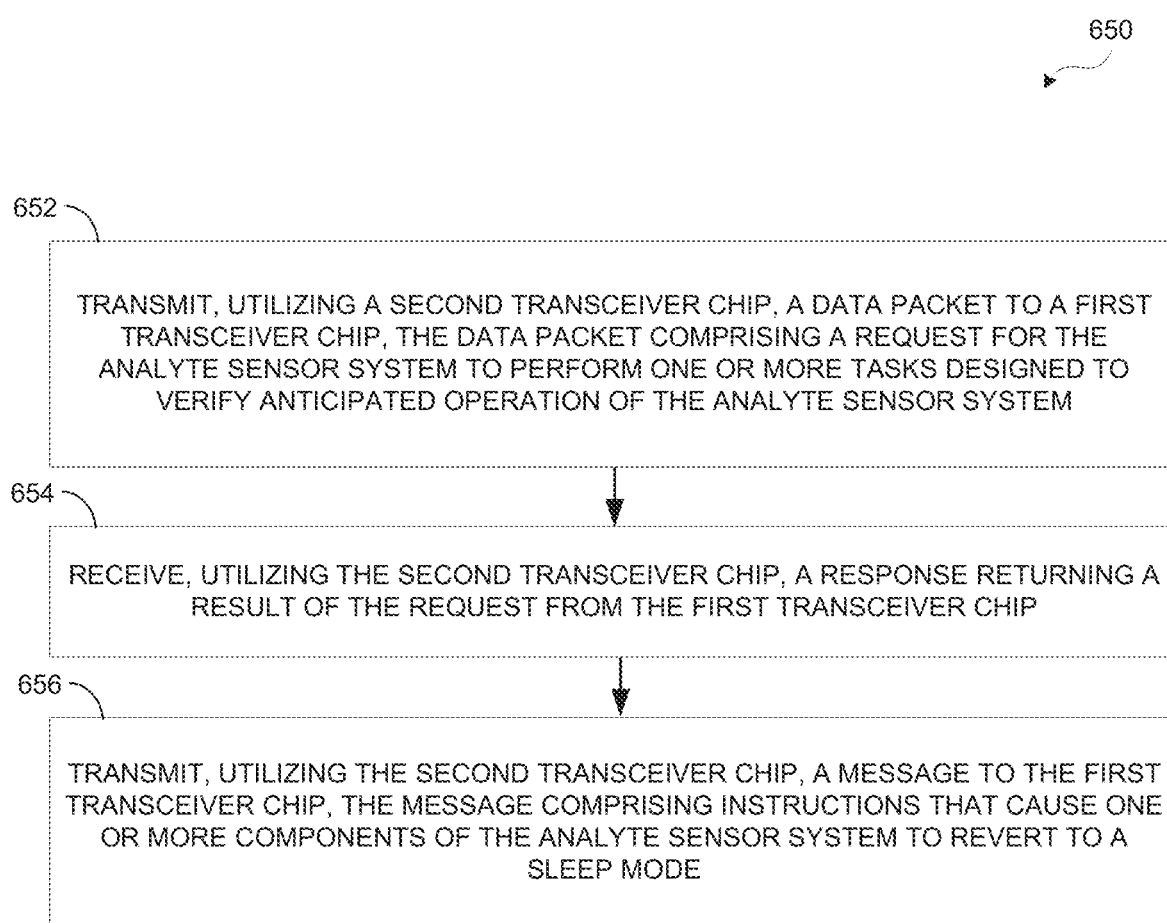
FIG. 6B is an operational flow diagram illustrating various operations that can be performed in accordance with embodiments of the disclosure.

A flowchart 600 for testing an analyte sensor system directed to the above-described factory testing (e.g., FIG. 3E) will now be described in connection with FIG. 6A below. Flowchart 600 can correspond to operations of analyte sensor system 308.

At operation 602, flowchart 600 includes waking at least a portion of an analyte sensor system from a sleep mode. For example, analyte sensor system 308 can be configured to wake from a power-saving shelf- or sleep-mode in response to an initiation of a testing procedure.

At operation 604, flowchart 600 includes receiving, utilizing a first transceiver chip, a data packet transmitted from a second transceiver chip, the data packet comprising a request for the analyte sensor system to perform one or more tasks designed to verify anticipated operation of the analyte sensor system. For example, transceiver 353 of factory testing station 351 is configured to transmit and transceiver 360 of analyte sensor system 308 is configured to receive a data packet comprising a request (e.g., an opcode) for analyte sensor system 308 to perform one or more tasks or procedures designed to verify anticipated operation of analyte sensor system 308. Transceivers 353, 360 can comprise identical or substantially similar transceiver chips (e.g., Nordic chips).

At operation 606, flowchart 600 includes processing the request. For example, upon receipt of the request packet, one or more of transceiver 360, connectivity interface 355, and processor 380 of analyte sensor system 308 can process the request.

At operation 608, flowchart 600 includes transmitting, utilizing the first transceiver chip, a response returning a result of the request to the second transceiver chip. For example, transceiver 360 of analyte sensor system 308 can transmit and transceiver 353 of factory testing station 351 can receive a response returning a result of the request.

At operation 610, flowchart 600 includes receiving, utilizing the first transceiver chip, a message transmitted from the second transceiver chip, the message comprising instructions that cause one or more components of the analyte sensor system to revert to a sleep mode. For example, transceiver 353 of factory testing station 351 can transmit and transceiver 360 of analyte sensor system 308 can receive a message comprising instructions that cause one or more components of analyte sensor system 308 to revert to a sleep mode. In some embodiments, such a message can comprise an "all complete" opcode.

A flowchart 650 for testing an analyte sensor system directed to the above-described factory testing (e.g., FIG. 3E) will now be described in connection with FIG. 6A below. Flowchart 650 can correspond to operations of factory testing station 351.

At operation 652, flowchart 650 includes transmitting to a first transceiver chip, utilizing a second transceiver chip, a data packet comprising a request for the analyte sensor system to perform one or more tasks designed to verify anticipated operation of the analyte sensor system. For example, transceiver 353 of factory testing station 351 is configured to transmit and transceiver 360 of analyte sensor system 308 is configured to receive a data packet comprising a request (e.g., an opcode) for analyte sensor system 308 to perform one or more tasks or procedures designed to verify anticipated operation of analyte sensor system 308. Transceivers 353, 360 can comprise identical or substantially similar transceiver chips.

At operation 654, flowchart 650 includes receiving, utilizing the second transceiver chip, a response returning a result of the request from the first transceiver chip. For example, transceiver 360 of analyte sensor system 308 can transmit and transceiver 353 of factory testing station 351 can receive a response returning a result of the request.

At operation 656, flowchart 650 includes transmitting, utilizing the second transceiver chip, a message to the first transceiver chip, the message comprising instructions that cause one or more components of the analyte sensor system to revert to a sleep mode. For example, transceiver 353 of factory testing station 351 can transmit and transceiver 360 of analyte sensor system 308 can receive a message comprising instructions that cause one or more components of analyte sensor system 308 to revert to a sleep mode. In some embodiments, such a message can comprise an "all complete" opcode.

Analyte Sensor System Low-Power, Sleep and/or Shelf Mode and Wake Circuitry

Figure 4:
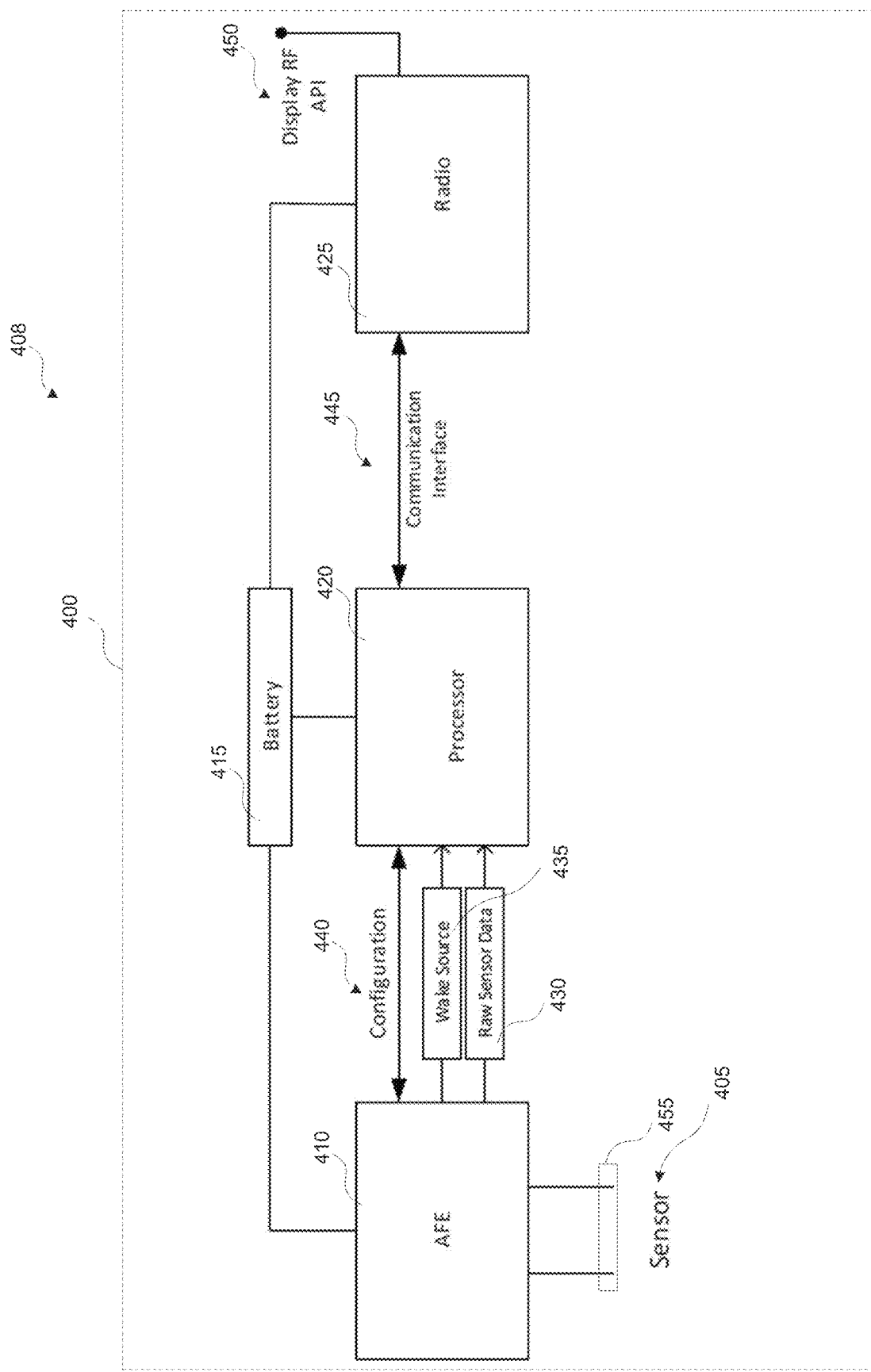
FIG. 4 is a block diagram illustrating aspects of an example analyte sensor system according to embodiments of the disclosure.

FIG. 4 is a block diagram illustrating potential aspects of analyte sensor system 408 according to embodiments of the present disclosure. Analyte sensor system 408 can correspond to analyte sensor system 308 of FIG. 3B in some embodiments. The aspects of analyte sensor system 408 shown in FIG. 4 can be implemented within subsystem 400 of analyte sensor system 408 and can in general be used to manage a radio interface between analyte sensor system 408 and any display devices communicatively coupled thereto via one or more wireless protocol(s), such as BLE, Wi-Fi, cellular and/or NFC. For example, application programming interface (API) 450 can be provided for display devices to communicate with processor 420 (e.g., processor 380) via radio 425, which can include a BLE or another RF or microwave transceiver (e.g., transceiver 360). Processor 420 can be used to process analyte data gathered by sensor 405 (e.g., sensor 375).

As shown, within analyte sensor system 408, subsystem 400 can include sensor 405 (e.g., sensor 10), analog front end (AFE) 410 (e.g., sensor electronics module 12), battery 415, processor 420, and radio 425. The design of analyte sensor system 408, including with respect to subsystem 400 as well as related software, enables multi-chip operation and management, and particularly where such operation and/or management is carried out in accordance with power savings principles described herein and can involve implementing system configurations that support/maximize power savings. For example, the design enables system startup, inter-chip communication, application task scheduling, maximization of battery life in storage as well as active modes, and utilization of control points and indications by API 450 associated with radio 425.

Analyte sensor system 408 can be in a storage mode before analyte sensor system 408 has been inserted into a host. In storage mode, radio 425 can be at least partially disabled in order to save power. Likewise, processor 420 can be at least partially disabled, for example by disabling a clock used by processor 420 (e.g., RTC 350). Furthermore, it is contemplated that, in the storage mode, radio 425 can be configured to be in a deep sleep mode. This can advantageously extend/maximize the battery life of analyte sensor system 408. In some embodiments, upon interacting with display device 310, for example via NFC or visible light modulating and emitting protocols, analyte sensor system 408 can exit the storage mode. In some embodiments, upon detecting that sensor 405 has been inserted into the host, analyte sensor system 408 can automatically exit storage mode and enter an active mode.

For example, in some embodiments, during such a storage mode (e.g., a shelf mode) AFE 410 can comprise an ASIC configured to wake periodically (e.g., every 64 seconds), take an analyte current reading from sensor 405 and, if that reading is greater than a predetermined threshold (e.g., configured during manufacturing), send a signal (e.g., wake source 435) to processor 420, waking processor 420, which can then perform a secondary sensor confirmation check. In some embodiments, such a predetermined threshold can be determined from a mean break in current of sensor 405 during hydration and electrochemical normalization that occurs after insertion of sensor 405 into the host (e.g., 20 nA). If the secondary sensor confirmation check passes, analyte sensor system 408 can be capable of determining that it has been deployed and begin a connection process with one or more display devices. However, if the analyte current reading from sensor 405 is not greater than the predetermined threshold, AFE 410 can revert to the sleep mode until the next wake period (e.g., 64 seconds after the preceding wake period) when the procedure can be repeated.

However, a time period between opening a box including analyte sensor system 408 and beginning such a connection process is not deterministic, as it can be affected by many factors including, but not limited to, a time taken to insert sensor 405 into the host, and a time taken for sensor 405 to properly hydrate once inserted into the host (which can vary from host to host). Variability in these and other relevant factors can impair the user's experience as a result of unclear timelines associated with the process. In addition, because the trigger for exiting storage mode is a measured analyte current reading from sensor 405 exceeding a predetermined threshold, static discharge to sensor 405 and/or AFE 410 can undesirably trigger a false positive for exiting storage mode, increasing the risk of battery 415 being partially or fully depleted by the time of actual deployment by a host. Accordingly, it may be desirable to provide a more defined sequence for initially exiting a storage or shelf mode that is less susceptible to timeline variabilities and false wake-ups as described above.

Accordingly, in some embodiments, at the time of manufacture and/or factory packaging, a shorting element 455 can be disposed in electrical contact with each terminal of sensor 405 such that the terminals are electrically short-circuited. In some embodiments, shorting element 455 can comprise an electrically conductive wire or electrically conductive sheet. In some embodiments, shorting element 455 comprises molded or stamped low-resistance and/or electrically conductive foam configured to electrically short both terminals of sensor 405 while sensor 405 is disposed in its packaging, including the low-resistance and/or electrically conductive foam. After disposing shorting element 455 across the terminals of sensor 405, analyte sensor system 408 can be placed in storage or shelf mode during which AFE 410 is configured to wake periodically (e.g., every 64 seconds) and take an analyte current reading from sensor 405.

However, contrary to the above-described embodiments, where an analyte current reading from sensor 405 exceeding the predetermined threshold triggers an exit of storage mode, here, a measured analyte current reading from sensor 405 falling below a different predetermined threshold triggers an exit of storage mode. For example, while shorting element 455 shorts the terminals of sensor 405, a measured analyte current reading from sensor 405 will be maximal or near maximal. When the shorting element 455 is removed from the terminals of sensor 405, a measured analyte current reading from sensor 405 will be zero, or near zero, signaling that sensor 405 has been removed from its packaging and is likely in use. Upon exiting storage mode, analyte sensor system 408 can be configured to immediately begin a Bluetooth or BLE pairing operation, or another wireless communication protocol pairing operation, to establish a connection with at least one display device as will be described in more detail in connection with one or more embodiments below. In such embodiments, a secondary sensor check may not be required. After a successful pairing analyte sensor system 408 can monitor the analyte current reading from sensor 405 for signal characteristics indicative of sensor break-in and/or hydration to confirm the analyte sensor system 408 is properly mounted to a body-worn receptacle.

Embodiments utilizing such a shorting element 455 provide at least a few additional benefits. For example, a time interval required for pairing is reduced since the act of removing the shorting element 455 provides a deterministic time from which the process begins and analyte sensor system 408 need not wait for sensor hydration or break-in. In addition, static discharge no longer presents a risk for false wake up, since the trigger is an analyte current reading from sensor 405 that is lower than a predetermined value, rather than an analyte current reading from sensor 405 that is higher than the same or another predetermined value. In some embodiments, a light emitting diode (LED) disposed within analyte sensor system 408 (not shown) can be configured to blink or illuminate steadily when analyte sensor system 408 has entered the Bluetooth pairing operation, providing further confirmation to a user that the system is working as expected. Alternatively, a notification may be displayed on a display device, e.g., display device 310, to indicate that analyte sensor system 408 has entered the Bluetooth pairing operation.

In active mode, a low power mode (LPM) can still be used (e.g., to extend/maximize battery life), but RTC 350 can be activated/enabled. This can allow processor 420 to track time accurately and perform other clock-based functions while still allowing for power savings. For example, RTC 350 can be used to perform error recovery using time-based counters and interrupts. The following error recovery scenarios are provided by way of illustration. In one example, if no response messages are received from radio 425 for a given amount of time, processor 420 can reset radio 425. In another example, a periodic interrupt can be used where if logic of RTC 350 fails, analyte sensor system 408 can be reset by hardware logic. In additional implementations, if a message or signal associated with wake source 435 (or AFE 410) is not received or fails, an interrupt (e.g., RTC interrupt) can be used to bring processor 420 out of LPM and perform communication functions.

Processor 420 can act as a system controller for subsystem 400 within analyte sensor system 408. For example, after initializing, radio 425 can enter a sleep state and wait for instruction from processor 420. AFE 410 can initialize to a default state and likewise wait for configuration instructions/commands from processor 420. Processor 420 can control resetting AFE 410 and/or radio 425 in case errors are detected. Processor 420 can also self-reset if internal error conditions are detected (e.g., using a hardware watchdog).

Subsystem 400 of analyte sensor system 8 can utilize a multi-chip (or multi-module) design, in which case a hardware communication bus can be used for the exchange of data among the various chips (or modules). Examples of viable options for the hardware communication bus include Inter-Integrated Circuit (I2C or I2C) and Serial Peripheral Interface (SPI). SPI can be used to achieve a reduction in powers as well as an increase in speed relative to I2C.

Wake source 435 and raw sensor data 430 can be used to maximize the battery life of analyte sensor system 408. AFE 410 can typically be used as a wake source for components of subsystem 400. Nevertheless, other wake sources can be utilized. During normal operation, AFE 410 can allow processor 420 to enter an energy efficient lower power mode (LPM). Wake source 435 can be used to signal processor 420 to exit LPM such that, e.g., processor 420 can execute operations not typically available during LPM. Wake source 435 can signal processor 420 in this manner periodically and trigger processor 420 to start processing or executing operations. Analyte sensor system 408 can include multiple processors, and staged task processing can be implemented, in some cases in connection with wake source 435, such that not all processors are active simultaneously. This technique can reduce power consumption and hence extend battery life. By way of example, wake source 435 can cause first signal processor 420 to exit LPM and begin configuring the pertinent hardware and software of analyte sensor system 408 to initiate the transfer of raw sensor (analyte) data from AFE 410.

Raw sensor data 430 can include hardware that transfers sensor data gathered by sensor 405 from AFE 410 to processor 420. Such data can be referred to herein as raw sensor data or raw analyte data. Configuration 440 can be a two-way interface between processor 420 and AFE 410. In some cases, configuration 440 can be implemented using I2C, but SPI or another interface configuration can also be used. Processor 420 and radio 425 can likewise use a SPI and/or I2C bus for communication and data transfer. In some cases, additional hardware and software can be used to create an asynchronous interface between processor 420 and radio 425 when using synchronous protocols (e.g., SPI and the like).

AFE 410 can sample raw analyte data from sensor 405 for a period of time (e.g., 7 minutes). During the sampling, processor 420 and a processor (e.g., baseband processor) within radio 425 can be held in low power mode (LPM). Once AFE 410 completes the sample, AFE 410 can send a signal to processor 420 indicating that processor 420 should exit LPM (i.e., should wake up). AFE 410 can then transfer the raw analyte data to processor 420 via configuration 440. AFE 410 can then re-enter LPM. Processor 420 can then process the raw analyte data (e.g., to generate an estimated glucose value) and store the processed analyte data. Processor 420 can then signal the processor of radio 425 via communication interface 445 to communicate the processed analyte data to radio 425. Processor 420 can subsequently enter LPM while waiting for radio 425 to connect to a display device (e.g., display device 310). Once such a connection is made, processor 420 can exit LPM, and the display device and processor 420 can exchange data, commands, and/or messaging via radio 425.

API 450 can be used to interface with devices remote from analyte sensor system 408 over various wireless protocols. One example of such a protocol is BLE. In this regard, API 450 can allow analyte sensor system 408 to be configured by a user of a display device (e.g., display device 310) running an application such as, for example, analyte sensor application 330. Analyte sensor application 330 can have been developed by the manufacturer of analyte sensor system 408 and/or display device 310 or can be developed by any individual or entity. In the case that the BLE standard is used to couple a display device to analyte sensor system 408, BLE Characteristics can be configurable according to system design parameters.

With the above description of aspects of systems and methods for wireless communication of analyte data, a number of specific and further improvements will now be provided. It will be appreciated by one of skill in the art upon studying the present disclosure that these improvements can be implemented using features and combinations of features of the example configurations described above, whether or not explicit reference is made to the same.

Authentication and Pairing

In scenarios involving the connection of two devices over a network (wireless or otherwise), authentication and pairing can be used to prevent unauthorized devices from making a connection. For example, where sensitive data is being exchanged (e.g., personal analyte concentration data), authentication can be used to prevent unauthorized devices or entities from gaining access to the data. In this regard, authentication and pairing protocols can be employed to establish or validate the identity of connecting devices. However, securely pairing an analyte sensor system, such as system 308, with a peripheral device, such as display device 310, can be challenging for users. Accordingly, several embodiments for automatically pairing such analyte sensor systems to one or more display devices with minimal user input are described below in connection with FIGS. 7-8B and 9-10B, respectively.

Figure 7:
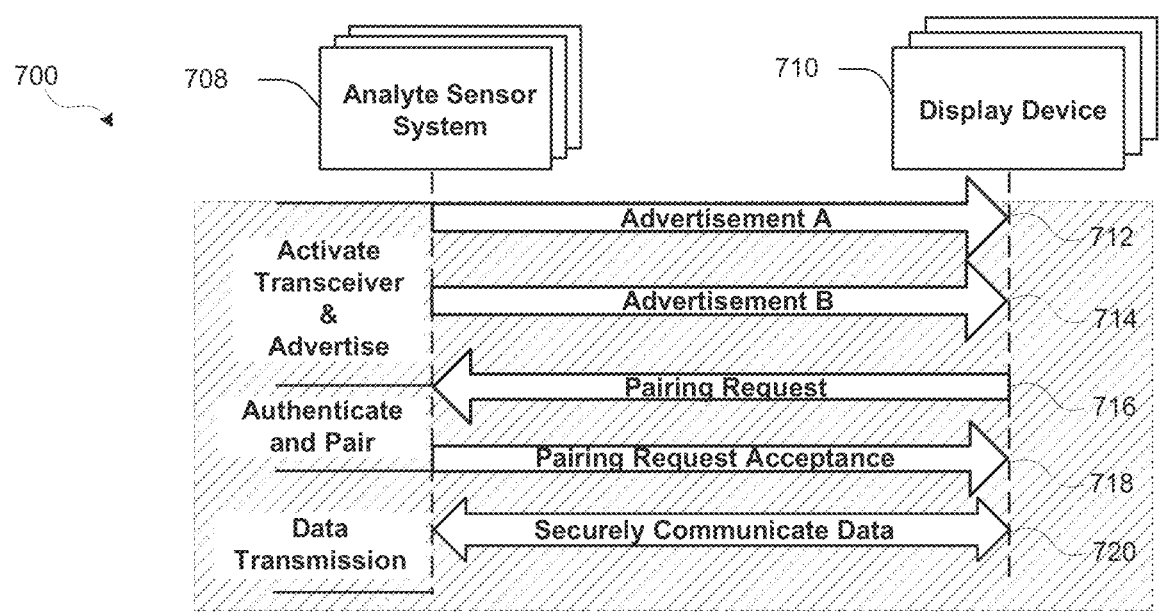
FIG. 7 is a signaling diagram illustrating various operations that can be performed in accordance with embodiments of the disclosure.
Figure 8B:
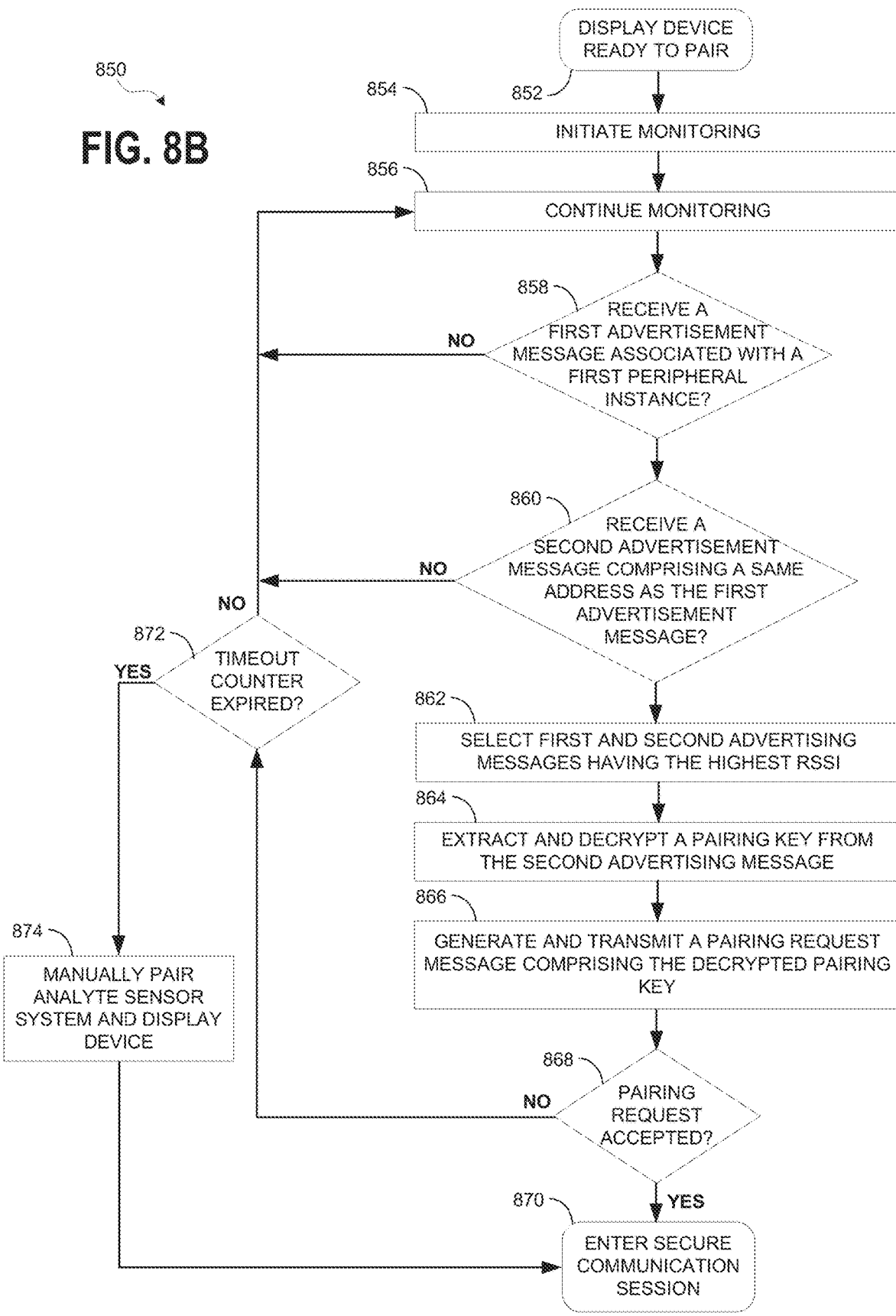
FIG. 8B is an operational flow diagram illustrating various operations that can be performed in accordance with embodiments of the disclosure.

FIG. 7 illustrates a messaging diagram of a pairing operation between one or more analyte sensor system(s) 708 and one or more display devices 710, according to some example embodiments. In some embodiments, an analyte sensor system 708 and display device(s) 710 may correspond to analyte sensor system 308 and any of display devices 310, respectively, as previously described in connection with FIGS. 3A-3E. FIG. 8A is a flowchart 800, illustrating various operations that can be performed in accordance with embodiments of the disclosure. In some embodiments, flowchart 800 of FIG. 8A corresponds to operations and/or actions performed by analyte sensor system 708 of FIG. 7. FIG. 8B is a flowchart 850 illustrating various operations that can be performed in accordance with embodiments of the disclosure. In some embodiments, flowchart 850 of FIG. 8B corresponds to operations and/or actions performed by display device (s) 710 of FIG. 7.

The various tasks performed in connection with the procedures illustrated in FIGS. 7-8B can be performed, for example, by respective processors executing instructions embodied in respective non-transitory computer-readable media. The tasks or operations performed in connection with the procedures can be performed by hardware, software, firmware, or any combination thereof incorporated into one or more of computing devices. It will be appreciated upon studying the present disclosure that such procedures can include any number of additional or alternative tasks or operations. The operations shown by way of example in FIGS. 8A-8B need not be performed in the illustrated order, and the procedures can be incorporated into more comprehensive procedures or processes having additional functionality not described in detail herein with specific reference to FIGS. 8A-8B.

An example pairing operation will now be described in connection with FIG. 7. In some embodiments, before the operations described below, a user can download, for example from an app store, and/or otherwise initialize an application for monitoring an analyte concentration of the user to display device 710. The user can complete a setup of the application, after which the application can instruct the user to deploy analyte sensor system 708 in preparation of a pairing operation between analyte sensor system 708 and display device 710. The application running on display device 710 can then begin monitoring for advertisement messages, e.g., BLE advertisement messages. Upon deployment, analyte sensor system 708 can be configured to wake up from a lower power or sleep mode, for example, as previously described in connection with FIG. 4.

Upon waking, analyte sensor system 708 can be configured to generate a random pairing key. Two concurrent advertisement messages (e.g., advertisement message A 712 and advertisement message B 714) can be generated and a radio of analyte sensor system 708 can transmit the two concurrent advertisement messages. In some embodiments, first advertisement message 712 can include one or more of the following: an indication of a manufacturer of analyte sensor system 708 (e.g., Dexcom), an address identifying analyte sensor system 708 (e.g., a BLE address stored internally to a radio chip of analyte sensor system 708 that identifies analyte sensor system 708 and/or the radio chip), an indication that a device or peripheral instance associated with advertisement message 712 is connectable, and an indication of out-of-band (OOB) authentication. In some embodiments, a peripheral instance can be considered a software-based object corresponding to a particular communication device, e.g., display device 710. In some embodiments, an indication of OOB authentication may indicate that one or more additional messages will be transmitted to authenticate the connection. In some embodiments, second advertisement message 714 can include one or more of the following: the indication of the manufacturer of analyte sensor system 708 (e.g., Dexcom), the address identifying analyte sensor system 708 (e.g., the BLE address stored internally to the radio chip of analyte sensor system 708), an indication that a device or peripheral instance associated with advertisement message 714 is not connectable, and a payload comprising the random pairing key. The address included in each of first and second advertisement messages 712, 714 can be identical to one another. In some embodiments, the random pairing key can be encrypted before being inserted into and transmitted within advertisement message 714. In some embodiments, in addition or in alterative to being encrypted, the random pairing key can be further obscured by disposing nibbles and/or subsets of the random pairing key in a proprietary pattern within the payload of advertisement message 714. In such embodiments, display device 710 can be configured to decrypt and/or reconstruct the nibbles and/or subsets of the random pairing key based, for example, based on display device 710 having and/or obtaining a priori programming and/or instructions configured to perform such decryption and/or reconstruction. In one example, such a priori programming and/or instructions can be downloaded from a server (add that it may use transmitter id to determine what to pull from the server etc.)

Based on the monitoring, display device 710 can be configured to detect each of first and second advertisement messages 712, 714. Display device 710 can be configured to determine that first and second advertisement messages 712, 714 are valid based at least in part on each message 712, 714 indicating the same manufacturer (e.g., Dexcom) and/or based at least in part on each message 712, 714 indicating the same address (e.g., identifying analyte sensor system 708). In some embodiments, where display device 710 detects more than one valid pair of messages fitting the description of first and second advertisement messages 712, 714, display device 710 can be configured to select the pair of valid messages having the highest received signal strength indicator (RSSI). For example, each of advertising messages 712, 714 would be expected to have substantially similar RSSI values, since both messages are transmitted from the same device in sufficiently close temporal proximity to one another.

Display device 710 can be further configured to extract and decrypt the random pairing key from second advertisement message 714. Display device 710 can be configured to generate and transmit a pairing request 716, addressed to analyte sensor system 708 as indicated by the address in first advertisement message 712, and further comprising the decrypted random pairing key.

Analyte sensor system 708 can receive pairing request 716 and determine whether the decrypted random pairing key within pairing request 716 is the same as the random pairing key analyte sensor system 708 originally generated, encrypted and transmitted within second advertising message 714. If the decrypted random pairing key is the same, analyte sensor system 708 can generate and transmit a pairing request acceptance message 718 to display device 710. Analyte sensor system 708 and display device 710 can then enter a secure sensor communication session. In some embodiments, if the decrypted random pairing key is not the same as the random pairing key analyte sensor system 708 originally generated, encrypted and transmitted within second advertising message 714, analyte sensor system 708 can ignore pairing request 716.

Description now turns to flowchart 800 of FIG. 8A, describing operations of, for example, analyte sensor system 708. Block 802 includes waking analyte sensor system 708. For example, analyte sensor system 708 can wake from a storage mode, a sleep mode, or a low-power mode upon deployment.

Block 804 includes generating and encrypting a pairing key. For example, upon waking, analyte sensor system 708 can be configured to generate a random pairing key for pairing with another device, for example, display device 710. Analyte sensor system 708 can be further configured to encrypt the random pairing key according to any suitable encryption scheme.

Block 806 includes initializing a radio of a transceiver with a first peripheral instance and a second peripheral instance. For example, analyte sensor system 708 can be configured to advertise its availability to pair utilizing two advertisement messages configured to allow automatic authentication and pairing between analyte sensor system 708 and display device 710.

Block 808 includes setting a timeout counter. For example, the pairing process can have a set time interval after which, if pairing has yet to be successful, the pairing process can be determined to have failed. In some embodiments, analyte sensor system 708 can be configured to set an 80-minute timeout counter. However, the present disclosure is not so limited, and any suitable time interval can be utilized.

Block 810 includes generating and transmitting a first advertising message associated with the first peripheral instance and a second advertising message associated with the second peripheral instance. For example, analyte sensor system 708 can be configured to generate first advertisement message 712 comprising an indication of a manufacturer of analyte sensor system 708 (e.g., Dexcom), an address identifying analyte sensor system 708 (e.g., a BLE address stored internally to a radio chip of analyte sensor system 708), an indication that a device or peripheral instance associated with advertisement message 712 is connectable, and an indication of out-of-band (OOB) authentication. Analyte sensor system 708 can also be configured to generate second advertisement message 714 (FIG. 7) comprising the same indication of the manufacturer of analyte sensor system 708 (e.g., Dexcom), the same address identifying analyte sensor system 708 (e.g., the BLE address stored internally to the radio chip of analyte sensor system 708), an indication that a device or peripheral instance associated with advertisement message 714 is not connectable, and a payload comprising the encrypted random pairing key. Analyte sensor system 708 can transmit first and second advertisement messages 712, 714 concurrently, e.g., at the same time, in immediate succession, and/or in the same pairing session.

Block 812 includes determining whether a pairing request corresponding to the first peripheral instance has been received. For example, a device attempting to pair with analyte sensor system 708, e.g., display device 710 can transmit, and analyte sensor system 708 can receive pairing request 716 in response to the transmission of first and second advertisement messages 712, 714. If the determination at block 812 is negative, block 814 includes determining whether the timeout counter has expired. If not, flowchart circles back to block 810. If so, flowchart advances to block 820, where a manual pairing operation can occur between analyte sensor system 708 and display device 710, after which flowchart 800 can enter a secure communication session for securely communicating analyte data at block 822.

If the determination at block 812 is affirmative, flowchart 800 advances to block 816, which includes determining whether the pairing request comprises a valid pairing key. For example, analyte sensor system 708 can be configured to determine whether a decrypted pairing key embedded within pairing request 716 is the same pairing key that analyte sensor system 708 encrypted and transmitted in second advertisement message 714. If the determination at block 816 is negative, flowchart 800 circles back to block 814. If the determination at block 816 is affirmative, flowchart 800 advances to block 818, which includes generating and transmitting a pairing request acceptance message. For example, analyte sensor system 708 can be configured to transmit pairing request acceptance message 718 back to display device 710. Flowchart 800 then advances to block 822, entering a secure communication session for securely communicating analyte data.

Description now turns to flowchart 850 of FIG. 8B, describing operations of, for example, display device(s) 710. At block 852 a display device, for example, display device 710 (FIG. 7) is ready to enter a pairing operation. Block 854 includes initiating monitoring for pairable device(s). For example, display device 710 can be configured to monitor one or more communication channels for one or more messages indicative of a device attempting to pair with display device 710.

Block 856 includes continuing monitoring for the pairable device(s). For example, display device 710 can be configured to continue monitoring the one or more communication channels for the one or more messages indicative of a device attempting to pair with display device 710 for a predetermined time interval.

Block 858 includes determining whether a first advertisement message associated with a first peripheral instance has been received. For example, in some embodiments, display device 710 can be configured to detect and/or identify first advertisement message 712 based at least in part on first advertisement message 712 including any one or more of a certain indication of a manufacturer of analyte sensor system 708 (e.g., Dexcom, Inc., San Diego, CA), an address identifying analyte sensor system 708 (e.g., a BLE address stored internally to a radio chip of analyte sensor system 708), an indication that a device or peripheral instance associated with advertisement message 712 is connectable, and an indication of out-of-band (00B) authentication.

If the determination at block 858 is negative, flowchart 850 can circle back to block 856 and display device 710 continues monitoring. If the determination at block 858 is affirmative, flowchart 850 advances to block 860, which includes determining whether a second advertisement message comprising the same address as the first advertisement has been received. For example, display device 710 can be configured to detect and/or identify second advertisement message 714 based at least in part on second advertisement message 714 including an indication of the same manufacturer as indicated in first advertisement message 712 (e.g., Dexcom) and an indication of the same address as indicated in first advertisement message 712.

If the determination at block 860 is negative, flowchart 850 can circle back to block 856 and display device 710 continues monitoring. In some embodiments, more than one pair of first and second advertisement messages 712, 714 can be received from more than one analyte sensor system. In such embodiments, if the determination at block 860 is affirmative, flowchart 850 advances to block 862, where display device 710 can be configured to select the first and second advertising messages having the highest received signal strength indication (RSSI). Selecting the qualifying advertising message pair with the highest RSSI can facilitate authentication and pairing with the correct analyte sensor system.

Block 864 includes extracting and decrypting a pairing key from the second advertising message. For example, analyte sensor system 708 previously generated, encrypted and embedded a random pairing key into the payload of second advertisement message 714. Display device 710 can be configured to extract and decrypt this embedded pairing key.

Block 866 includes generating and transmitting a pairing request message comprising the decrypted pairing key. For example, display device 710 can be configured to generate and transmit pairing request message 716 having the decrypted pairing key received in second advertisement message 714 to analyte sensor system 708.

Block 868 includes determining whether the pairing request has been accepted. For example, display device 710 can determine that the pairing request initiated by the transmission of pairing request message 716 was accepted based on receiving pairing request acceptance message 718 from analyte sensor system 708, or alternatively, based on not receiving a pairing request denial or negative acknowledgment message from analyte sensor system 708 within a predetermined period of time after transmission of pairing request message 716.

If the determination at block 868 is negative, flowchart 850 advances to block 872, which includes determining whether a timeout counter has expired. If yes, flowchart 850 advances to block 874, where a manual pairing of analyte sensor system 708 and display device 710, e.g., manually entering a transmitter ID into display device 710, can take place and a secure communication session, e.g., for securely communicating encrypted analyte data, can be entered at block 870. If no, flowchart 850 circles back to block 856. If the determination at block 868 is affirmative, a secure communication session can be entered at block 870.

Figure 9:
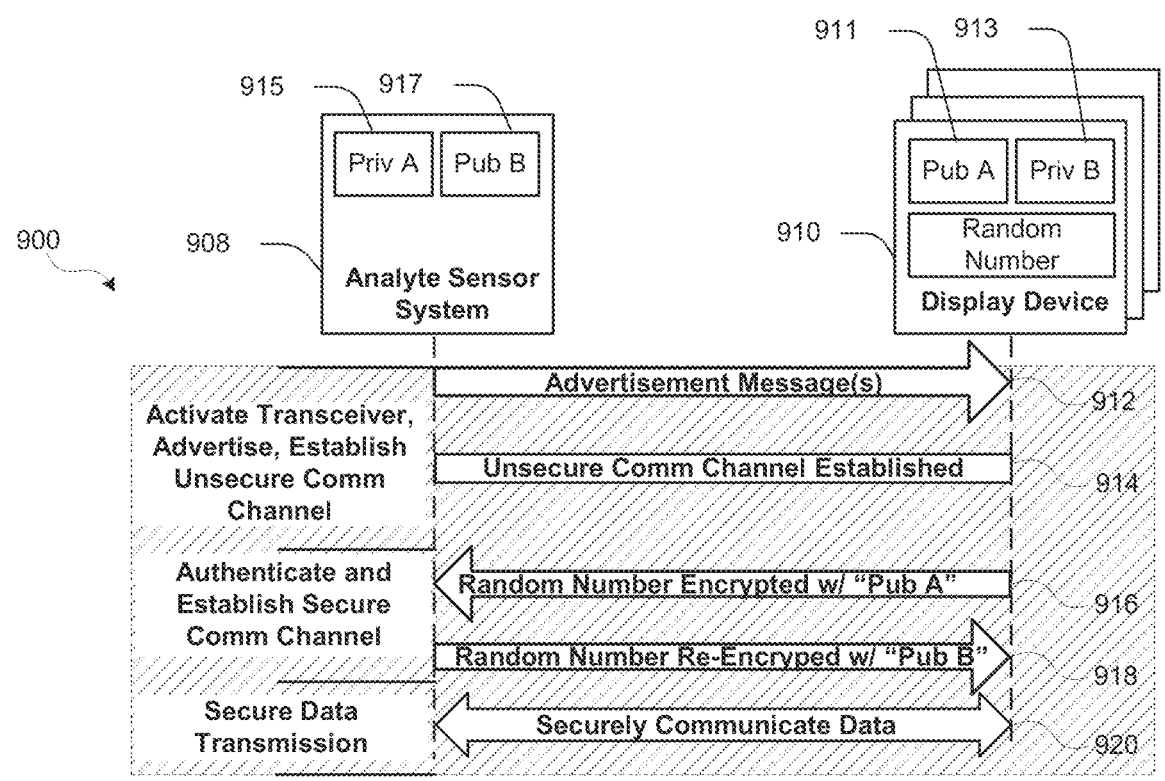
FIG. 9 is a signaling diagram illustrating various operations that can be performed in accordance with embodiments of the disclosure.
Figure 10A:
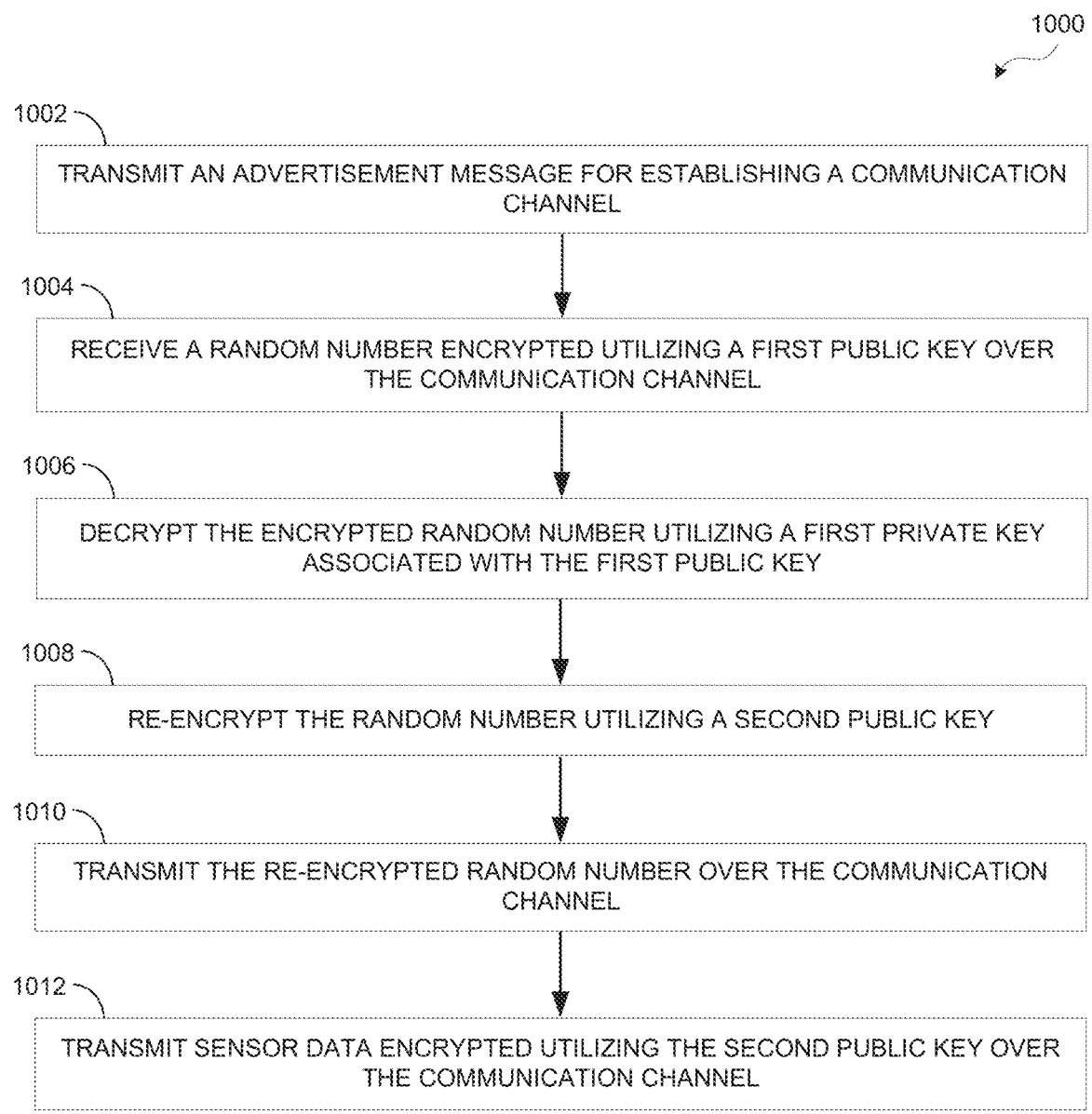
FIG. 10A is an operational flow diagram illustrating various operations that can be performed in accordance with embodiments of the disclosure.
Figure 10B:
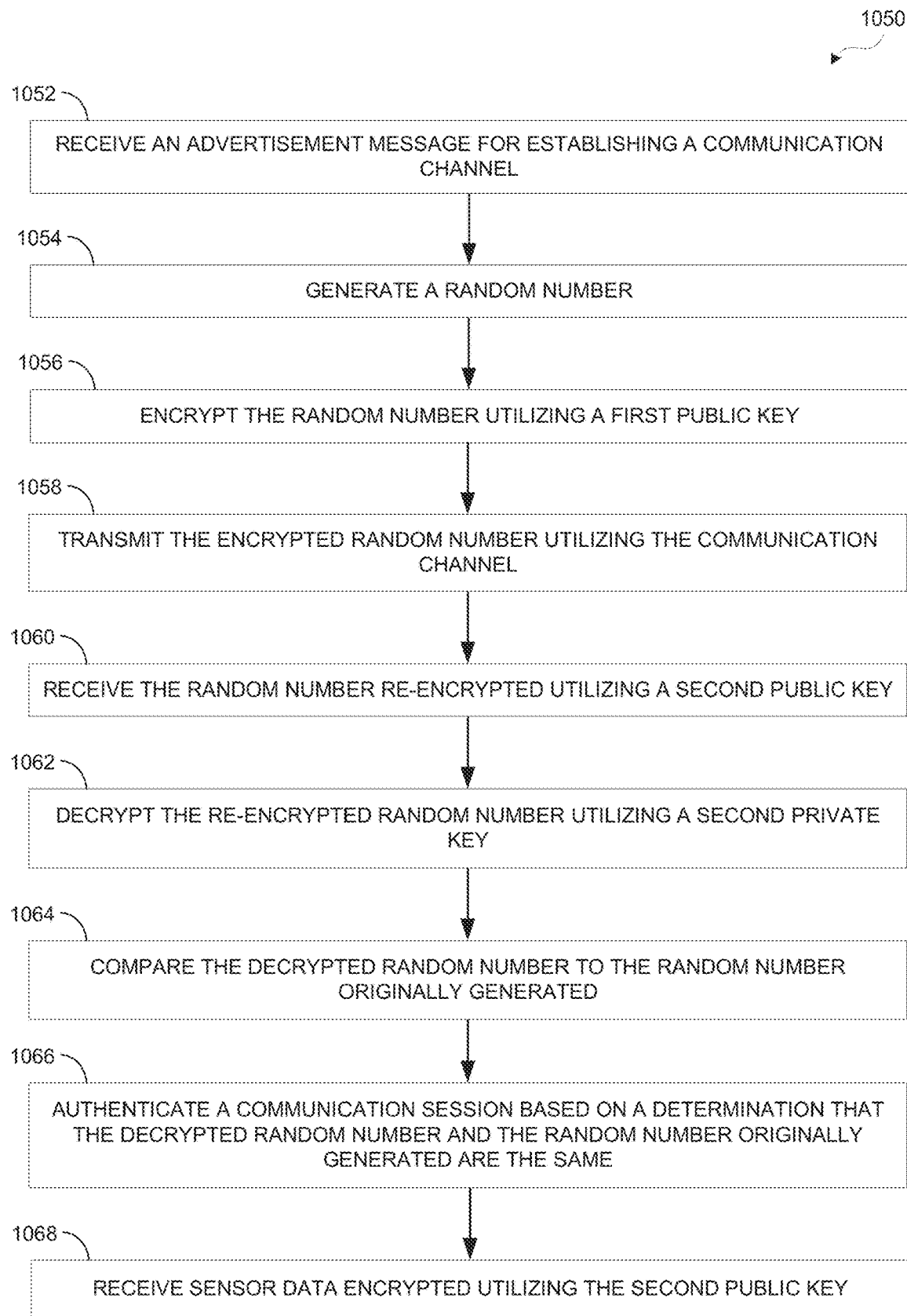
FIG. 10B is an operational flow diagram illustrating various operations that can be performed in accordance with embodiments of the disclosure.

FIGS. 9-10B describe embodiments utilizing asymmetric cryptographic keys (e.g., using a single public key and multiple corresponding private keys) to automatically establish a secure link between an analyte sensor system and one or more peripheral display devices.

FIG. 9 illustrates a messaging diagram of a pairing operation between an analyte sensor system 908 and one or more display devices 910, according to some example embodiments. In some embodiments, analyte sensor system 908 and display device(s) 910 can correspond to analyte sensor system 308 and any of display devices 310, respectively, as previously described in connection with FIGS. 3A-3E. FIG. 10A is a flowchart 1000 illustrating various operations that can be performed in accordance with embodiments of the disclosure. In some embodiments, flowchart 1000 of FIG. 10A corresponds to operations and/or actions performed by analyte sensor system 908 of FIG. 9. FIG. 10B is a flowchart 1050 illustrating various operations that can be performed in accordance with embodiments of the disclosure. In some embodiments, flowchart 1050 of FIG. 10B corresponds to operations and/or actions performed by display device(s) 910 of FIG. 9.

The various tasks in connection with the procedures illustrated in FIGS. 9-10B can be performed, for example, by respective processors executing instructions embodied in respective non-transitory computer-readable media. The tasks or operations performed in connection with the procedures can be performed by hardware, software, firmware, or any combination thereof incorporated into one or more of computing devices. It will be appreciated upon studying the present disclosure that such procedures can include any number of additional or alternative tasks or operations. The operations shown by way of example in FIGS. 10A-10B need not be performed in the illustrated order, and the procedures can be incorporated into more comprehensive procedures or processes having additional functionality not described in detail herein with specific reference to FIGS. 10A-10B.

An example pairing operation will now be described in connection with FIG. 9. In some embodiments, before the operations described below, a user can download, for example from an app store, and/or otherwise initialize an application for monitoring an analyte concentration of the user to display device 910. The application on display device 910 can comprise a single public key 911 "Pub A" that corresponds, for example, to a particular product platform (e.g., analyte sensor system 908). For example, applications configured to run on display device 910 and receive, monitor, and/or display analyte concentration data from a same model or class of models of analyte sensor 908 can be preloaded with, or have public access to, public key 911 "Pub A," which can be utilized to encrypt data. The application on display device 910 can also comprise a private key 913 "Priv B" configured to decrypt data previously encrypted with a corresponding different single public key 917 "Pub B" preloaded on or publicly available to the particular product platform (e.g., analyte sensor system 908).

Analyte sensor system 908 can comprise public key 917 "Pub B," which is configured to encrypt data, and a unique private key 915 "Priv A," which is configured to decrypt data previously encrypted utilizing public key 911 "Pub A" at display device 910. Public key 917 "Pub B" can be pre-loaded on each analyte sensor system 908 of a given product platform at the factory. In some embodiments, private keys 911, 913 can be obtained via secure download or by any other suitable method.

A public key is termed "public" because it is publicly available to or generally known by devices, while a private key is termed "private" because it is not publicly available to or known by all devices and is kept secret from all but authorized devices. As described herein each Public Key can encrypt data utilizing a common algorithm. A plurality of unique Private Keys that are associated with the same single Public Key can each comprise a unique algorithm configured to decrypt data previously encrypted with the associated Public Key's common algorithm. Thus, in such embodiments, encryption-to-decryption is one to many, as a single common algorithm is utilized to encrypt data, while any one of a plurality of unique corresponding algorithms can be utilized to decrypt the previously encrypted data.

A user of display device 910 can complete a setup of the application, after which the user can deploy analyte sensor system 908 in preparation of a pairing operation to be conducted between analyte sensor system 908 and display device 910. The application running on display device 910 can begin monitoring for advertisement messages, e.g., BLE advertisement messages. Upon activation, analyte sensor system 908 can be configured to wake up from a lower power or sleep mode, for example, as previously described in connection with FIG. 4.

Upon waking, analyte sensor system 908 can transmit an advertisement message 912, utilizing a transceiver radio, thereby causing a communication channel 914 to be established with display device 910. One or more additional communications between analyte sensor system 908 and display device 910 (not shown) can occur during establishment of communication channel 914. Private data, e.g., analyte values or indications of the same, is not yet sent, but communication channel 914 can now be utilized to communicate encrypted data between analyte sensor system 908 and display device 910 for subsequently establishing a secure communication channel.

Upon establishment of communication channel 914, display device 910 can generate a random number and encrypt it utilizing public key 911 "Pub A." Display device 910 can then transmit the encrypted random number 916 to analyte sensor system 908 utilizing communication channel 914.

Upon receipt, analyte sensor system 908 can decrypt the encrypted random number utilizing private key 915 "Priv A." Analyte sensor system 908 can then re-encrypt the random number utilizing public key 917 "Pub B." Analyte sensor system 908 can then transmit the re-encrypted random number to display device 910 utilizing communication channel 914.

Upon receipt, display device 910 can decrypt the re-encrypted random number utilizing private key 913 "Priv B." Display device 910 then compares the decrypted random number with the originally generated random number. If they are the same, communication between analyte sensor system 908 and display 910 is authenticated and data 920 can now be transmitted securely. For example, if data 920 is transmitted by display device 910, it can be encrypted by display device 910 utilizing public key 911 "Pub A" and decrypted by analyte sensor system 908 utilizing private key 915 "Priv A." Likewise, if data 920 is transmitted by analyte sensor system 908, it can be encrypted by analyte sensor system 908 utilizing public key 917 "Pub B" and decrypted by display device 910 utilizing private key 913 "Priv B." In some embodiments, data 920 can comprise session data including one or more analyte concentration values.

Description now turns to flowchart 1000 of FIG. 10A, describing operations of, for example, analyte sensor system 908. Block 1002 includes transmitting an advertisement message for establishing a communication channel. For example, analyte sensor system 908 can transmit advertising message 912 for establishing communication channel 914.

Block 1004 includes receiving a random number encrypted utilizing a first public key over the communication channel. For example, analyte sensor system 908 can be configured to receive random number 916 encrypted utilizing public key 911 "Pub A" from display device 910 over communication channel 914.

Block 1006 includes decrypting the encrypted random number utilizing a first private key associated with the first public key. For example, analyte sensor system 908 can be configured to decrypt encrypted random number 916 utilizing private key 915 "Priv A."

Block 1008 includes re-encrypting the random number utilizing a second public key. For example, analyte sensor system 908 can be configured to re-encrypt the now-decrypted random number from block 1006 utilizing public key 917 "Pub B."

Block 1010 includes transmitting the re-encrypted random number over the communication channel. For example, analyte sensor system 908 can be configured to transmit re-encrypted random number 918 over unsecure communication channel 914 to display device 910.

Block 1012 includes transmitting sensor data encrypted utilizing the second public key over the communication channel. For example, upon authentication of the communications between analyte sensor system 908 and display device 910, sensor session data can be encrypted utilizing public key 917 "Pub B" and transmitted by analyte sensor system 908 to display device 910 over communication channel 914. In some embodiments, display device 910 can also be configured to transmit data securely over communication channel 914 by encrypting it with public key 911 "Pub A." Analyte sensor system 908 can decrypt this encoded data utilizing private key 915 "Priv A." Since all communications are now encrypted, communications over communication channel 914 are now secure.

Description now turns to flowchart 1050 of FIG. 10B, describing operations of, for example, display device(s) 910. Block 1052 includes receiving an advertisement message for establishing a communication channel. For example, display device 910 can be configured to receive advertising message 912 for establishing communication channel 914 from analyte sensor system 908.

Block 1054 includes generating a random number. For example, display device 910 can be configured to generate a random number utilizing any suitable generation method.

Block 1056 includes encrypting the random number utilizing a first public key. For example, display device 910 can be configured to encrypt the random number utilizing public key 911 "Pub A."

Block 1058 includes transmitting the encrypted random number utilizing the communication channel. For example, display device 910 can be configured to transmit the encrypted random number 916 utilizing communication channel 914.

Block 1060 includes receiving the random number re-encrypted utilizing a second public key. For example, display device 910 can be configured to receive re-encrypted random number 918 (encrypted random number 916 previously decrypted utilizing private key 915 "Priv A" then re-encrypted utilizing public key 917 "Pub B" by analyte sensor system 908).

Block 1062 includes decrypting the re-encrypted random number utilizing a second private key. For example, display device 910 can be configured to decrypt re-encrypted random number 918 utilizing private key 913 "Priv B."

Block 1064 includes comparing the decrypted random number to the random number originally generated. For example, display device 910 can be configured to compare the decrypted version of re-encrypted random number 918 with the original random number generated by display device 910 at block 1054.

Block 1066 includes authenticating a communication session based on a determination that the decrypted random number and the random number originally generated are the same. For example, display device 910 can be configured to validate and/or authenticate that it is communicating with a trusted device (i.e., analyte sensor system 908) based on the above comparison and a subsequent determination that the decrypted version of re-encrypted random number 918 and the original random number generated by display device 910 at block 1054 are the same number.

Block 1068 includes receiving sensor data encrypted utilizing the second public key. For example, upon authentication of the communications between analyte sensor system 908 and display device 910, display device 910 can be configured to receive sensor session data encrypted utilizing public key 917 "Pub B" and transmitted by analyte sensor system 908. In some embodiments, display device 910 can also be configured to transmit data securely by encrypting it with public key 911 "Pub A." Analyte sensor system 908 can decrypt this encoded data utilizing private key 915 "Priv A." Since all communications are now encrypted, communications over the communication channel 914 are now secure.

Selecting Low-Interference Channels for Communication

In some embodiments, initial advertising for establishing a communication channel can occur during intervals where one or more other devices are concurrently communicating. Such interfering communications can adversely affect the efficiency and/or effectiveness of desired communications on these channels. Accordingly, it can be desirable to select a channel of a plurality of predetermined channels that has a least amount of interference for such advertising and subsequent communication. Discussion regarding implementations that can provide for such channel selection will now follow in connection with FIGS. 11 and 12 below.

Figure 11:
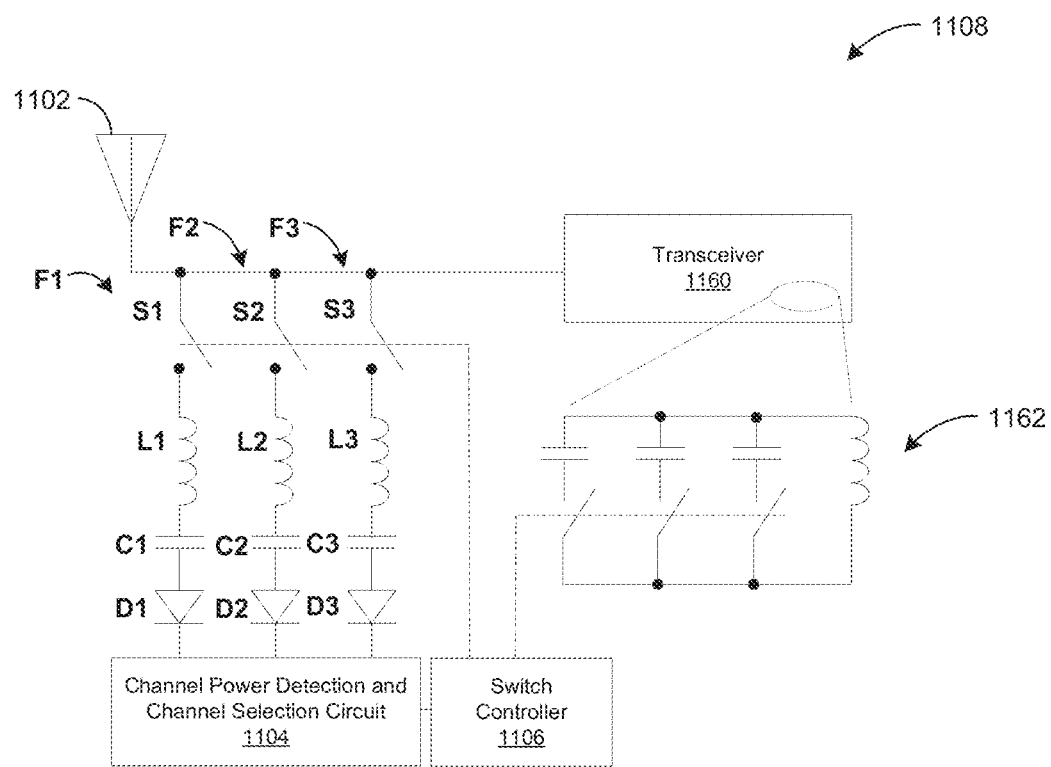
FIG. 11 illustrates a schematic circuit diagram illustrating aspects of a portion of an example analyte sensor system according to embodiments of the disclosure.

FIG. 11 illustrates a portion of an analyte sensor system 1108, according to some example embodiments. In some embodiments, analyte sensor system 1108 can correspond to analyte sensor system 308 as previously described in connection with any of FIGS. 3A-3E. Analyte sensor system 1108 comprises an antenna 1102 coupled to or included in a transceiver 1160. Transceiver 1160 can include a frequency selection circuit 1162 configured to select a channel (e.g., frequency band) on which antenna 1102 can transmit and/or receive one or more signals. Antenna 1102 is further coupled to each of a plurality of filters F1, F2, F3 via respective switches S1, S2, S3. In some embodiments, filters F1, F2, F3 can pass signals on BLE channels 37, 38 and 39 corresponding to 2402 MHz, 2426 MHz and 2480 MHz, respectively. However, the present disclosure is not so limited and filters F1, F2, F3 can be configured to pass signals on any other frequencies and/or channels of any suitable wireless communication protocol. In addition, although three filters are illustrated, the present disclosure is not so limited, and any number of filters can be utilized.

In some embodiments, each filter F1, F2, F3 comprises a respective inductor L1, L2, L3, a respective capacitor C1, C2, C3 and a respective diode D1, D2, D3 connected in series. However, the present disclosure is not so limited and any filter, analog or digital, can be utilized. Each filter F1, F2, F3 can comprise a bandpass filter configured to pass signals within a respective frequency band (e.g. tuned to a respective channel for BLE advertising) to a power detection and channel selection circuit 1104 coupled to each filter F1, F2, F3. Channel power detection and channel selection circuit 1104 can also be coupled to a switch controller 1106 and can be configured to send one or more signals to switch controller 1106 that cause switch controller 1106 to select one of the filters F1, F2, F3 by closing the respective switch S1, S2, S3 and/or that cause switch controller 1106 to cause frequency selection circuit 1162 to select a channel (e.g., frequency band) on which antenna 1102 can transmit and/or receive one or more signals.

In some embodiments, during intervals in which analyte sensor system 1108 and/or a corresponding display device (not shown in FIG. 11) are not scheduled to transmit any signals, switch controller 1106 can be configured to couple each of the filters F1, F2, F3 to antenna 1102, either simultaneously or sequentially, while channel power detection and channel selection circuit 1104 is configured to measure an amount of power (for example, noise in this case) received on each channel corresponding to each filter F1, F2, F3. Channel power detection and channel selection circuit 1104 can be configured to compare the measured power on each corresponding channel and select the channel having the lowest measured power. The channel with the lowest measured power can be assumed to exhibit the lowest levels of interference to signals transmitted and/or received by transceiver 1160 since all power measured on a channel is inherently noise during intervals in which analyte sensor system 1108 and/or a corresponding display device (not shown in FIG. 11) are not scheduled to transmit any signals. Channel power detection and channel selection circuit 1104 can be configured to select the channel corresponding to the lowest measured power and send at least one signal to switch controller 1106 that causes switch controller 1106 to cause frequency selection circuit 1162 to select the corresponding channel for antenna 1102 to transmit and/or receive one or more signals thereon. In different embodiments, the above-described interference determination and channel selection can be carried out once, a plurality of times, or periodically between each transmission interval to allow for dynamic and/or periodic interferers to be accounted for. In some embodiments, another processor (e.g., a CPU) can override the channel selection provided by channel power detection and channel selection circuit 1104 for any number of reasons.

Figure 12:
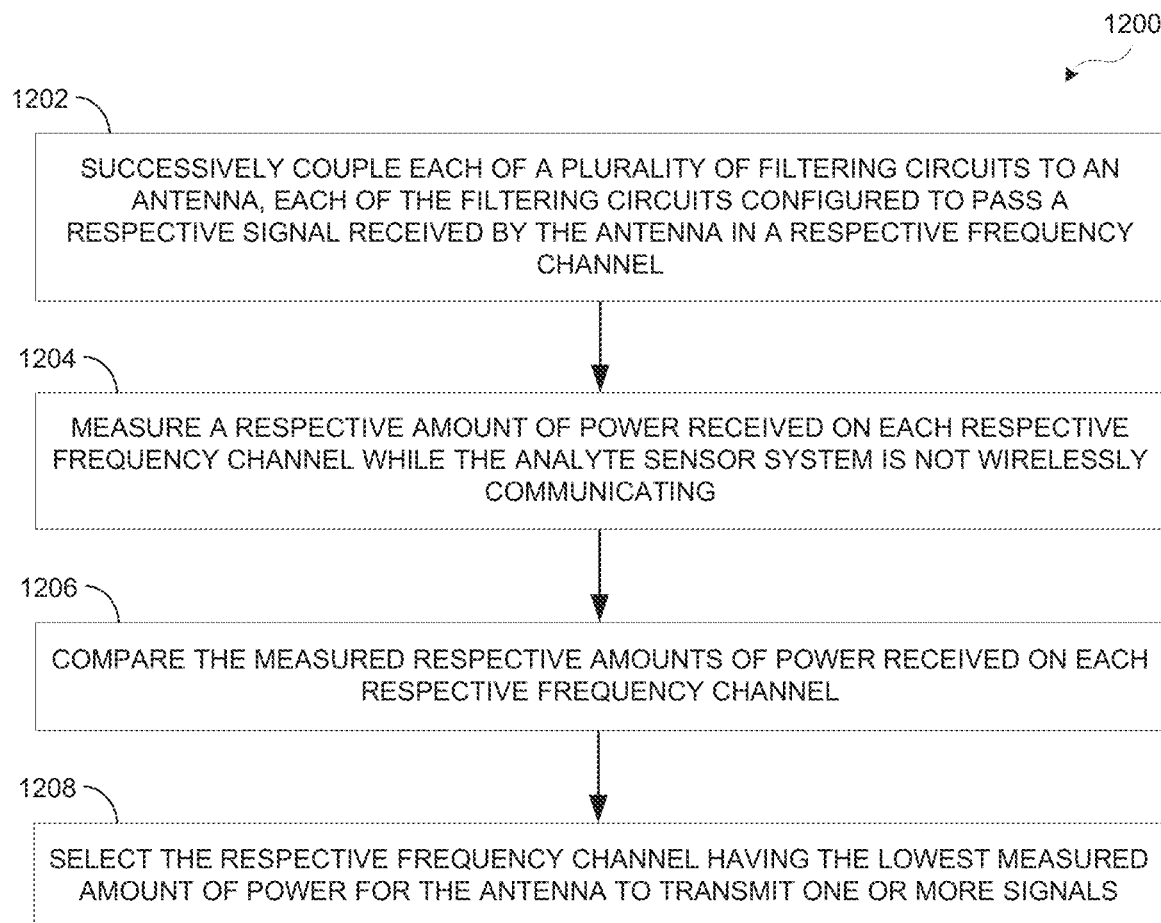
FIG. 12 is an operational flow diagram illustrating various operations that can be performed in accordance with embodiments of the disclosure.

Description now turns to flowchart 1200 of FIG. 12, describing operations of, for example, portions of analyte sensor system 1108 of FIG. 11. Block 1202 includes successively coupling each of a plurality of filtering circuits to an antenna, each of the filtering circuits configured to pass a respective signal received by the antenna in a respective frequency channel. For example, switch controller 1106 can be configured to successively couple each of filters F1, F2, F3 to antenna 1102 by closing a respective switch S1, S2, S3.

Block 1204 includes measuring a respective amount of power received on each respective frequency channel while the analyte sensor system is not wirelessly communicating. For example, channel power detection and channel selection circuit 1104 can be configured to measure a respective amount of power received on each respective frequency channel passed by filters F1, F2, F3 while analyte sensor system 308 is not wirelessly communicating.

Block 1206 includes comparing the measured respective amounts of power received on each respective frequency channel. For example, channel power detection and channel selection circuit 1104 can be configured to compare the measured respective amounts of power received on each respective frequency channel.

Block 1208 includes selecting the respective frequency channel having the lowest measured amount of power for the antenna to transmit one or more signals. For example, channel power detection and channel selection circuit 1104 can be configured to select the channel corresponding to the lowest measured power and send at least one signal to switch controller 1106 that causes switch controller 1106 to cause frequency selection circuit 1162 to select the corresponding channel for antenna 1102 to transmit and/or receive one or more signals thereon.

Reversing Slave-Master Roles of the Analyte Sensor System and Display Devices when Establishing Communication Sessions In several of the above descriptions (e.g., FIGS. 7-10B), the analyte sensor system acts as a slave device and the display device(s) act as the master device at least in that the analyte sensor system transmitter (e.g., which acts as a BLE peripheral device) is configured to wake periodically (e.g., every 5 minutes) and advertise for a period of time in expectation of being monitored by the display device (e.g., which acts as the BLE master, central device). Once the display device(s) has discovered the analyte sensor system, a wireless connection is established and authenticated, command and control are accomplished via the exchange of control endpoints and attributes. However, such intermittent advertising by the analyte sensor system transmitter can require more power than passively monitoring one or more communication channels for advertisements.

Accordingly, the present disclosure also contemplates reversing the roles of the analyte sensor system and the display device(s) at least with respect to establishing communication sessions with one another. At least one embodiment is described below in connection with FIG. 13. However, the present disclosure is not so limited and this reversal concept can be applied to any description herein regarding establishing a communication session between an analyte sensor system (or any of its components) and a display device (or any of its components) such that actions, steps or procedures described as being carried out by one can alternatively be carried out by the other and vice versa.

Figure 13:
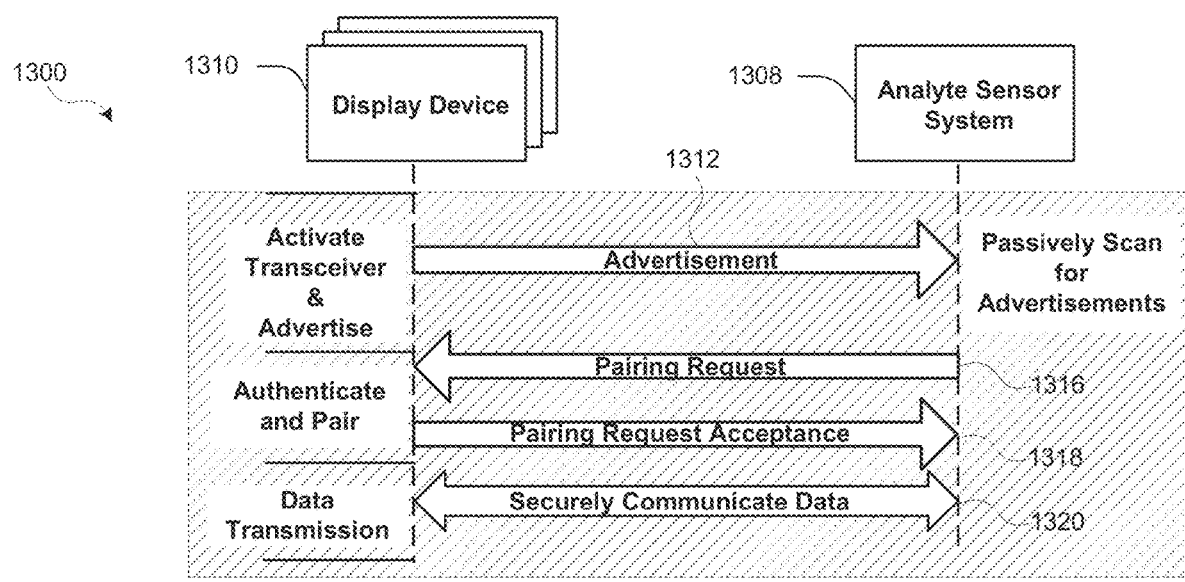
FIG. 13 is a signaling diagram illustrating various operations that can be performed in accordance with embodiments of the disclosure.

FIG. 13 illustrates a messaging diagram of a pairing operation between an analyte sensor system 1308 and one or more display devices 1310, according to some example embodiments. In some embodiments, analyte sensor system 1308 and display device(s) 1310 can correspond to analyte sensor system 308 and any of display devices 310, respectively, as previously described in connection with FIGS. 3A-3E.

Analyte sensor system 1308 can be configured to passively monitor for advertisements from peripheral devices of an expected type (e.g., display device 1310). Such monitoring can consume less power than advertising and has the advantage that it can be carried out continuously while one or more processors within analyte sensor system 1308 are asleep, for example, as previously described in connection with FIG. 4. Upon display device 1310 waking, it can be configured to turn on its BLE radio and generate and transmit an advertisement message 1312.

Based on the monitoring, analyte sensor system 1308 can be configured to detect advertisement message 1312. In response to detection, and in some cases validation (e.g., as described elsewhere herein or according to any otherwise known validation and/or authentication procedure), of advertisement message 1312, analyte sensor system 1308 can be configured to generate and transmit a pairing request 1316. Display device 1310 can receive pairing request 1316 and, in response, generate and transmit a pairing request acceptance message 1318 to analyte sensor system 1308. Analyte sensor system 1308 and display device 1310 can then enter a secure sensor communication session. In some embodiments, analyte sensor system 1308 can be configured to initiate a switch from functioning as a slave device to operating as the master device, as described above, based on satisfaction of one or more criteria, for example based on determination that a battery charge within analyte sensor system 1308 has fallen below a predetermined level.

Display Device-Initiated Transmission of Session Data from the Analyte Sensor System To conserve power in analyte sensor systems, some embodiments contemplate intermittent connectivity between the analyte sensor system and one or more display devices wherein the analyte sensor system wakes up periodically (e.g., every 5 minutes) from a low-power or sleep mode to perform an analyte concentration measurement and transmit an indication of the measurement to the display device. However, in such embodiments, data (e.g., measurement data and/or analyte values) can be sent from the analyte sensor system to the display device only during the periodic wake interval and some users may not want to wait another interval before data is transmitted to the display device, especially when the user has not received data in an extended period of time (e.g., when the display device was out of range for an extended period of time.

Accordingly, some embodiments contemplate protocols where the analyte sensor system is configured to monitor, from a low-power state, for a signal configured to wake the analyte sensor system, cause it to initiate a pairing operation, and communicate session data without waiting for a next periodic or otherwise scheduled wake interval.

Figure 14:
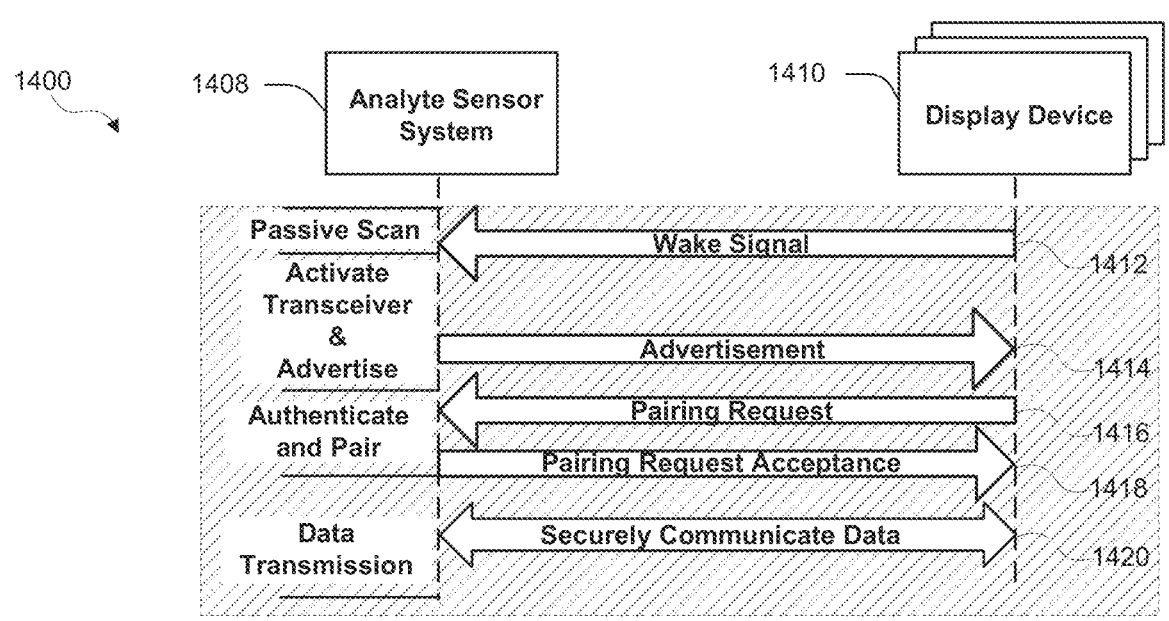
FIG. 14 is a signaling diagram illustrating various operations that can be performed in accordance with embodiments of the disclosure.

FIG. 14 illustrates a messaging diagram of a pairing operation between an analyte sensor system 1408 and one or more display devices 1410, according to some example embodiments. In some embodiments, analyte sensor system 1408 and display device(s) 1410 can correspond to analyte sensor system 308 and any of display devices 310, respectively, as previously described in connection with FIGS. 3A-3E.

FIG. 14 illustrates analyte sensor system 1408 and one or more display devices 1410. Analyte sensor system 1408 can be in a low-power, or sleep mode, passively monitoring for a signal configured to wake the analyte sensor system before a predetermined interval for waking has expired.

Display device 1410 can be configured to transmit a wake signal 1412 (e.g., an RF, IR, optical, audio or any other suitable signal) having a predetermined pattern, magnitude or modulation to analyte sensor system 1408. Upon detection of wake signal 1412, analyte sensor system 1408 can be configured to wake from the low-power or sleep mode (e.g., as previously described in connection with FIG. 4) and transmit an advertisement message 1414 for initiating a pairing operation. In response to detection, and in some cases validation, of advertisement message 1412, display device 1410 can be configured to generate and transmit a pairing request 1416. Analyte sensor system 1408 can receive pairing request 1416 and, in response, generate and transmit a pairing request acceptance message 1418 to display device 1410. Analyte sensor system 1408 and display device 1410 can then enter a secure sensor communication session in which analyte sensor system 1408 can transmit data, e.g., sensor data, to display device 1410. In some embodiments, transmission of such sensor data can comprise fulfilling a backfill request for specific data from display device 1410 and/or any other data at a time before a predetermined interval for waking analyte sensor system 1408 has expired.

Figure 15A:
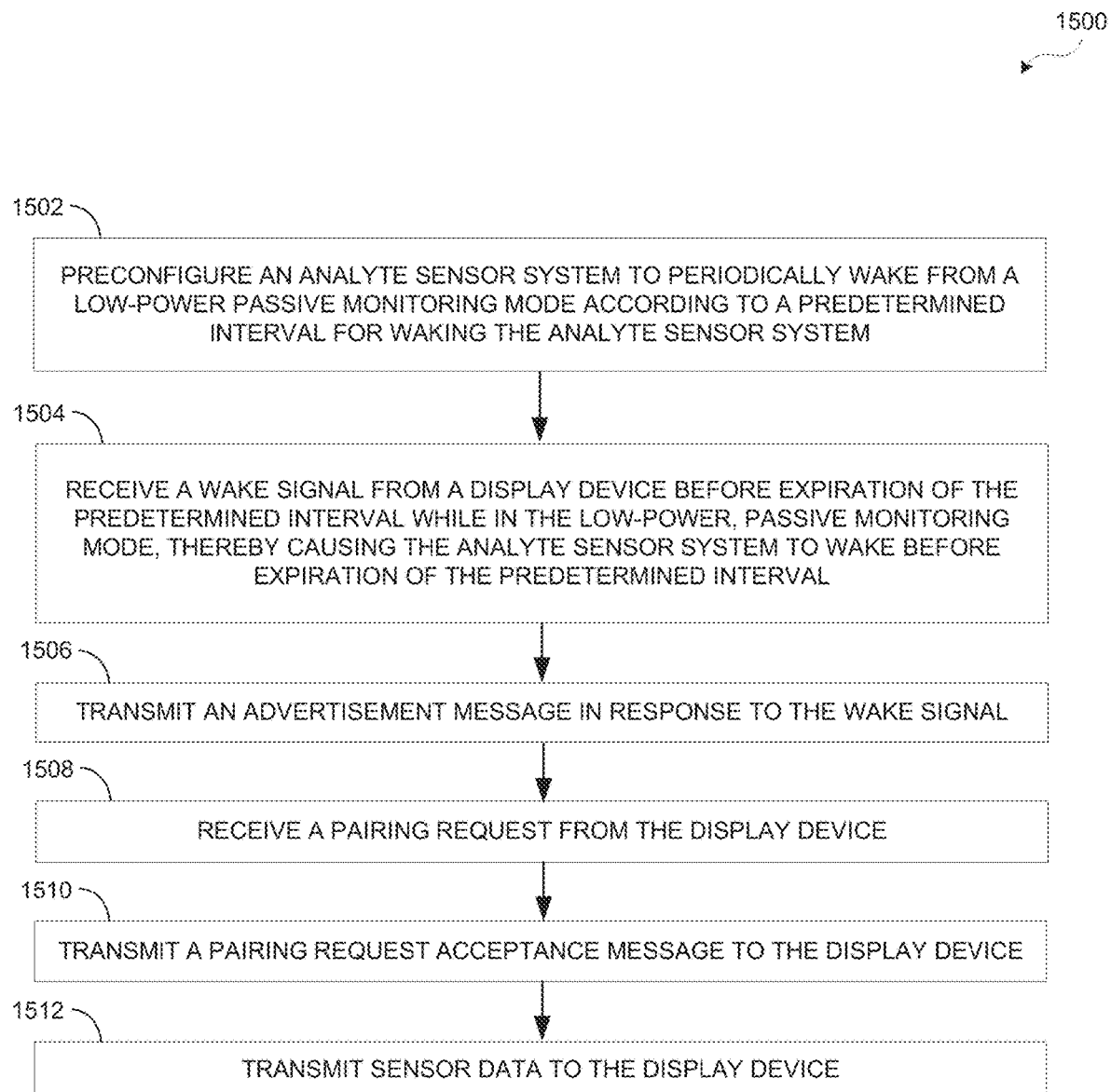
FIG. 15A is an operational flow diagram illustrating various operations that can be performed in accordance with embodiments of the disclosure.

Description now turns to flowchart 1500 of FIG. 15A, describing operations of, for example, portions of analyte sensor system 1408 of FIG. 14. Block 1502 includes preconfiguring an analyte sensor system to periodically wake from a low-power passive monitoring mode according to a predetermined interval for waking the analyte sensor system. For example, analyte sensor system 1408 can be preconfigured to periodically wake from a low-power passive monitoring mode according to a predetermined interval for waking analyte sensor system 308.

Block 1504 includes receiving a wake signal from a display device before expiration of the predetermined interval while in the low-power passive monitoring mode, thereby causing the analyte sensor system to wake before expiration of the predetermined interval. For example, analyte sensor system 1408 can receive wake signal 1412 from display device 1410 before expiration of the predetermined interval while in the low-power passive monitoring mode, thereby causing analyte sensor system 1408 to wake before expiration of the predetermined interval.

Block 1506 includes transmitting an advertisement message in response to the wake signal. For example, analyte sensor system 1408 can be configured to exit the low-power passive monitoring mode and transmit advertisement message 1414 in response to receiving wake signal 1408.

Block 1508 includes receiving a pairing request from the display device. For example, analyte sensor system 1408 can be configured to receive pairing request 1416 from display device 1410.

Block 1510 includes transmitting a pairing request acceptance message to the display device. For example, analyte sensor system 1408 can be configured to transmit pairing request acceptance message 1418 to display device 1410.

Block 1512 includes transmitting sensor data to the display device. For example, analyte sensor system 1408 can be configured to enter a secure sensor communication session based on the above communications in which analyte sensor system 1408 can transmit data, e.g., sensor data, to display device 1410. In some embodiments, transmission of such sensor data can comprise fulfilling a backfill request for specific data from display device 1410 and/or any other data at a time before a predetermined interval for waking analyte sensor system 1408 has expired.

Figure 15B:
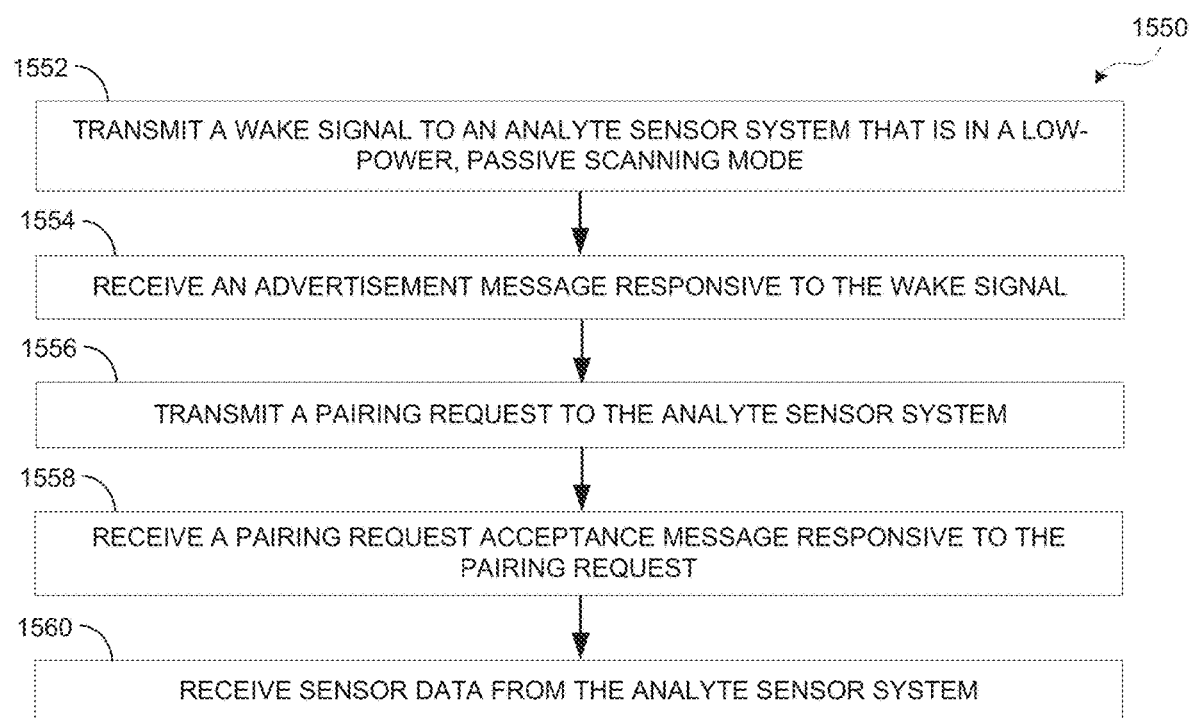
FIG. 15B is an operational flow diagram illustrating various operations that can be performed in accordance with embodiments of the disclosure.

Description now turns to flowchart 1550 of FIG. 15B, describing operations of, for example, portions of display device 1510 of FIG. 14. Block 1552 includes transmitting a wake signal to an analyte sensor system that is in a low-power passive monitoring mode. For example, display device 1410 can be configured transmit wake signal 1412 to analyte sensor system 1408 while in a low-power passive monitoring mode.

Block 1554 includes receiving advertisement message responsive to the wake signal. For example, display device 1410 can be configured to receive advertisement message 1414, responsive to wake signal 1408, from analyte sensor system 1408.

Block 1556 includes transmitting a pairing request to the analyte sensor system. For example, display device 1410 can be configured to transmit pairing request 1416 to analyte sensor system 1408.

Block 1558 includes receiving a pairing request acceptance message responsive to the pairing request. For example, display device 1410 can be configured to receive pairing request acceptance message 1418, responsive to pairing request 1416, from analyte sensor system 1408.

Block 1560 includes receiving sensor data from the analyte sensor system. For example, display device 1410 can be configured to enter a secure sensor communication session based on the above communications in which display device 1410 receives data, e.g., sensor data, from analyte sensor system 1408. In some embodiments, transmission and reception of such sensor data can comprise fulfilling a backfill request for specific data from display device 1410 and/or any other data at a time before a predetermined interval for waking analyte sensor system 1408 has expired.

Utilizing Stickers Comprising NFC Tags for Pairing Analyte Sensor System and Display Device In some embodiments, initial pairing between an analyte sensor system and a display device requires verifying and validating that the analyte sensor system and the display device are authorized to connect to and communicate with one another. Some embodiments require a user to manually enter a serial number or the like from the analyte sensor system and/or its packaging into an application running on the display device as a step in performing such initial verification and validation. However, such procedures can be cumbersome for users. Accordingly, the present disclosure contemplates initially pairing an analyte sensor system to one or more display devices without requiring manual entry of such serial numbers or the like by a user, thereby providing a simpler, streamlined setup experience for the user.

Figure 16:
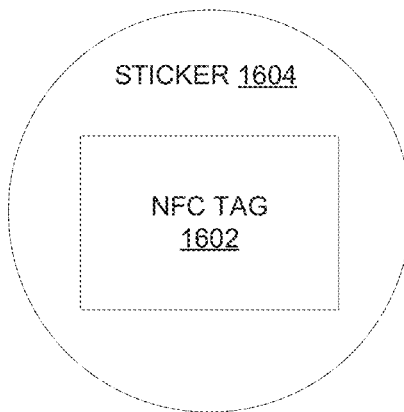
FIG. 16 illustrates an NFC tag embedded in a sticker in accordance with embodiments of the disclosure.

FIG. 16 illustrates an NFC tag 1602 embedded in a sticker 1604, which can be utilized to initially transfer identifying information for an analyte sensor system 308, for example, as previously described in connection with at least FIGS. 3A-3E, to a display device 310. During manufacture, NFC tag 1602 can be embedded in sticker 1604 and pre-programmed with a pairing key (e.g., a BLE encryption key). At the time of kitting of analyte sensor system 308, sticker 1604 can be fixed to analyte sensor kit box 398 (see FIG. 3D). When the user is ready to pair analyte sensor system 308 with a particular NFC-enabled display device 310, the user can physically move display device 310 sufficiently close to sticker 1604 (and NFC tag 1602 therein) (e.g., within several centimeters) such that display device 310 is able to retrieve the pairing key from NFC tag 1602 within sticker 1604 via NFC. In some embodiments, physically moving display device 310 sufficiently close to sticker 1604 can comprise tapping display device 310 against sticker. Then, utilizing the pairing key, display device 310 can be further configured to initiate a pairing protocol with analyte sensor system 308, or alternatively participate in completion of a pairing protocol initiated by analyte sensor system 308, according to any embodiment described in this disclosure, or according to any other pairing protocol. For example, in some embodiments, analyte sensor system 308 may be configured to pair, or initiate pairing, with display device 310 utilizing the pairing key. That is, display 310 need not initiate a pairing process. For example, analyte sensor system 308 may be configured to advertise, while display 310 utilizes the pairing key in subsequent communications with analyte sensor system 308 to complete the pairing process.

Figure 17:
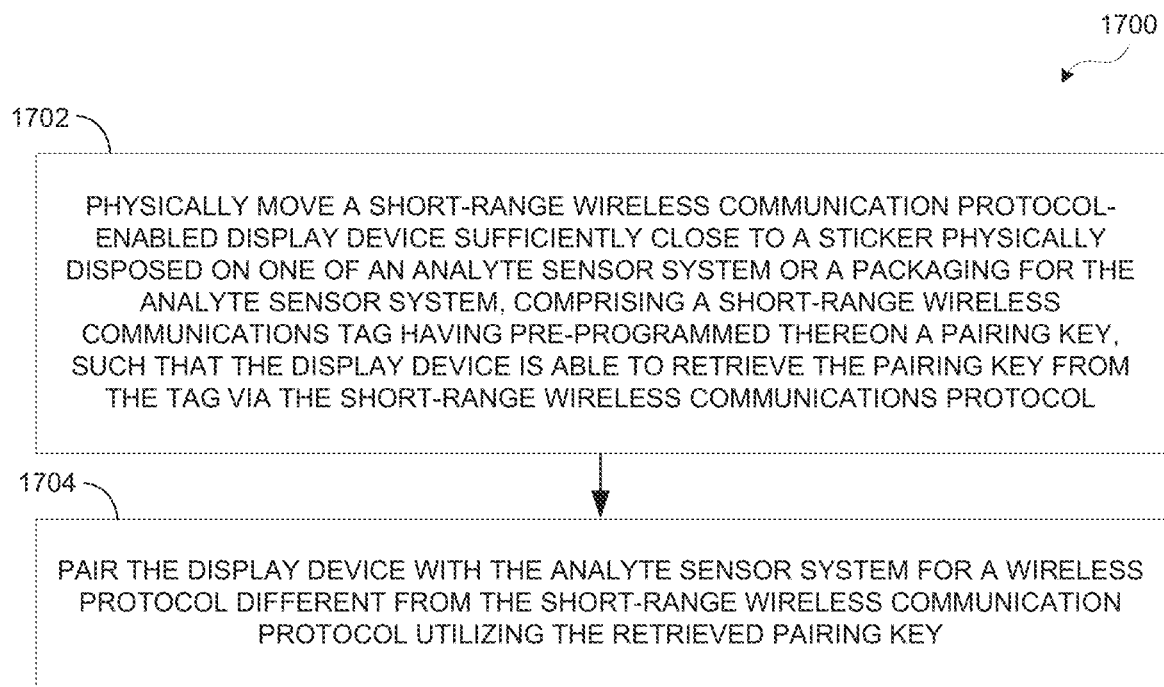
FIG. 17 is an operational flow diagram illustrating various operations that can be performed in accordance with embodiments of the disclosure.

Description now turns to flowchart 1700 of FIG. 17, describing operations of, for example, any display device described herein. Block 1702 includes physically moving a short-range wireless communication protocol-enabled display device sufficiently close to a sticker physically disposed on one of an analyte sensor system or a packaging for the analyte sensor system, comprising a short-range wireless communications tag having pre-programmed thereon a pairing key, such that the display device is able to retrieve the pairing key from the tag via the short-range wireless communication protocol. In some embodiments, the tag may further include one or more of sensor-related information, a sensor expiration date, license information, calibration information, or any other information. In some embodiments, the short-range wireless communications protocol may be an NFC protocol and the tag may be an NFC tag. For example, at the time of initial pairing of analyte sensor system 308 and NFC-enabled display device 310, a user can physically move display device 310 sufficiently close to sticker 1604, comprising NFC tag 1602 having pre-programmed thereon a pairing key, such that display device 310 is able to retrieve the pairing key from NFC tag 1602 via NFC.

Block 1704 includes pairing the display device with the analyte sensor system for a wireless protocol different from the short-range wireless communication protocol utilizing the retrieved pairing key. For example, display device 310 can pair with analyte sensor system 308 for a wireless protocol different from the short-range wireless communication protocol (e.g., Wi-Fi, Bluetooth, BLE, cellular or any other suitable communication protocol) utilizing the pairing key retrieved from NFC tag 1602 according to any embodiment described in this disclosure, or according to any other pairing protocol.

Utilizing Optical Means for Initiating Establishment of a Secure Connection with an Analyte Sensor System Some embodiments, where secure communication between an analyte sensor system and one or more display devices are established, require a user to read a transmitter ID affixed to the analyte sensor system and manually enter the transmitter ID into the one or more display devices to establish the secure connection. Such embodiments can further require a user to remember this transmitter ID to establish future secure connections with one or more other display devices. Establishing secure communications in this manner can be time consuming (e.g., taking 5 to 30 minutes to establish) and can provide a sub-optimal user experience.

Accordingly, some embodiments are disclosed herein where a display device is configured to utilize a light emitting source to transmit the transmitter ID, or another secret key associated with the analyte sensor system, to initiate a secure pairing process between the display device and the analyte sensor system. As will become apparent from the description below, such embodiments provide a solution that does not require the user to read the transmitter ID and manually enter it into the display device, allowing secure communications to be established faster and with less user intervention, thereby providing a more streamlined user experience.

Figure 18:
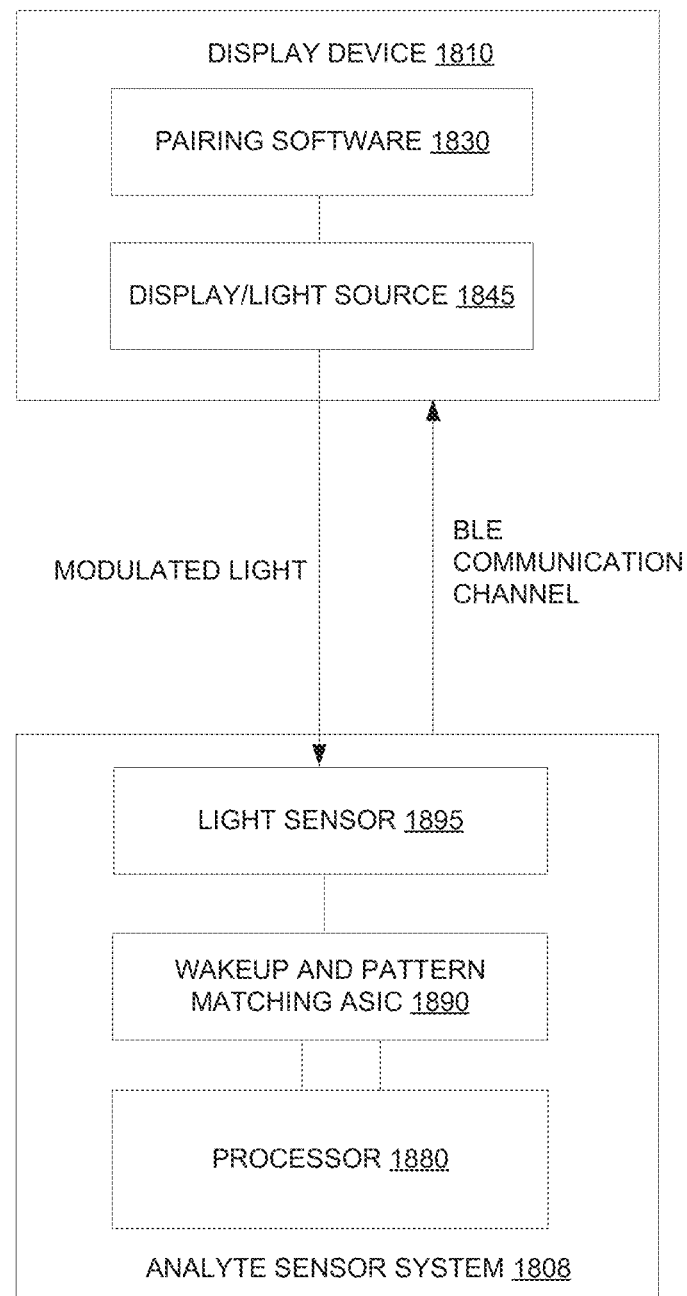
FIG. 18 illustrates aspects of an example system that can be used in connection with implementing embodiments of the disclosure.

FIG. 18 illustrates a block diagram of several features of a system for wirelessly communicating analyte sensor data, according to some example embodiments. FIG. 18 includes a display device 1810 and an analyte sensor system 1808. Display device 1810 can correspond to any display device described herein, for example display device 310 of FIG. 3B. Accordingly, display device 1810 can include any or all of the elements previously described in connection with any such corresponding display device. Analyte sensor system 1808 can correspond to any display device described herein, for example analyte sensor system 308 of FIG. 3B. Accordingly, analyte sensor system 1808 can include any or all elements previously described in connection with any such corresponding analyte sensor system.

Display device 1810 is illustrated as further comprising pairing software 1830 configured to carry out communication protocols at least as described herein for establishing a secure communication with at least analyte sensor system 1808. Pairing software 1830 can correspond to a portion of analyte sensor app 330 of FIG. 3B or can be software configured separately therefrom.

Display device 1810 further comprises a display and/or light source 1845 (e.g., a light emitting diode, a flash, an infra-red blaster, or any other suitable light emitting source) configured to display a pattern of modulated light configured to transmit information to analyte sensor system 1808 at least related to the process of establishing the secure communication with display device 1810 as will be described below. In some cases, the modulated light is light in the spectrum visible to the human eye. However, the present disclosure is not so limited and the modulated light can be light in any portion of the electromagnetic spectrum such as infra-red light.

Display device 1810 can be further configured to communicate with at least analyte sensor system 1808 on a communication channel separate from the modulate light communications, for example, BLE, Wi-Fi, NFC, cellular, or any other suitable communication protocol, as will be described in more detail below. Such a separate communication channel can provide secure communications between display device 1810 and analyte sensor system 1808 upon its establishment.

Analyte sensor system 1808 is illustrated as further comprising light sensor 1805 configured to sense and/or receive modulated light encoding at least one of a wakeup signal and a first security code associated with display device 1810 from display/light source 1845 of display device 1810.

Analyte sensor system 1808 further comprises a processor/ASIC 1890 configured to receive an indication of the wakeup signal and the first security code from light sensor 1895. Processor/ASIC 1890 can be configured to detect and/or otherwise recognize the wakeup signal and transmit an interrupt or wake signal to a second processor 1880 responsive to the detection and/or recognition. The interrupt and/or wakeup signal can be configured to wake up at least a portion of the second processor 1880. Processor/ASIC 1890 can be further configured to pass the received first security code to second processor 1880 for verification, further processing, or use in further processing of other data. In some embodiments, processor/ASIC 1890 can correspond to one or more processors and/or wakeup detection circuits as previously described in connection with FIG. 4, for example, AFE 410, processor 420 or at least a portion of radio 425. In some embodiments, second processor 1880 can correspond to processor 380 as previously described in connection with FIG. 3B.

Responsive to receipt of the first security code, second processor 1880 can be configured to encrypt a second security code utilizing the first security code and cause the encrypted second security code to be broadcasted to display device 1810 via a method or communication protocol other than the modulate light communications, for example, BLE, Wi-Fi, NFC, cellular, or any other suitable communication protocol. The second security code can be a unique security code corresponding to and/or associated with analyte sensor system 1808.

Responsive to receipt of the encrypted second security code, display device 1810 can be configured to validate the encrypted second security code utilizing any suitable validation method or protocol. Based on the validation, display device 1810 can be configured to start secure communication with analyte sensor system 1808 via a communication protocol other than the modulate light communications, for example, BLE, Wi-Fi, NFC, cellular, or any other suitable communication protocol. Upon establishment of the secure communication with analyte sensor system 1808, analyte sensor system 1808 can be configured to transmit at least analyte concentration data encrypted utilizing the second security code or utilizing another security code display device 1810 is configured to decrypt. Accordingly, embodiments according to FIG. 18 can advantageously allow secure pairing and subsequent communication between display device 1810 and analyte sensor system without a user having to manually read and/or enter a transmitter ID into either display device 1810 or analyte sensor system 1808.

Figure 19A:
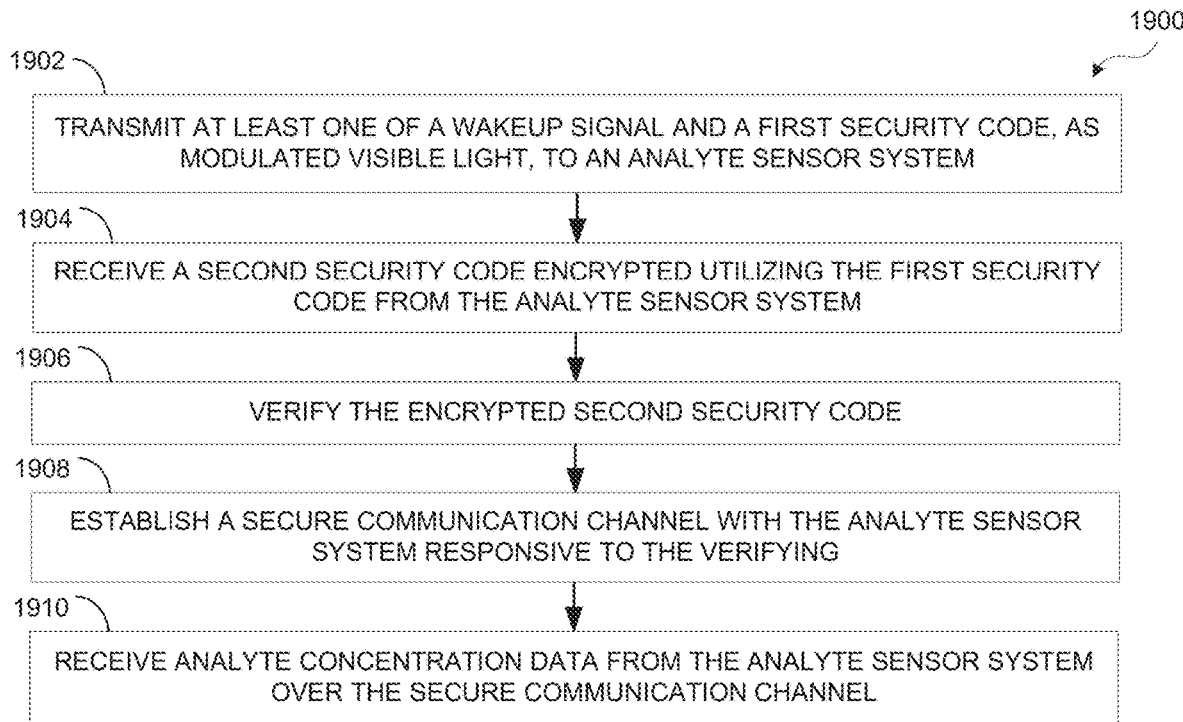
FIG. 19A is an operational flow diagram illustrating various operations that can be performed in accordance with embodiments of the disclosure.

Description now turns to flowchart 1900 of FIG. 19A, describing operations of, for example, any display device described herein with respect to embodiments previously described in connection with FIG. 18. Block 1902 includes transmitting at least one of a wakeup signal and a first security code, as modulated visible light, to an analyte sensor system. For example, display device 1810 can be configured to transmit the wakeup signal and the first security code, corresponding to and/or associated with display device 1810, via display/light source 1845, to analyte sensor system 1808.

Block 1904 includes receiving a second security code encrypted utilizing the first security code from the analyte sensor system. For example, display device 1810 can be configured to receive the second security code, encrypted utilizing the first security code. In some embodiments, display device 1810 can receive the encrypted second security code responsive to transmitting the wakeup signal and the first security code to analyte sensor system 1808 and/or responsive to analyte sensor system 1808 receiving the wakeup signal and the first security code. In some embodiments, the encrypted second security code can be received via a communication channel and/or utilizing a different communication protocol than the modulated visible light, for example, BLE, Wi-Fi, NFC, cellular, or any other suitable communication protocol.

Block 1906 includes verifying the encrypted second security code. For example, display device 1810 can be configured to verify that the second security code corresponds to a predetermined, previously known or otherwise determinable security code and/or that the second security code was encrypted utilizing the first security code corresponding to and/or associated with display device 1810.

Block 1908 includes establishing a secure communication channel with the analyte sensor system responsive to the verifying. For example, upon verifying the encrypted second security code, display device 1810 can be configured to establish a secure communication channel utilizing a different communication protocol than the modulated visible light, for example, BLE, Wi-Fi, NFC, cellular, or any other suitable communication protocol.

Block 1910 includes receiving analyte concentration data from the analyte sensor system over the secure communication channel. For example, in some embodiments, display device 1810 can be configured to receive analyte concentration data, encoded utilizing the second security code corresponding to and/or associated with analyte sensor system 1808, from analyte sensor system 1808 over the BLE communication channel.

Figure 19B:
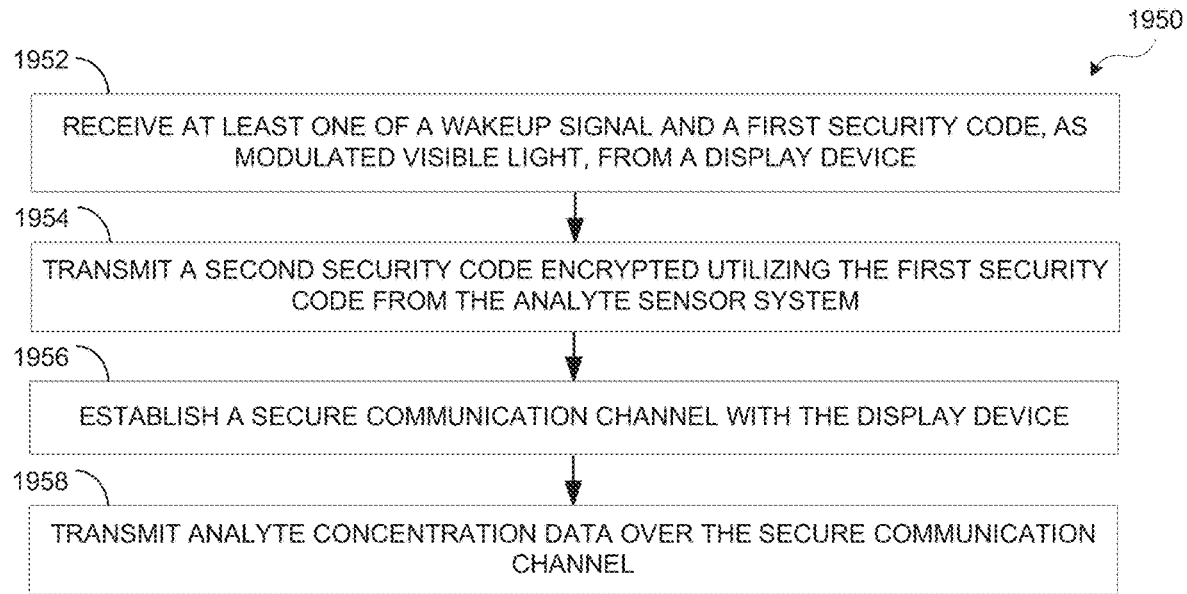
FIG. 19B is an operational flow diagram illustrating various operations that can be performed in accordance with embodiments of the disclosure.

Description now turns to flowchart 1950 of FIG. 19B, describing operations of, for example, any analyte sensor system described herein with respect to embodiments previously described in connection with FIG. 18. Block 1952 includes receiving at least one of a wakeup signal and a first security code, as modulated visible light, from a display device. For example, analyte sensor system 1808 can be configured to receive the wakeup signal and the first security code, corresponding to and/or associated with display device 1810, via light sensor 1895, from display device 1810.

Block 1954 includes transmitting a second security code encrypted utilizing the first security code from the analyte sensor system. For example, analyte sensor system 1808 can be configured to transmit the second security code, encrypted utilizing the first security code. In some embodiments, analyte sensor system can transmit the encrypted second security code responsive to receiving the wakeup signal and the first security code. In some embodiments, the encrypted second security code can be transmitted via a communication channel and/or utilizing a different communication protocol than the modulated visible light, for example, BLE, Wi-Fi, NFC, cellular, or any other suitable communication protocol.

Block 1956 includes establishing a secure communication channel with the display device. For example, analyte sensor system 1808 can be configured to establish or participate in the establishment of a secure communication channel with display device 1810 utilizing a different communication protocol than the modulated visible light, for example, BLE, Wi-Fi, NFC, cellular, or any other suitable communication protocol.

Block 1958 includes transmitting analyte concentration data over the secure communication channel. For example, in some embodiments, analyte sensor system 1808 can be configured to transmit analyte concentration data, encoded utilizing the second security code corresponding to and/or associated with analyte sensor system 1808, to display device 1810 over the BLE communication channel.

User Alert for Inability to Connect an Analyte Sensor System to a Detected Display Device Several embodiments are disclosed herein where an analyte sensor system is configured to transmit sensor data to a paired display device (e.g., a smart phone or a smart watch) such that a user can easily view the sensor data on the display device. In some embodiments, transmitting this sensor data to the display device is performed periodically and/or intermittently to reduce average power consumption of the analyte sensor system. Accordingly, the display device can periodically connect with and disconnect from the analyte sensor system. However, there can be instances where the user is wearing the analyte sensor system while the display device is nearby, but the display device is unable to connect with the analyte sensor system, preventing sensor data and/or other data from being transmitted from the analyte sensor system to the display device or vice versa. One common cause of such inability to connect is low signal strength (SSI) between the display device and the analyte sensor system. Such low signal strength can have a variety of causes, including but not limited to radio frequency (RF) obstructions, a user laying on the analyte sensor system or other RF interference. Accordingly, the present disclosure contemplates alerting a user of a display device when the display device detects an advertisement message from an analyte sensor system but is unable to connect with the analyte sensor system, thereby allowing the user to perform one or more actions likely to increase the probability of establishing a connection during a next attempt.

Figure 20:
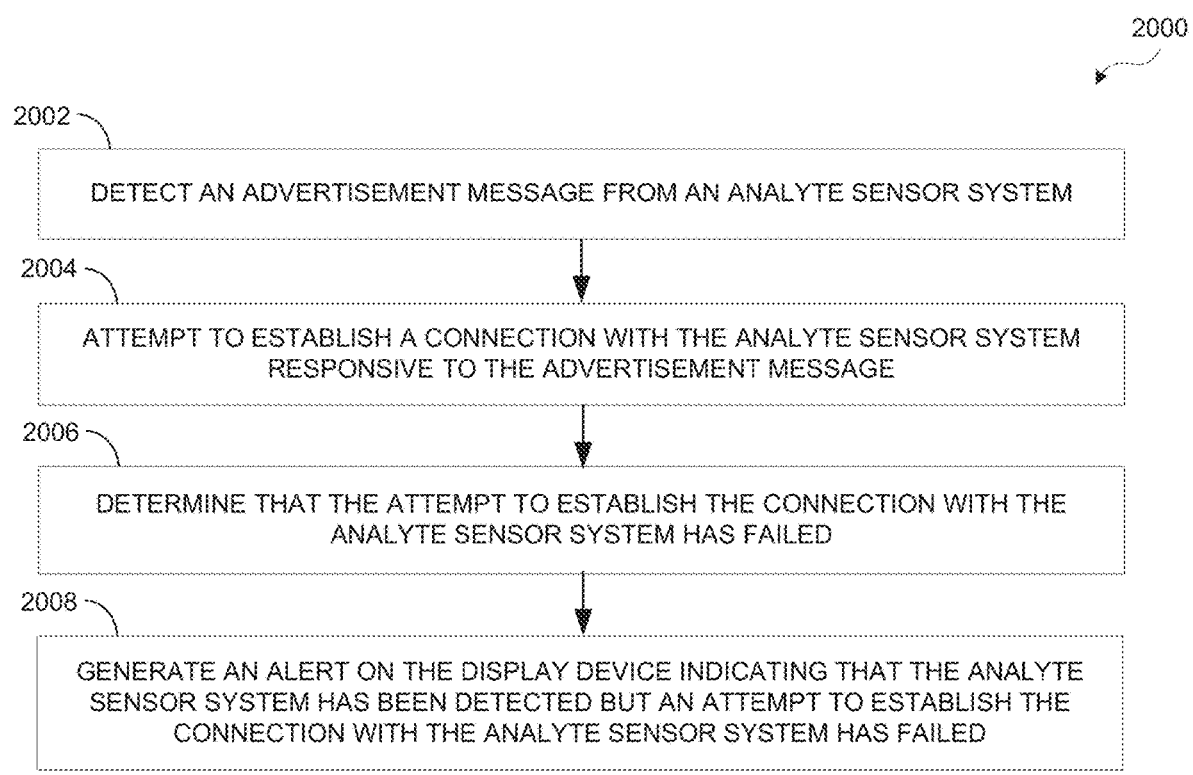
FIG. 20 is an operational flow diagram illustrating various operations that can be performed in accordance with embodiments of the disclosure.

FIG. 20 illustrates a flowchart 2000 describing operations of, for example, any display device described herein with respect to alerting a user when the display device detects an advertisement message from any analyte sensor system described herein but is unable to connect with the analyte sensor system.

Block 2002 includes detecting an advertisement message from an analyte sensor system. For example, any display device described herein can detect an advertisement message from any analyte sensor system described herein.

Block 2004 includes attempting to establish a connection with the analyte sensor system responsive to the advertisement message. For example, the display device can be configured to attempt to establish a connection with the analyte sensor system according to any pairing and/or connection protocol disclosed herein or according to any other suitable pairing and/or connection protocol.

Block 2006 includes determining that the attempt to establish the connection with the analyte sensor system has failed. For example, after a predetermined period of time attempting but failing to establish the connection with the analyte sensor system, the display device can be configured to make a determination that the attempt to establish the connection with the analyte sensor system has failed.

Block 2008 includes generating an alert on the display device indicating that the analyte sensor system has been detected but an attempt to establish the connection with the analyte sensor system has failed. For example, the display device can be configured to generate any appropriate alert, for example and not limitation, "Hi [User], Your [smartphone/smartwatch] is able to see your [analyte sensor system/transmitter] somewhere in your vicinity, however, was not able to connect to it to receive data. Please try changing your orientation with respect to your [smartphone/smartwatch] and other possible RF obstructions within [5 minutes] so that the next connection attempt has a better chance of success." In some embodiments, the alert can further comprise at least one suggested user intervention for improving the probability of establishing the connection with the analyte sensor system on a subsequent connection attempt.

Direct Pairing of a Smartwatch or Other Display Directly to an Analyte Sensor System In some cases, a user of an analyte sensor system may want to pair the analyte sensor system with more than one display device, for example, a smartphone and a smartwatch. For example, it can be more convenient to view analyte concentration data on a smaller display device worn by the user, such as a smartwatch. However, while potentially easier to view analyte concentration data and/or alerts at a glance, it can be more cumbersome to input information or to initiate pairing processes in such smaller display devices due at least in part to more limited user input functions, e.g., the inability or difficulty of providing a full keyboard or numeric pad on their smaller displays. Accordingly, several embodiments are contemplated that allow direct, secure pairing of a display device, such as a smartwatch, with an analyte sensor system without requiring a user to manually enter a transmitter ID, serial number or code associated with the analyte sensor system into the smartwatch for either initial pairing or subsequent connection and/or reconnection with the analyte sensor system. Description of such embodiments follows with reference to at least FIGS. 3A-3C. For the purpose of illustration only, a smartphone and a smartwatch (examples of display devices 310 as previously described in connection with FIGS. 3A-3C) can both connect with analyte sensor system 308. For ease of representation, a first display device, e.g., a smartphone, can correspond to display device 310a, while a second display device, e.g., a smartwatch, can correspond to display device 310b.

Analyte sensor system 308 can already be paired and/or otherwise connected with display device 310a (e.g., a smartphone). To initiate connection of display device 310b (e.g., a smartwatch) to analyte sensor system 308, a user can select an option to add a display device on the analyte monitoring application on display device 310a (e.g., analyte sensor app 330 of FIG. 3B). Selecting the option to add display device 310b on an app running on display device 310a can be an easier user interaction, since a display on display device 310a can be larger than a display on display device 310b. However, the present disclosure is not so limited, and a user could alternatively select an option to add a display device on a similar analyte sensor app 330 running on display device 310b. In some embodiments, analyte sensor app 330 can include a filtering option that determines or limits what types of smartwatches or other display devices the user can pair with analyte sensor system 308 based on display device functionality, versions, and/or compatibility (e.g., 3E, 4G, LTE, 5G, Wi-Fi, NFC, Bluetooth, BLE support, etc.). The filtering option, for example, may also provide an indication whether the analyte sensor system 308 can support a direct-to-watch communication with a display device (e.g., a smartwatch). For example, upon selecting the option to add display on the analyte sensor app 330 (e.g., on the display 310a), a signal or a feedback message may be presented on the app notifying the user that the analyte sensor system 308 is not compatible with display device 310b, and/or cannot support a direct-to-watch communication. For example, this may be because the version or model of the analyte sensor system 308 does not support a direct-to-watch feature or the firmware running on the analyte sensor system 308 may be out of date. Alternatively, in some examples, if the analyte sensor system 308 can support a direct-to-watch communication with display device 310b (e.g., a smartwatch), a feedback message on the app, upon selection of the option to add a display (e.g., display device 310b), may indicate that the analyte sensor system 308 can support a direct-to-watch communication. In one example, this may be because the analyte sensor system 308 is of the correct version/model and/or has the correct/up-to-date firmware version.

Further in some examples, instead of a signal or a feedback message, the option of selecting a display in the analyte sensor app 330 may be greyed out, if the analyte sensor system 308 (that is already in communication with display 310a) cannot support a direct-to-watch communication, thus not allowing the user to select such an option. Yet in another example, the option may not be greyed out, if the analyte sensor system 308 (that is already in communication with display 310a), for example, can support a direct-to-watch communication with a new display device 310b (e.g., a smartwatch).

Responsive to the user selection to add a display device, display device 310a or display device 310b can transmit a signal or message to analyte sensory system 308 indicating that a new device has requested pairing.

Responsive to the signal or message indicating a new device has requested pairing, analyte sensor system 308 can enter a pairing mode in which analyte sensor system 308 is configured to transmit advertisement messages periodically or continuously for a predetermined interval of time. In some embodiments, the predetermined period of time during which analyte sensor system 308 periodically advertises for connection with display device 310b (e.g., a smartwatch) is significantly longer than it would otherwise be for another type of display device (e.g., for a smartphone, etc.), for example, 10 minutes versus 20 seconds. However, the present disclosure is not so limited and predetermined period of time can be substantially the same as for any other type of display device. In another example, the analyte sensor system 308 may not enter a pairing mode responsive to the signal or message indicating a new device has requested pairing. Instead, analyte sensor system 308 may solicit connection from the new display device until its whitelist is full. In such an example, the predetermined period time may vary (e.g., it can be longer, shorter or the same).

Responsive to detecting, identifying and/or receiving the advertisement message, display device 310b can display a "pair" notification that the user selects to initiate the pairing process. Accordingly, display device 310b can be configured to receive an input from the user that initiates the pairing process in response to displaying the "pair notification."

Optionally, responsive to receiving the input from the user that initiates the pairing process, display device 310b can transmit a signal to display device 310a indicating the input has been received from the user.

Display device 310a can transmit pairing and/or authentication information (e.g., a transmitter ID or serial number corresponding to analyte sensor system 308, and/or one or more pairing and/or encryption keys) to display device 310b. In this way, a user is not required to enter the transmitter ID or any other similar identifying information corresponding to analyte sensor system 308 into display device 310b to allow pairing. In one example, this may be performed responsive to receiving the signal from display device 310b indicating the input has been received from the user.

In some other embodiments, display device 310b can be configured to receive some or all of the pairing and/or authentication information from a separate server, for example server system 334 of FIG. 3A. In such embodiments, one might contemplate that the sever and display device 310b have established a communication channel that has been previously authenticated, which may be based on authentication information provided by display device 310a. In such embodiments, responsive to receiving the input from the user that initiates the pairing process, display device 310b can transmit the signal indicating the input has been received from the user to server system 334 rather than or in addition to display device 310a.

Responsive to receiving the pairing and/or authentication information from display device 310a and/or server system 334, display device 310b can be configured to pair with analyte sensor system 308 according to any pairing protocol described herein or otherwise known. In some embodiments, this pairing process can be carried out in the background such that the user is not aware or notified of steps in the procedure not requiring explicit input from the user. Accordingly, a user can easily pair a smaller display device, such as a smartwatch, to analyte sensor system 308 without being required to enter identifying information for analyte sensor system 308 into the smartwatch, providing a more streamlined experience to the user. Once a successful pairing has been performed, it will be appreciated that the display device 310b will receive analyte related data from the analyte sensor system 308 and provide such data and/or information related to the analyte data to the user (e.g., estimated glucose values, notifications, alarms, alerts, etc., as described herein).

Figure 21A:
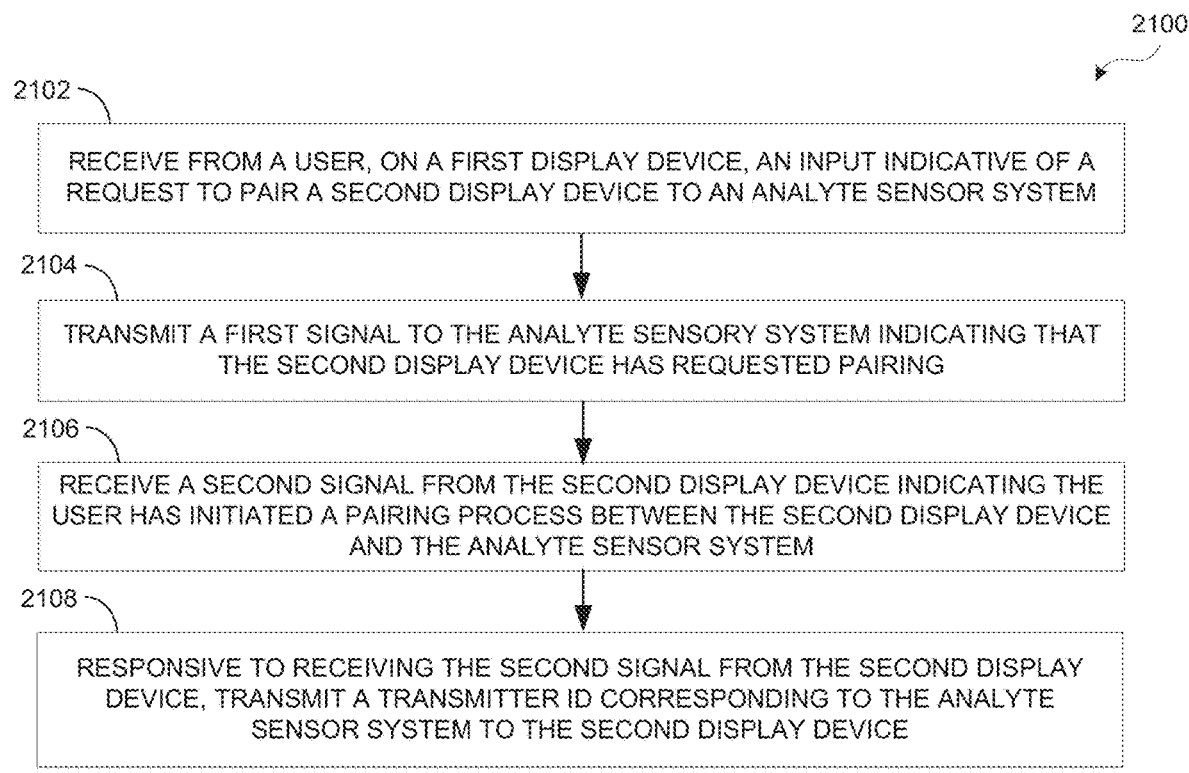
FIG. 21A is an operational flow diagram illustrating various operations that can be performed in accordance with embodiments of the disclosure.

Description now turns to flowchart 2100 of FIG. 21A, describing operations of, for example, a first display device 310a (e.g., a smartphone) as previously described above. Block 2102 includes receiving from a user, on a first display device, an input indicative of a request to pair a second display device to an analyte sensor system. For example, as previously described, a user can select an option to add a display device on the analyte monitoring application on display device 310a (e.g., analyte sensor app 330 of FIG. 3B). First display device 310a can already be paired and in communication with analyte sensor system 308.

Block 2104 includes transmitting a first signal to the analyte sensory system indicating that the second display device has requested pairing. For example, as previously described, display device 310a can transmit a first signal to analyte sensor system 308 indicating that display device 310b has requested pairing. As previously described, transmitting this signal to analyte sensor system 308 can cause analyte sensor system 308 to enter optionally a pairing mode in which analyte sensor system 308 periodically transmits advertisement messages for a predetermined interval of time.

Block 2106 includes receiving a second signal from the second display device indicating the user has initiated a pairing process between the second display device and the analyte sensor system. For example, as previously described, a user may acknowledge a "pair" notification displayed by display device 310b by providing user input to display device 310b, and display device 310b may or may not transmit a second signal indicating the user has initiated the pairing process to display device 310a.

Block 2108 includes, responsive to receiving the second signal from the second display device, transmitting a transmitter ID corresponding to the analyte sensor system to the second display device. For example, as previously described, responsive to receiving the second signal from display device 310b, display device 310a can transmit pairing and/or authentication information (e.g., a transmitter ID or serial number corresponding to analyte sensor system 308, and/or one or more pairing and/or encryption keys) to display device 310b. Display device 310b can use this pairing and/or authentication information to pair with analyte sensor system 308.

Figure 21B:
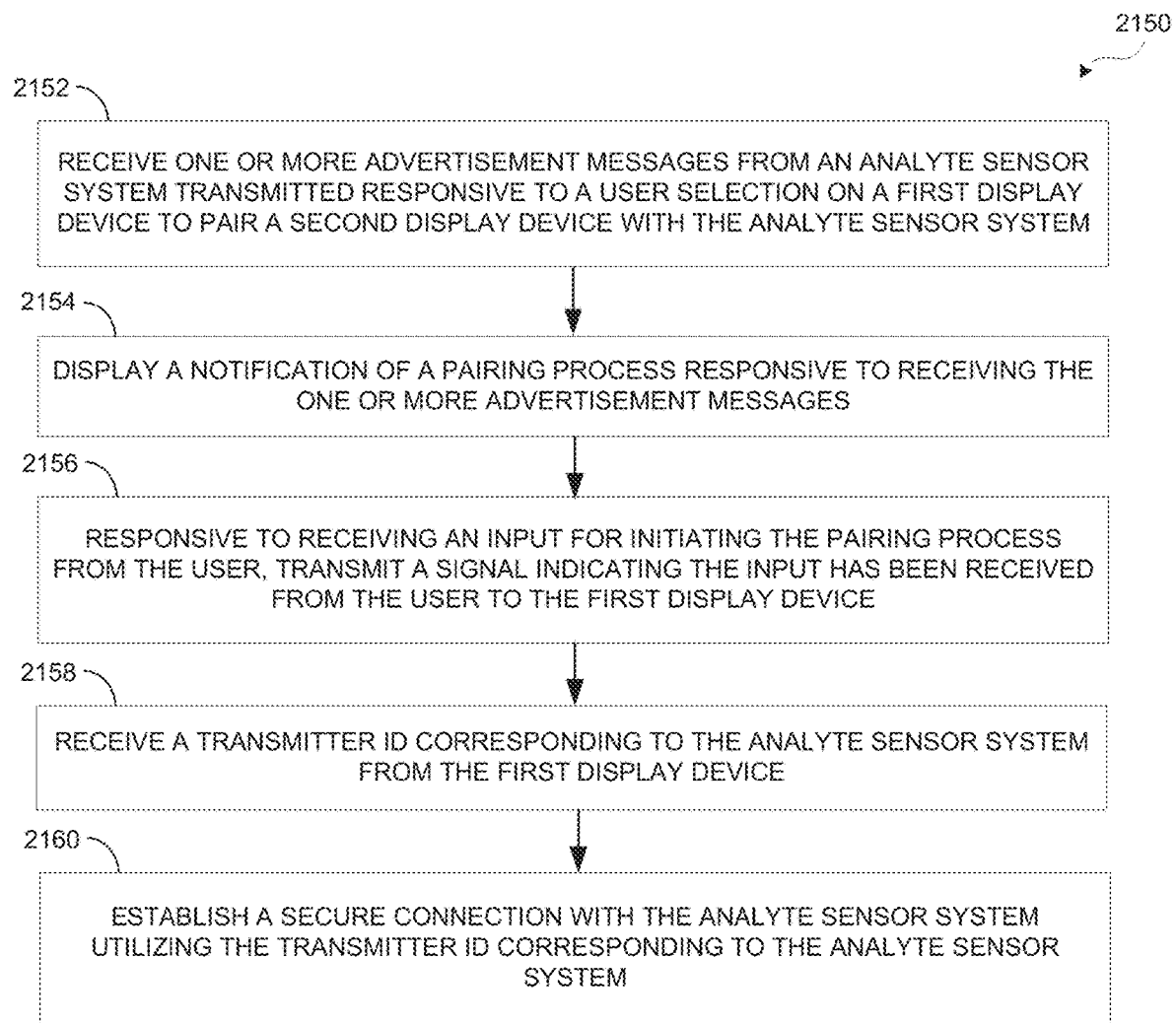
FIG. 21B is an operational flow diagram illustrating various operations that can be performed in accordance with embodiments of the disclosure.

Description now turns to flowchart 2150 of FIG. 21B, describing operations of, for example, a second display device 310*a* (e.g., a smartwatch) as previously described above. Block 2152 includes receiving one or more advertisement messages from an analyte sensor system transmitted responsive to a user selection on a first display device to pair a second display device with the analyte sensor system. For example, as previously described, a user can select an option to add a display device on analyte monitoring application 330 on display device 310*a* (FIG. 3B), and analyte sensor system 308 can be configured to optionally enter a pairing mode, transmitting advertisement messages periodically for a predetermined interval of time. In such embodiments, first display device 310*a* can already be paired with and in communication with analyte sensor system 308.

Block 2154 includes displaying a notification of a pairing process responsive to receiving the one or more advertisement messages. For example, as previously described, responsive to detecting, identifying and/or receiving the advertisement messages, display device 310*b* can display a "pair" notification to the user.

Block 2156 includes, responsive to receiving an input for initiating the pairing process from the user, optionally transmitting a signal indicating the input has been received from the user to the first display device. For example, as previously described, responsive to receiving the input from the user that initiates the pairing process, display device 310*b* may or may not transmit a signal to display device 310*a* indicating the input has been received from the user.

Block 2158 includes, receiving a transmitter ID corresponding to the analyte sensor system from the first display device. For example, as previously described, display device 310*a* can transmit and display device 310*b* can receive pairing and/or authentication information (e.g., a transmitter ID or serial number corresponding to analyte sensor system 308, and/or one or more pairing and/or encryption keys).

Block 2160 includes establishing a secure connection with the analyte sensor system utilizing the transmitter ID corresponding to the analyte sensor system. For example, as previously described, responsive to receiving the pairing and/or authentication information, display device 310*b* can be configured to pair with analyte sensor system 308 according to any pairing protocol described herein or known generally.

Data Capture

Description below references components at least as disclosed in FIGS. 3A-3E, however, the description is not so limited, and can correspond or apply to any other components described throughout this disclosure.

In some circumstances a user may want to couple more than one display device to their analyte sensor system (e.g., analyte sensor system 308), for example a smartphone and a wearable smartwatch, or their own personal smartphone or smartwatch and a medical device, for example, utilized by a health care provider in connection with managing a medical condition. Because it is desirable to preserve battery life of analyte sensor system 308, analyte sensor system 308 can be configured to initially pair and connect with a display device, transfer data to the display device, disconnect from the display device to enter a low-power and/or sleep mode to preserve battery, and then periodically reconnect to the display device based on a predetermined connection interval (e.g., every 5 minutes). While several embodiments described in this disclosure utilize a "predetermined" connection interval, the present disclosure also contemplates the use of similar connection intervals whose duration and/or frequency of occurrence are not predetermined. Accordingly, embodiments describing use of predetermined connection intervals also contemplate the use of such non-predetermined connection intervals. One way in which analyte sensor system 308 can manage connections to multiple display devices is to allow one display device to maintain a communication connection with analyte sensor system 308 during a given predetermined connection interval. While this allows for the sequential connection of multiple display devices in different predetermined connection intervals, it limits such connections in that no two display devices maintain a connection with analyte sensor system 308 at the same time during the same predetermined connection interval, which can cause long periods between reestablishing connections with a particular display device when multiple display devices are ultimately accommodated.

Another way in which analyte sensor system 308 can manage connection to multiple display devices is to operate utilizing a plurality of time slots in which different classifications of device are allowed to connect and communicate with analyte sensor system 308; for example, a consumer timeslot, in which display devices commonly utilized by a consumer (e.g., smart phones, smart watches, user receivers) are allowed to connect with analyte sensor system 308 one at a time, and a medical or professional timeslot, in which display devices and/or other proprietary or dedicated medical devices commonly utilized by a medical professional are allowed to connect with analyte sensor system 308 one at a time. Where such consumer and medical/professional timeslots are utilized, advertising parameters and protocols can be configured similarly or differently for advertising availability for connection within each timeslot. Such examples can further utilize multiple corresponding whitelists, on which respective consumer or medical/professional devices that have previously established and authenticated secure connections with analyte sensor system 308 are listed, to help manage connections of known or trusted display devices. In some embodiments, each such whitelist can include space for a single entry corresponding to a single, preferred consumer device (e.g., the user's smartphone) or a single, preferred medical/professional device (e.g., a doctor's associated health care provider device). If a user or medical professional wants to pair a new display device not currently on the corresponding whitelist, upon pairing of the new display device, the other display device previously on the whitelist would be removed from the whitelist and the newly paired display device added to the whitelist in its place in the single entry. However, when combined with the restriction that a single device can maintain a connection with analyte sensor system 308 during any predetermined connection interval, display devices, whether consumer-class or medical/professional-class, can still be required to wait significant amounts of time between connections with analyte sensor system 308.

Accordingly, several embodiments described below provide for multiple display devices to connect and maintain their connections concurrently during the same predetermined connection interval. General concepts described below include, separately or in any combination, removing a distinction between consumer and medical/professional classifications, whitelists, and timeslots and considering each display device to be of a similar classification, utilizing a single whitelist on which all types/classifications of trusted devices can be listed, and providing a single timeslot in which one or more compatible display devices can potentially pair and connect with analyte sensor system 308 during a same predetermined connection interval. In some embodiments, such a single whitelist can have an increased capacity from e.g., 2 entries—one entry for a medical/professional device and one entry for a consumer device—to e.g., 3 or more entries for any type or classification of compatible display device. Because a single timeslot is utilized for connection and communicating with analyte sensor system 308, advertising and connection maintenance can be handled simultaneously, or at least concurrently for multiple devices as occurring during the same predetermined connection interval. Since a whitelist can still be utilized, advertising can utilize a first set of parameters for general advertising, e.g., to advertise to display devices not yet listed on the whitelist, and a second set of parameters for whitelist advertising, e.g., to advertise to trusted display devices currently listed on the whitelist. Upon establishing a connection with each of one or more compatible display devices in the same predetermined communication interval, each of the one or more compatible display devices (e.g., display devices 310) can communication with analyte sensor system 308 and/or, in some cases, with one another and/or with another server (e.g., server system 334) during the same predetermined communication interval as described by any part of this description or as otherwise known. At some point during the predetermined communication interval, it can be determined that one or more connections should be closed or any number of reasons. Some embodiments, rather than immediately closing one or more connections responsive to a command or determination to close the one or more connections, contemplate maintaining those connections, albeit potentially during or for reduced connection intervals, until general advertising concludes for a particular predetermined connection interval. In addition, some embodiments contemplate tuning advertising parameters, connection parameters, and/or timeout strategies to save power, improve responsiveness, and/or to simplify operation of one or more devices involved. While a rogue device may hear advertising messages, such a rogue device would be expected to fail authentication and, therefore, be prevented from establishing a communication session or being added to a whitelist. Several features of such embodiments will now be described in more detail below.

Utilizing a Timeslot Agnostic Connection/Communication with an Analyte Sensor System In some embodiments, a single recurring or periodic timeslot is utilized, during which a plurality of compatible display devices 310 can potentially pair, connect and communicate with analyte sensor system 308. Such a single timeslot may not provide any distinction between consumer-class display devices and medical/professional-class display devices. Collapsing all timeslots and device classifications to a single variety (e.g., all compatible display devices are considered the same for connection purposes) reduces complexity and requirements associated with operating, advertising and connection management protocols for all devices involved. In addition, since only a single classification of display devices 310 is contemplated, in such embodiments, advertising protocols and/or parameters can also be simplified.

Utilizing a Generalized Whitelist for Connection/Communication with an Analyte Sensor System In some embodiments, a single or generalized whitelist is utilized, in which all compatible display devices 310 can potentially be listed once an initial pairing and authentication with analyte sensor system 308 has been performed. For example, where prior consumer and medical/professional whitelists have been utilized, each having space for a single display device entry, in some other embodiments, a single whitelist for all compatible display devices 310, having 3 or more entries for any type or classification of compatible display device 310, can be utilized. Including 3 or more entries in the whitelist allows multiple display devices to be whitelisted and easily reconnected as required for concurrent communication of analyte concentration and/or other data, for example, a user's smartphone, the user's smartwatch, and even a third display device, for example a medical professional's health care provider device during a same predetermined communication interval. In some embodiments, analyte sensor system 308 can be configured to remove or delete a display device from the whitelist based on not having received data from or not having transmitted data to the display device for a predetermined period of time or according to any other protocol for managing a whitelist as described anywhere in this disclosure or as otherwise known.

Figure 22A:
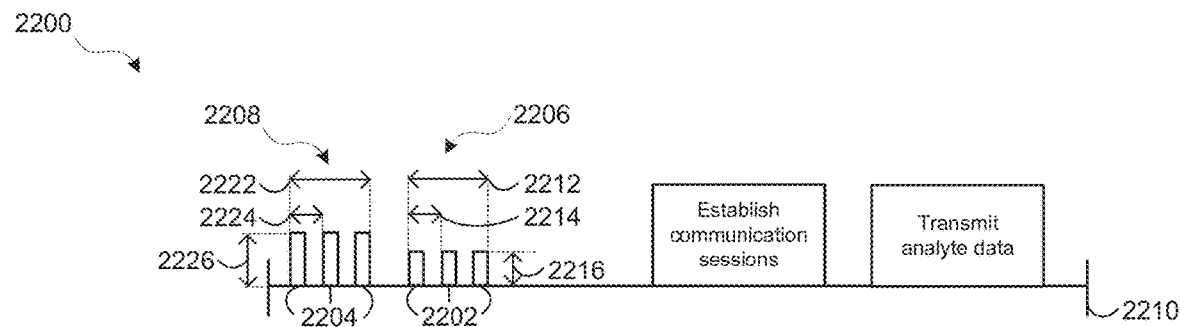
FIG. 22A is a signaling diagram illustrating various operations that can be performed in accordance with embodiments of the disclosure.
Figure 22B:
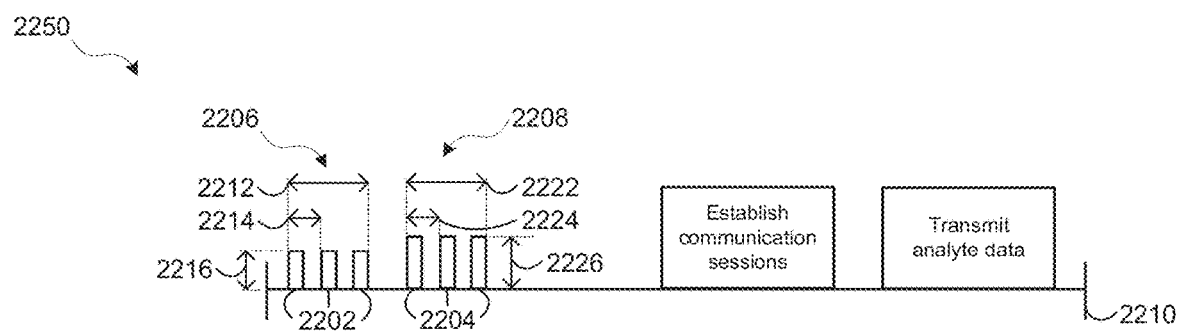
FIG. 22B is a signaling diagram illustrating various operations that can be performed in accordance with embodiments of the disclosure.
Figure 23:
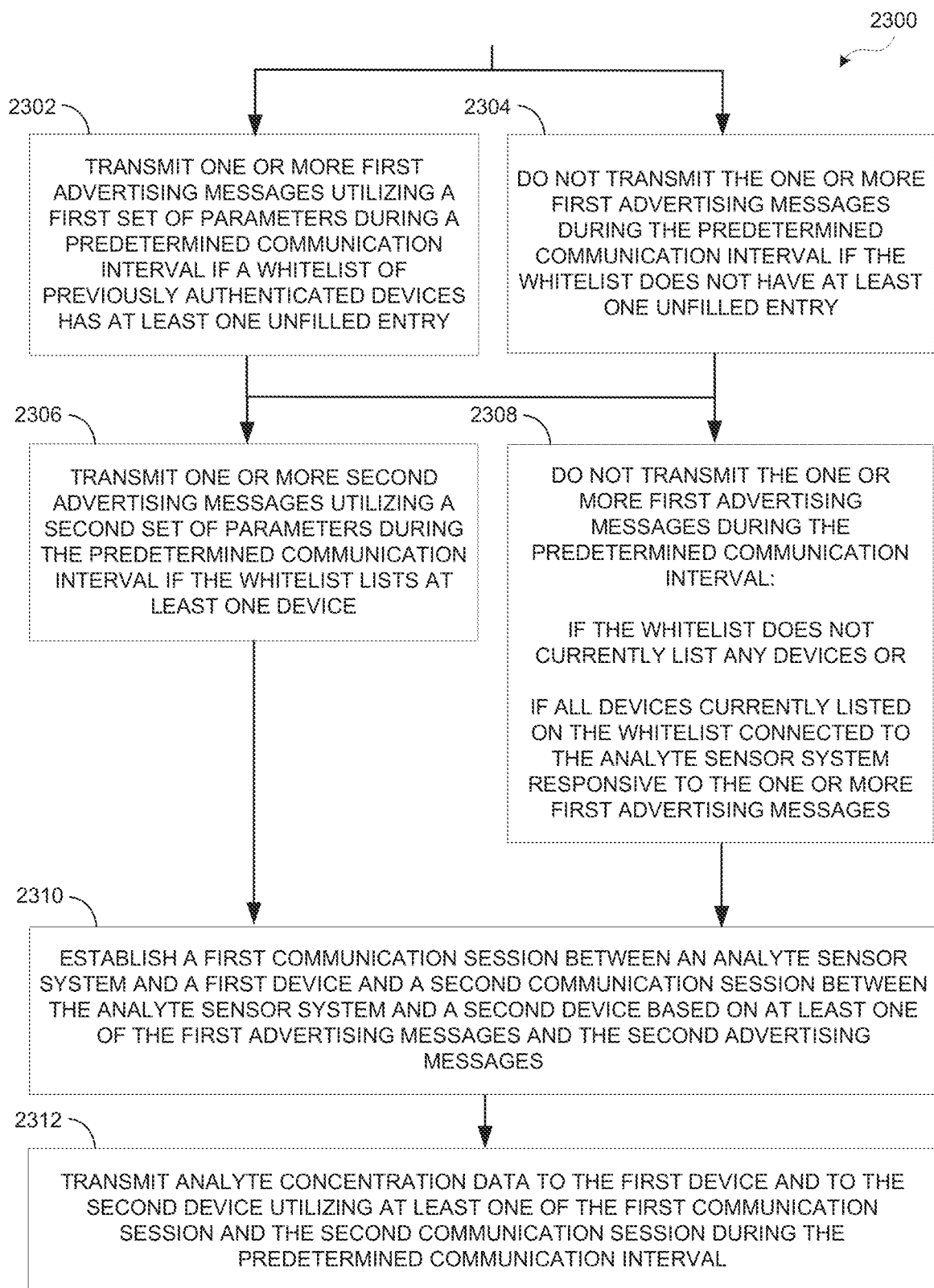
FIG. 23 is an operational flow diagram illustrating various operations that can be performed in accordance with embodiments of the disclosure.

Advertising Based on a Single Whitelist for Connection with an Analyte Sensor System Discussion in this section will refer to FIGS. 3A-3C, FIGS. 22A and 22B, and FIG. 23. FIGS. 22A and 22B illustrate example timing diagrams 2200, 2250 for advertising signaling, according to some embodiments, while FIG. 23 illustrates an example flowchart for advertising signaling by analyte sensor system 308, according to some embodiments.

To pair, connect and/or reconnect with analyte sensor system 308, advertising can be performed, in which advertisement messages 2202, 2204 are transmitted periodically during one or more advertising intervals 2206, 2208 to announce the availability of the advertising device for pairing, connection and/or reconnection during a given predetermined connection interval 2210. In some embodiments utilizing a single whitelist, first advertising messages 2202 can utilize a first set of parameters for discovering and/or advertising to new display devices 310 not currently listed on the whitelist. This first set of parameters can define one or more of a first duration 2212 of a first advertising interval 2206, a first periodic interval 2214 utilized to transmit advertising messages 2202 within first advertising interval 2206, a first power 2216 at which first advertising messages 2202 are transmitted, and any other parameters for transmitting first advertising messages 2202. Such a first set of parameters can correspond to general or discovery advertising for devices not currently whitelisted.

Such advertising can additionally utilize second advertising messages 2204 utilizing a second set of parameters for discovering and/or advertising to display devices 310 currently listed on the whitelist. This second set of parameters can define one or more of a second duration 2222 of a second advertising interval 2208, a second periodic interval 2224 utilized to transmit advertising messages 2204 within second advertising interval 2208, a second power 2226 at which second advertising messages 2204 are transmitted, and any other parameters for transmitting second advertising messages 2204. Such a second set of parameters can correspond to whitelist or reconnection advertising. Utilizing the first and second sets of advertising parameters for respective first and second advertising messages 2202, 2204 allow general and reconnection advertising in the same communication timeslot.

In some embodiments, first power 2216 at which general advertising messages 2202 are transmitted can be lower than second power 2226 at which reconnection advertising messages 2204 are transmitted. For example, a user attempting to pair and connect a new display device 310, e.g., a smartphone or smartwatch, is likely to have the new display device 310 disposed in close proximity to analyte sensor system 308 (e.g., within a few feet). Such general advertising need not utilize a maximum, e.g., 30-meter, transmission power at least due to the close proximity of new display device 310 and analyte sensor system 308. By contrast, it can be desirable to keep whitelisted display devices 310 connected or to reconnect them, even when those whitelisted devices are a significantly greater distance from analyte sensor system 308, e.g., a smartphone left on a table while the user walks into another room momentarily. However, the present disclosure is not so limited and first power 2216 and/or second power 2226 can be configurable or reconfigurable to have any suitable absolute values and/or any suitable relative values with respect to the other.

In some embodiments, first duration 2212 of first advertising interval 2206 and/or first periodic interval 2214 utilized to transmit advertising messages 2202 within first advertising interval 2206 for general advertising can be different from second duration 2222 of second advertising interval 2208 and/or second periodic interval 2224 utilized to transmit advertising messages 2204 within second advertising interval 2208 for reconnection advertising. In addition, a first frequency of occurrence of first advertising interval 2206 can be different from a second frequency of occurrence of second advertising interval 2208. For example, analyte concentration data can be measured, processed or communicated every 30 seconds or every minute. Accordingly, in such embodiments, the second frequency of occurrence of second advertising interval 2208 can correspond to this timeframe and associated frequency of occurrence, e.g., every 30 seconds or every minute. However, it may not be necessary or desirable to attempt to "discover" new display devices not currently on the whitelist, that may or may not be present, on such short intervals, e.g., at the second frequency of occurrence. Accordingly, the first frequency of occurrence of first advertising interval 2206, associated with general advertising, can be lower than the second frequency of occurrence of second advertising interval 2208, associated with reconnection advertising. Utilizing a longer interval between general advertising intervals can save power within analyte sensor system 308 by reducing a number of times or a frequency of general advertising.

In addition, in some embodiments, analyte sensor system 308 and/or one or more already connected display devices 310 can further comprise a button or other user input that allows a user to initiate a general advertisement session on demand, for example, when the user wants to pair and connect a new display device 310 to analyte sensor system 308, e.g., the user's smartphone or smartwatch.

Description now turns to flowchart 2300 of FIG. 23, describing advertising operations of, for example, analyte sensor system 308, according to some embodiments. Block 2302 includes transmitting one or more first advertising messages utilizing a first set of parameters during a predetermined communication interval if a whitelist of previously authenticated devices has at least one unfilled entry. For example, during predetermined connection interval 2210, based on no display devices being listed on such a whitelist or based on the whitelist having at least one unfilled entry, analyte sensor system 308 can be configured to transmit one or more first advertising messages 2202 utilizing a first set of parameters, for example, defining one or more of first duration 2212 of first advertising interval 2206, first periodic interval 2214 utilized to transmit first advertising messages 2202 within first advertising interval 2206, first power 2216 utilized to transmit first advertising messages 2202, and any other parameters for such advertising. Such a first set of parameters can correspond to discovery, or general advertising for devices not currently listed on the whitelist.

In some embodiments, when analyte sensor system 308 is first powered up, analyte sensor system 308 can be configured to perform a pairing advertisement in which duration 2212 of first advertising interval 2206 is e.g., 15 minutes or less, although the present disclosure is not so limited, and duration 2212 of first advertising interval 2206 can be any suitable interval. Because of the shorter advertising interval compared to some other potential implementations, such an advertisement may be considered a fast pairing advertisement. In such embodiments, first periodic interval 2214 can be, e.g., 1024 msec, although the present disclosure is not so limited, and first periodic interval 2214 can be any suitable interval. In such embodiments, the "fast pairing advertisement" mode ends upon any display device "completing," e.g., successfully pairing and authenticating with analyte sensor system 308. Upon expiration of first advertising interval 2212 or the completion of any display device, advertising can follow any advertising protocol described herein or otherwise known.

Block 2304 includes not transmitting the one or more first advertising messages during the predetermined communication interval if the whitelist does not have at least one unfilled entry. For example, in some embodiments, if there are no entries available on the whitelist there can be no room for an additional device to connect. Accordingly, in such embodiments, analyte sensor system 308 can be configured to not perform general advertising to save power.

Block 2306 includes transmitting one or more second advertising messages utilizing a second set of parameters during the predetermined communication interval if the whitelist lists at least one device. For example, during predetermined connection interval 2210, based on at least one display device 310 being listed on the whitelist, analyte sensor system 308 can be configured to transmit one or more second advertising messages 2204 utilizing a second set of parameters for example, defining second duration 2222 of second advertising interval 2208, second periodic interval 2224 utilized to transmit second advertising messages 2204 within second advertising interval 2208, second power 2226 utilized to transmit advertising messages, and any other parameters for such advertising. Such a second set of parameters can correspond to reconnection advertising for display devices currently listed on the whitelist.

Block 2308 includes not transmitting the one or more second advertising messages during the predetermined communication interval if the whitelist does not currently list any devices or if all devices currently listed on the whitelist connected to the analyte sensor system responsive to the one or more first advertising messages. For example, if there are no currently whitelisted devices, there would not be a need for reconnection advertising. In some embodiments, for example as shown in FIG. 22B, analyte sensor system 308 can transmit one or more general advertising messages (e.g., 2202) utilizing the first set of parameters before transmitting one or more reconnection advertising messages (e.g., 2204) utilizing the second set of parameters in the same predetermined connection interval. In such embodiments, performing general advertising for new devices before performing reconnection advertising can also allow currently whitelisted devices to reconnect with analyte sensor system 308 during the general advertising interval (e.g., 2206) as well as allow the discovery and paring of additional new display devices during the general advertising interval (e.g., 2206) in the same predetermined connection interval. Moreover, where all such whitelisted devices are in range and have reconnected with analyte sensor system 308 during general advertising interval 2206, analyte sensor system 308 can be configured to delay or not transmit the subsequent reconnection advertisements 2204 during predetermined connection interval 2210, thereby allowing analyte sensor system 308 to further save power.

In some embodiments, for example as shown in FIG. 22A, analyte sensor system 308 can transmit one or more general advertising messages (e.g., 2202) utilizing the first set of parameters after transmitting one or more reconnection advertising messages (e.g., 2204) utilizing the second set of parameters. In such embodiments, performing general advertising for new devices after performing reconnection advertising for currently whitelisted devices can allow for the discovery and pairing of additional display devices after connection of currently whitelisted display devices. This is in contrast to some prior embodiments where advertisement would not continue after connecting a single whitelisted display device because the prior consumer or medical/professional whitelist would not have had another entry for additionally whitelisting a further display device and because such prior embodiments only provided for connection of a single display device with analyte sensor system 308 during a particular predetermined connection interval.

Block 2310 includes establishing a first communication session between an analyte sensor system and a first device and a second communication session between the analyte sensor system and a second device based on at least one of the first advertising messages and the second advertising messages. For example, as illustrated in FIGS. 22A and 22B, based on at least one of first advertising messages 2202 and second advertising messages 2204, analyte sensor system 308 can be configured to establish a first communication session with a first device (e.g., display device 310a of FIG. 3C) and a second communication session with a second device (e.g., display device 310b of FIG. 3C).

Block 2312 includes transmitting analyte concentration data to the first device and to the second device utilizing at least one of the first communication session and the second communication session during the predetermined communication interval. For example, as illustrated in FIGS. 22A and 22B, utilizing at least one of the first communication session and the second communication session during predetermined communication interval 2210, analyte sensor system 308 can be configured to transmit analyte concentration data to first device 310a and to second device 310b. Accordingly, both the first and second communication sessions can be kept open concurrently.

Communicating/Backfilling Data During a Communication Session

In some embodiments, where a first display device 310a (e.g., a smartphone, see FIG. 3C) and a second display device 310b (e.g., a smartwatch, see FIG. 3C) are both connected to analyte sensor system 308 during the same predetermined connection interval, for example as described above in connection with at least FIGS. 22A-23, analyte sensor system 308 can transmit data to and/or receive data from first display device 310a and second display device 310b in any manner described anywhere in this description or as otherwise known. In some embodiments, alarm data may also be transmitted by analyte sensor system 308 along with sensor data to one or both of display devices 310a, 310b.

In some embodiments, upon establishing a connection with analyte sensor system 308, connected display devices 310a, 310b can be configured to display an icon, for example on display 345, indicating display device 310a, 310b is connected. In addition, analyte sensory system 308 can transmit one or more alarm indications to first display device 310a for processing and second display device 310b can be configured to display an associated alarm notification to the user based on receiving an indication of the alarm from first display device 310a. In other embodiments, one or more alarm indications can be transmitted from analyte sensor system 308 directly to second display device 310b and second display device 310b can be configured to display an associated alarm notification to the user based on receiving and/or processing the alarm.

In some embodiments, multiple display devices 310a, 310b can be concurrently connected to analyte sensor system 308 and can generally communicate data between analyte sensor system 308 and display devices 310a, 310b. However, there can be instances where one of display devices 310a, 310b are out of range or otherwise unavailable for a period of time during a session in which analyte sensor system 308 is measuring, collecting, processing and/or generating data for transmission to one or both of connected display devices 310a, 310b. Such a period of time can be minutes, hours or even days. In such instances, it can be desirable to be able to backfill data, stored by one of the display devices 310a, 310b or by analyte sensor system 308, to the unavailable display device once the unavailable display device becomes available for communication again.

For example, a first display device 310b can be configured to receive and store data related to an analyte concentration monitoring session, for example analyte concentration measurements, indications of food intake, indications of exercise or other user activity while a second display device 310a is out of range or otherwise unavailable to first display device 310b and/or analyte sensor system 308 for a period of time. In some embodiments, analyte sensor system 308 can also or alternatively be configured to store such data during this period of time. First display device 310b and/or analyte sensor system 308 can then be configured to transmit all or a subset of that stored data to second display device 310a responsive to second display device 310a subsequently reentering communication range or otherwise becoming available for communication with first display device 310b and/or analyte sensor system 308. Such transmission/backfilling of data can be communicated utilizing any wireless communication protocol, e.g., Wi-Fi, BLE, Bluetooth, cellular, NFC or any other communication protocol described in this disclosure or otherwise known. In some embodiments, such backfilling of data to display device 310a can be executed responsive to display device 310a transmitting a request for the data ultimately backfilled. In some embodiments, such backfilling of data to display device 310a can be executed responsive to one or both of display device 310b and analyte sensor system 308 detecting or otherwise determining that display device 310a has reentered communication range.

For example, and not limitation, a user may wear display device 310b (e.g., as a smartwatch) and analyte sensor system 308 during a run but the user may not take display device 310a (e.g., as a smartphone) along on the run. During the run and/or during any time interval display device 310a is out of range or otherwise unavailable, display device 310b can receive and store the data related to an analyte concentration monitoring session. In some embodiments, analyte sensor system 308 can also or alternatively be configured to store the data during the time interval. Upon returning from the run and/or upon display device 310a reentering communication range or otherwise becoming available for communication with display device 310b and/or analyte sensor system 308, display device 310b and/or analyte sensor system 308 can be configured to transmit (e.g., backfill) all or a subset of that stored data to display device 310a responsive to display device 310a subsequently reentering communication range or otherwise becoming available for communication with display device 310b and/or analyte sensor system 308. In some embodiments, upon reentering communication range or otherwise becoming available for communication with display device 310b and/or analyte sensor system 308, display device 310a can be configured to transmit a request for all or a subset of that stored data. For example, such a request can include one or more timestamps, or indications of such timestamps, corresponding to one or more data sets of missed data to be backfilled. Display device 310a can also be configured to provide the same receipt, storage and transmission/backfilling of data with respect to display device 310b in a reverse arrangement. Display devices 310a, 310b can be similarly configured to receive or generate, store and transmit/backfill any type of data to analyte sensor system 308 in related arrangements. In some embodiments, each of display devices 310a, 310b and analyte sensor system 308 can be configured to store and subsequently transmit/backfill 3 hours, 6 hours, 12 hours, 24 hours or any other amount of data to one or both of the other devices, and/or to another server (e.g., server system 334 in FIG. 3A).

In some cases, smartwatch manufacturers have considered that, when such smartwatches are not being worn by a user, notifications may automatically revert to the user's connected smartphone. However, the ability to acknowledge notifications, e.g., halt alert sequences without going to the smartphone, can be a desired direct-to-watch experience to provide to the user, where some previous implementations would merely send such alerts and/or sequences from analyte sensor system 308 to the smartphone.

The present disclosure contemplates that analyte sensor system 308 may also communicate such alerts, alarms and/or sequences, e.g., glucose alerts, directly to a smartwatch 310b when a connected smartphone 310a is not present. Some embodiments may utilize built-in notification de-duplication logic to prevent the same alert from being displayed on both smartwatch 310b and connected smartphone 310a. Otherwise, smartwatch 310b and connected smartphone 310a may each generate an instance of the same alert. In some embodiments, an algorithm can be utilized by one or more of analyte sensor system 308 and smartwatch 310b to detect and/or otherwise determine the absence of connected smartphone 310a and responsively carry out a direct-to-watch alerting operation.

In some embodiments, setting up such a direct-to-watch implementation may include a new pairing operation between a new analyte sensor system 308 and one or both of the user's smartwatch 310b and the user's smartphone 310a. In some embodiments, certain control features may be managed and/or controlled by the user via smartphone 310a, for example the ability of a user to input commands to start and/or stop sensor acquisition of analyte data, initial pairing with a new transmitter (e.g., analyte sensor system 308) and changes to alert settings and/or thresholds. In some embodiments, smartwatch 310b can be configured to display a continuous glucose monitored glucose value, an arrow indicating a direction, trend or forecast of a monitored glucose value, and/or a trend graph of the monitored glucose value when smartphone 310a is out of range of one or both of analyte sensor system 308 and smartwatch 310b, thereby providing a classic smartwatch experience, but with data pulled from and/or transmitted directly from analyte sensor system 308 to smartwatch 310b. Such embodiments may provide more reliable electronic glucose value updates on smartwatch 310b for a more up-to-date user experience. In some embodiments, alerts and/or alarms can be displayed by smartwatch 310b and/or acknowledged by the user via input to smartwatch 310b when smartphone 310a is out of range of one or both of smartwatch 310b and analyte sensor system 308. Such alerts and/or alarms may comprise any one or more of visual, auditory and haptic notifications.

In some embodiments, an invitation screen on a continuous glucose monitoring app configured to run on the user's connected smartphone 310a may be configured to inform the user of the availability status of such direct-to-watch features based at least in part on detection of one or both of an analyte sensor system 308 and a smartwatch 310b that are each configured to support such direct-to-watch features. Such an app may also provide one or more setup screens to support the setup of new features on connected smartwatch 310b and/or to support pairing of analyte sensor system 308 with smartwatch 310b, for example, when a new analyte sensor system 308 is first activated. In some embodiments, analyte sensor system 308 can be configured to allow for direct-to-watch operation while also retaining display, alerting and/or alarming function on connected smartphone 310a and/or on another display device.

Figure 24A:
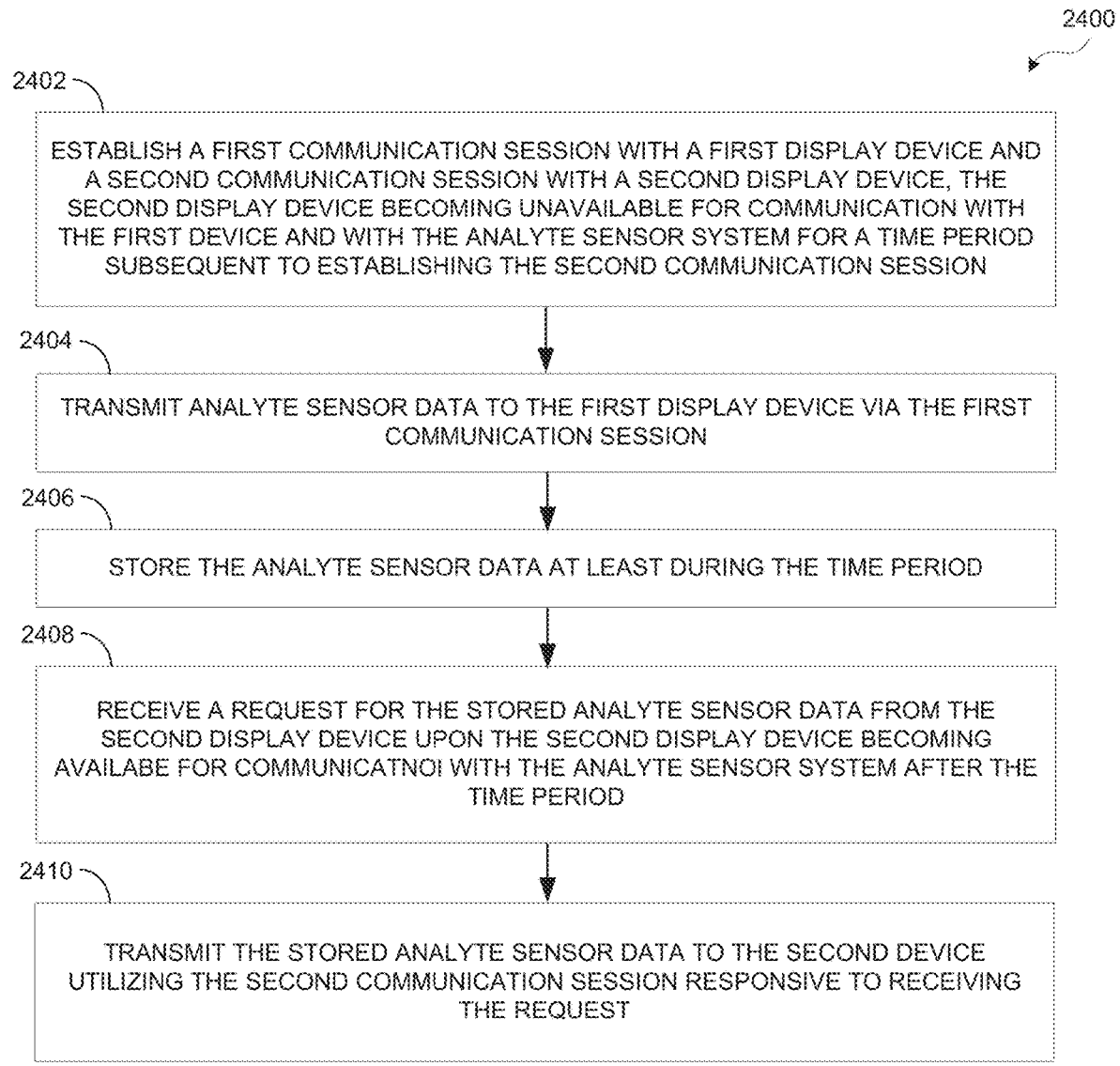
FIG. 24A is an operational flow diagram illustrating various operations that can be performed in accordance with embodiments of the disclosure.

Description now turns to flowchart 2400 of FIG. 24A, describing backfilling by analyte sensor system 308 to a previously but temporarily unavailable display device 310a, according to some embodiments. Block 2402 includes establishing a first communication session with a first display device and a second communication session with a second display device, the second display device becoming unavailable for communication with the first device and with the analyte sensor system for a time period subsequent to establishing the second communication session. For example, analyte sensor system 308 can be configured to establish a first communication session with first display device 310b (e.g., a smart watch) and a second communication session with second display device 310a (e.g., a smart phone), for example as previously described in connection with FIGS. 22A-23. Second display device 310a can become unavailable for communication with first device 310b and with analyte sensor system 308 for a time period subsequent to establishing the second communication session as described above.

Block 2404 includes transmitting analyte sensor data to the first display device via the first communication session. For example, analyte sensor system 308 can be configured to transmit analyte sensor data to first display device 310b (e.g., the smart watch) via the first communication session.

Block 2406 includes storing the analyte sensor data at least during the time period. For example, analyte sensor system 308 can be configured to store the analyte sensor data at least during the time period that second display device 310a (e.g., the smartphone) is unavailable.

Block 2408 includes receiving a request for the stored analyte sensor data from the second display device upon the second display device becoming available for communication with the analyte sensor system after the time period. For example, analyte sensor system 308 can be configured to receive a request for the stored analyte sensor data from second display device 310a upon second display device 310a becoming available for communication with analyte sensor system 308 after the time period.

Block 2410 includes transmitting the stored analyte sensor data to the second device utilizing the second communication session responsive to the request. For example, analyte sensor system 308 can be configured to transmit the stored analyte sensor data to second device 310a (e.g., the smartphone) utilizing the second communication session responsive to receiving the request from second device 310a.

Figure 24B:
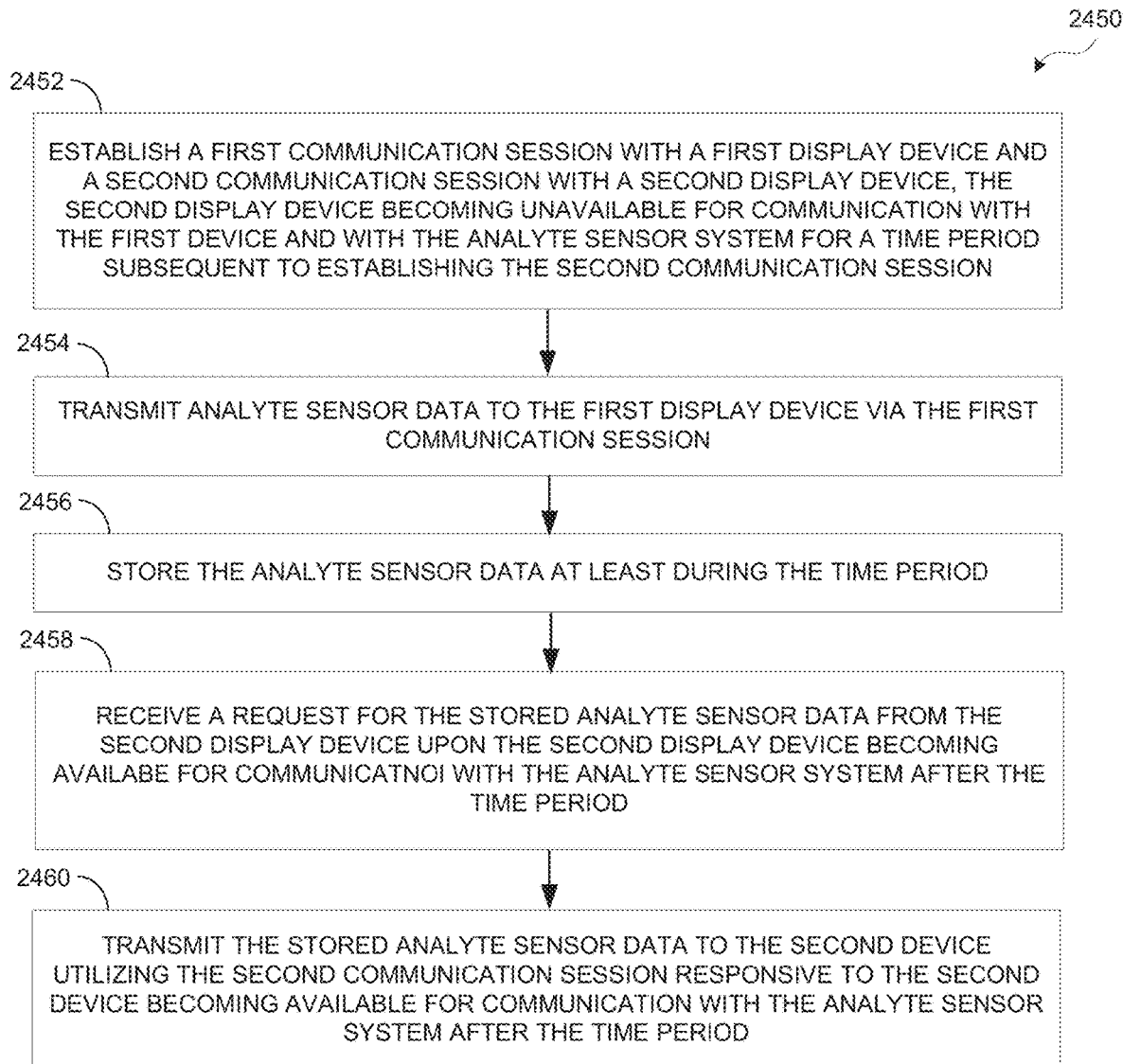
FIG. 24B is an operational flow diagram illustrating various operations that can be performed in accordance with embodiments of the disclosure.

Description now turns to flowchart 2450 of FIG. 24B, describing backfilling by display device 310b to a previously but temporarily unavailable display device 310a, according to some embodiments. Block 2452 includes establishing a first communication session between a first display device and an analyte sensor system and a third communication session between the first display device and a second display device, the second display device having established a second communication session with the analyte sensor. For example, a display device such as display device 310b can be configured to establish a first communication session with analyte sensor system 308 and a third communication session with display device 310a, display device 310a having established a second communication session with analyte sensor 308.

Block 2454 includes receiving analyte sensor data from the analyte sensor system via the first communication session, wherein the second display device becomes unavailable for communication with the first device and with the analyte sensor system for a time period subsequent to establishment of the second communication session. For example, display device 310b can be configured to receive analyte sensor data from analyte sensor system 308 via the first communication session. Display device 310a becomes unavailable for communication with display device 310b and with analyte sensor system 308 for a time period subsequent to establishment of the second communication session.

Block 2456 includes storing the analyte sensor data at least during the time period. For example, display device 310b can be configured to store the analyte sensor data at least during the time period display device 310a is unavailable.

Block 2458 includes receiving a request for the stored analyte sensor data from the second display device upon the second device becoming available for communication over the third communication session after the time period. For example, first display device 310b can be configured to receive a request for the stored analyte sensor data from second display device 310a upon second display device 310a becoming available for communication over the third communication session after the time period.

Block 2460 includes transmitting the stored analyte sensor data to the second device utilizing the third communication session responsive to the request. For example, display device 310b can be configured to transmit the stored analyte sensor data to display device 310a utilizing the third communication session responsive to receiving the request from display device 310a.

Figure 24C:
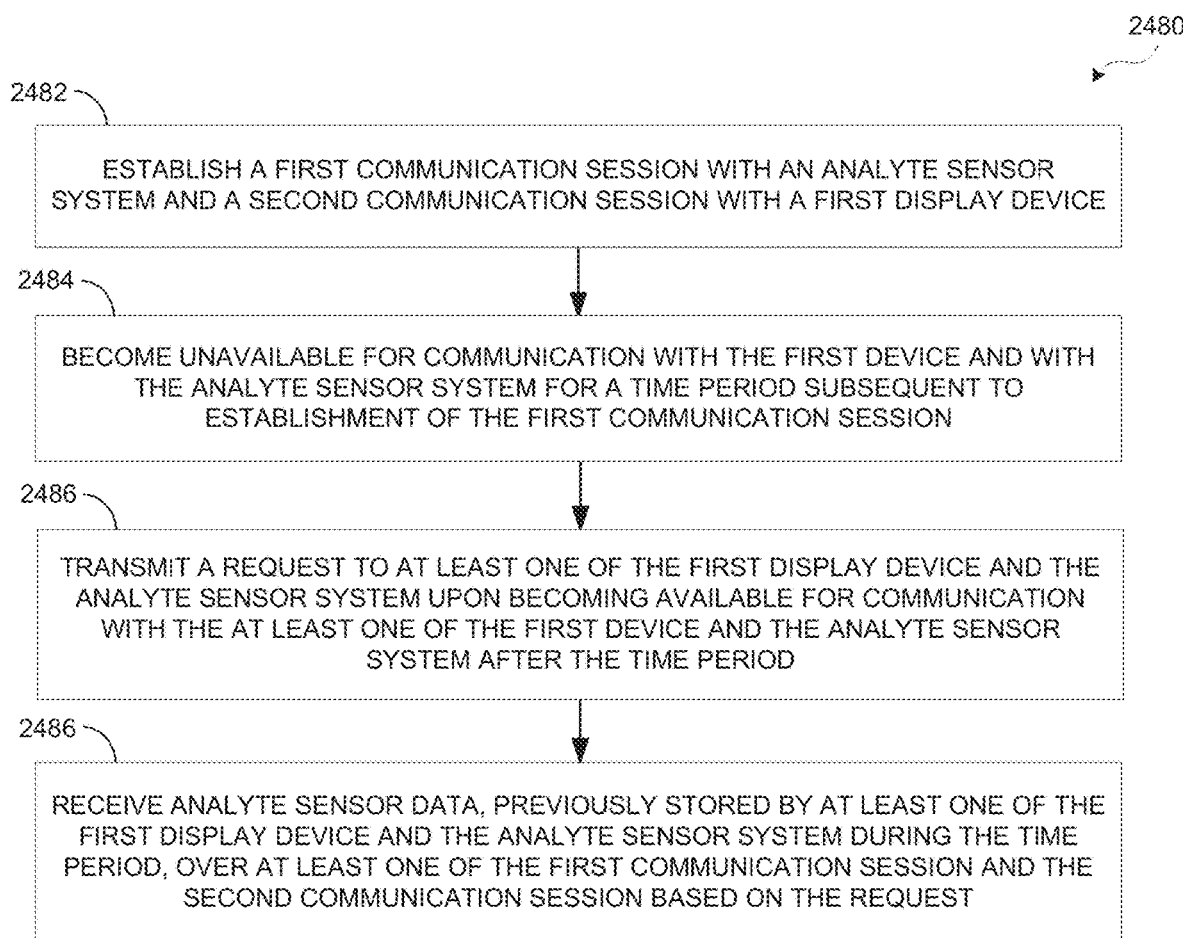
FIG. 24C is an operational flow diagram illustrating various operations that can be performed in accordance with embodiments of the disclosure.

Description now turns to flowchart 2480 of FIG. 24C, describing receiving backfill data by a previously but temporarily unavailable display device 310a, according to some embodiments. Block 2482 includes establishing a first communication session with an analyte sensor system and a second communication session with a first display device. For example, display device 310a can be configured to establish a first communication session with analyte sensor system 308 and a second communication session with display device 310b.

Block 2484 includes becoming unavailable for communication with the first device and with the analyte sensor system for a time period subsequent to establishment of the first communication session. For example, display device 310a can become unavailable for communication with display device 310b and with analyte sensor system 308 for a time period subsequent to establishment of the first communication session.

Block 2486 includes transmitting a request to at least one of the first display device and the analyte sensor system upon becoming available for communication with the at least one of the first device and the analyte sensor system after the time period. For example, display device 310a can be configured to transmit a request to at least one of display device 310b and analyte sensor system 308 upon becoming available for communication with the at least one of first device 310b and analyte sensor system 308 after the time period.

Block 2486 includes receiving analyte sensor data, previously stored by the at least one of the first display device and the analyte sensor system during the time period, over at least one of the first communication session and the second communication session based on the request. For example, display device 310a can be configured to receive analyte sensor data, previously stored by at least one of display device 310b and analyte sensor system 308 during the time period display device 310a was unavailable, over at least one of the first communication session and the second communication session based on the request.

Closing Connections with an Analyte Sensor System

In some circumstances analyte sensor system 308 may wish to close an existing connection with a connected display device 310. Rather than immediately closing the existing connection during a predetermined communication interval, analyte sensor system 308 can be configured to delay closing of the existing connection until after completion of general advertising, e.g., advertising which utilizes the first set of parameters for transmission of advertising messages. This can provide several benefits.

For example, some display devices, e.g., some smartphones, are configured to continuously monitor for general advertising when they are not associated with an established communication session with another device, e.g., with an analyte sensor system. If an established communication session between such a display device and the analyte sensor system is terminated while the analyte sensor system is performing general advertising, the display device may immediately begin monitoring for general advertising and may undesirably reestablish a new communication session with the analyte sensor system in the same predetermined connection interval in which the prior communication session was terminated. By keeping such a communication session open for a period of time after it is identified for closing, e.g., until after general advertising has completed, such undesirable reestablishing of a new communication session in the same predetermined connection interval in which the prior communication session was terminated can be prevented. In some cases, medical display devices can also be configured not to monitor for general advertisements until the next predetermined connection interval.

In some embodiments, analyte sensor system 308 can be configured to close one or more connections, e.g., communication sessions, responsive to a mode of analyte sensor system 308 changing. For example, analyte sensor system 308 can transition from a mode where a glucose monitoring session, e.g., measuring and/or transmitting glucose data, is currently in progress to a mode where the glucose monitoring session is no longer in progress. In some embodiments, this state change can be initiated responsive to user input from one 310a of a plurality of display devices 310a, 310b that are simultaneously connected to analyte sensor system 308. Such a mode or state transition of analyte sensor system 308 can be problematic for a display device, e.g., display device 310b, that expects the mode or state of analyte sensor system 308 to remain unchanged while that display device 310b is connected to analyte sensor system 308. By closing all connections to display devices, e.g., display device 310b, other than the particular display device that caused the state change, e.g., display device 310a, all connected display devices 310a, 310b can have an accurate understanding of the mode or state of analyte sensor system 308 for the duration of their connection.

In some embodiments, rather than closing a connection for which a determination to close has been made or for which a close request has been received, the connection can be kept alive through the transmission of periodic heartbeat signals configured to notify analyte sensor system 308 that a connected display device 310 is still using or still intends to use the connection. In some embodiments, the heartbeat signals can be transmitted periodically by connected display device 310 according to a first interval before a connection close request or close determination, while the heartbeat signal can be adjusted such that it is transmitted by connected display device 310 according to a second interval greater than the first interval after the connection close request. Accordingly, one or both of analyte sensor system 308 and the connected display device 310 can negotiate, calculate or otherwise determine the first interval and/or the second interval.

In some embodiments, analyte sensor system 308 can be configured to close a connection with a particular display device 310 responsive to the connection being determined inactive for a predetermined period of time (e.g., 3 seconds). In such embodiments, one or more of the following conditions can indicate that a connection is active: the display device on the connection is authenticated, the display device on the connection completes a BLE pairing process, the display device on the connection completes a BLE bonding process, analyte sensor system 308 transmits or receives an opcode over the connection, analyte sensor system 308 transmits a data packet over the connection, communication over the connection is blocked by another connected display device executing an opcode (e.g., a connection will not timeout while the display device is waiting for service from analyte sensor system 308), receipt of a heartbeat signal configured to notify analyte sensor system 308 that a connected display device is still using or still intends to use the connection, or any other suitable operation that utilizes the connection.

In some embodiments, one or more connection parameters (e.g., the predetermined timeout period described above, the intervals and/or other characteristics of heartbeat signals, etc.) can be negotiated, determined, adjusted or otherwise established or modified by analyte sensor system 308 and a connected display device 310 based on one or more factors. For example, a first set of connection parameters can be utilized for active connections, a second set of connection parameters can be utilized for connections providing data streaming, and/or a third set of connection parameters can be utilized for connections that have been identified for closure but are being kept alive as described throughout this description.

Figure 25:
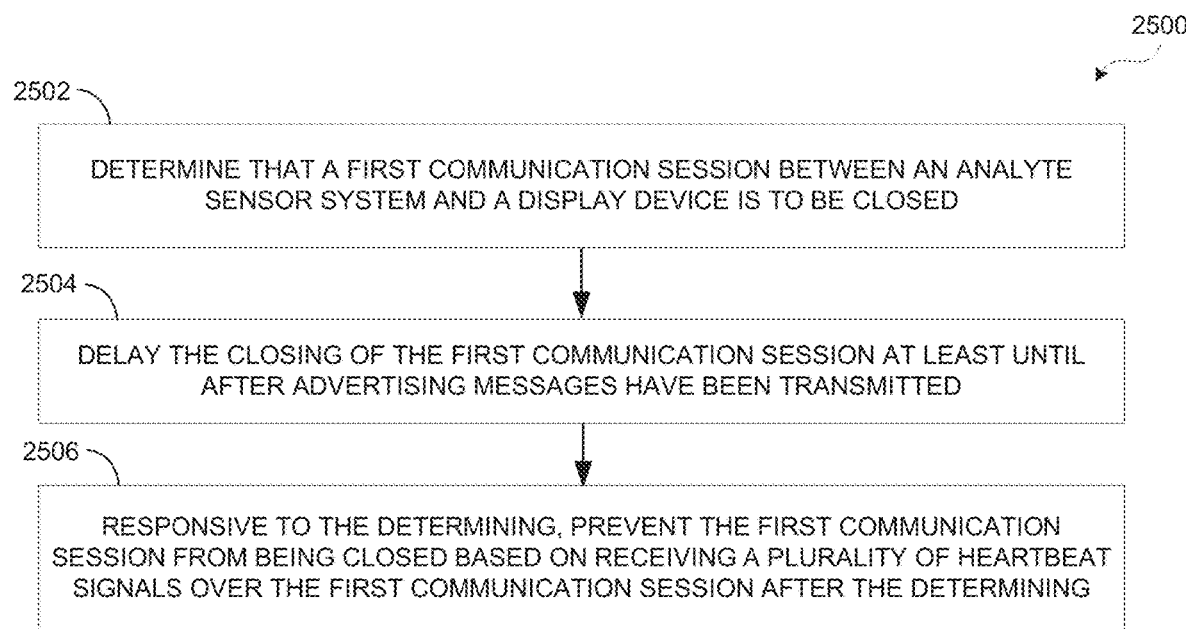
FIG. 25 is an operational flow diagram illustrating various operations that can be performed in accordance with embodiments of the disclosure.

Description now turns to flowchart 2500 of FIG. 25, describing the delay or prevention of the closure of communication connections for which a determination has been made that the communication connections should be closed, according to some embodiments. Block 2502 includes determining that a first communication session between an analyte sensor system and a display device is to be closed. For example, analyte sensor system 308 can be configured to determine that a first communication session with a display device, e.g., one or both of display device 310a, 310b, is to be closed.

Block 2504 includes delaying the closing of the first communication session at least until after advertising messages have been transmitted. For example, analyte sensor system 308 can be configured to delay the closing of the first communication session at least until after advertising messages 2202 (see FIG. 22A, B) have been transmitted.

In some embodiments, an additional block 2506 can include, responsive to the determining, preventing the first communication session from being closed based on receiving a plurality of heartbeat signals over the first communication session after the determining. For example, in some embodiments, analyte sensor system 308 can be further or alternatively configured to, responsive to determining that the first communication session is to be closed, prevent the first communication session from being closed based on receiving a plurality of heartbeat signals from the display device, e.g., one or both of display device 310a, 310b, over the first communication session after the determination has been made. In some such embodiments, display devices 310a, 310b can prevent their communication sessions from being closed, despite analyte sensor system 308 having previously determined the communication sessions should be closed, at least during general advertising of a particular predetermined connection interval, by sending such heartbeat signals.

Data Logging
Health Care Provider Devices

In some embodiments, it may be desirable for a health care provider, for example a user's doctor, to be able to access analyte concentration data of the user to aid in medical treatment. Accordingly, several embodiments that may utilize heath care provider device 150, as briefly introduced in connection with FIG. 1A, are described below.

Figure 26:
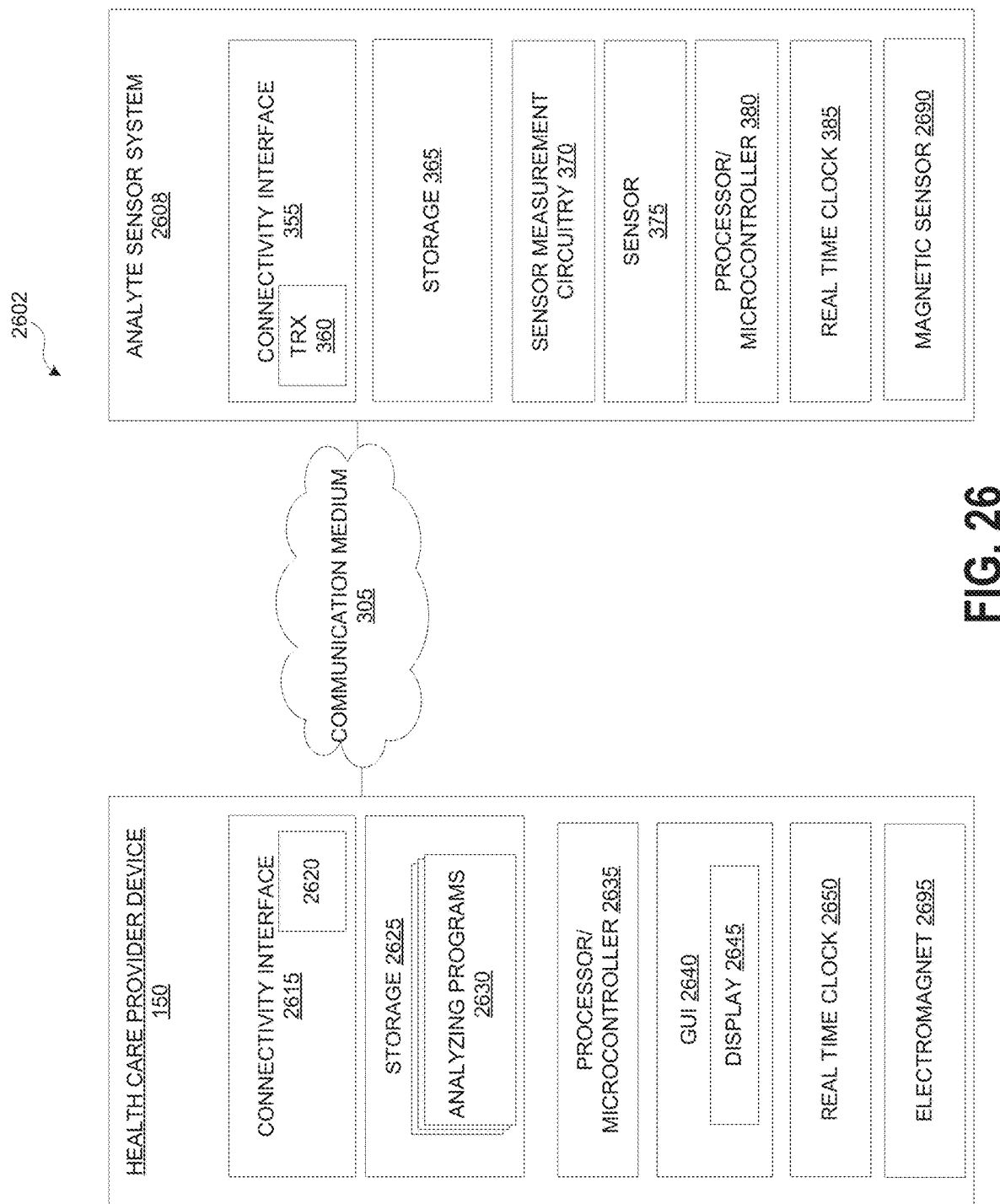
FIG. 26 illustrates aspects of an example system that can be used in connection with implementing embodiments of the disclosure.

FIG. 26 depicts system 2602, which includes examples of additional aspects of the present disclosure that can be used in connection with any analyte sensor system described herein. As illustrated in FIG. 26, system 2602 can include health care provider (HCP) device 150, which is configured to be utilized by health care providers to download, track, log, and/or otherwise analyze data provided by one or more analyte sensor systems, for example analyte sensor system 2608. Although several features of HCP device 150 are described below, the present disclosure contemplates that HCP device 150 can comprise additional, fewer or alternative elements, features and/or functionality to those specifically described.

As shown, HCP device 150 can include a processor/microprocessor 2635 for processing, analyzing and/or managing sensor data ultimately received from analyte sensor system 2608. HCP device 150 can include display 2645, storage 2625, analyzing programs 2630, and real time clock 2650 for displaying, storing, and analyzing sensor data. HCP device 150 can further include a radio unit or transceiver 2620 coupled to other elements of HCP device 150 via connectivity interface 2615 and/or a bus. Transceiver 2620 can employ a communication protocol for receiving sensor data from and sending requests, instructions, and/or data to analyte sensor system 2608. Storage 2625 can also be used for storing an operating system for HCP device 150 and/or a custom (e.g., proprietary) application designed for analyzing sensor data ultimately downloaded and/or received from analyte sensor system 2608. Storage 2625 can be a single memory device or multiple memory devices and can be a volatile or non-volatile memory for storing data and/or instructions for software programs and applications. The instructions can be executed by processor 2635 to control and manage the operations of one or more components of HCP device 150.

Connectivity interface 2615 interfaces HCP device 150 to communication medium 305, such that HCP device 150 can be communicatively coupled to analyte sensor system 2608 via communication medium 305. Transceiver 2620 of connectivity interface 2615 can include multiple transceiver modules operable on different wireless standards. Transceiver 2620 can be used to receive analyte data and, in some embodiments, associated commands and messages from analyte sensor system 2608. Additionally, connectivity interface 2615 can in some cases include additional components for controlling radio and/or wired connections, such as baseband and/or Ethernet modems, audio/video codecs, and so on.

Storage 2625 can include volatile memory (e.g. RAM) and/or non-volatile memory (e.g. flash storage), can include any of EPROM, EEPROM, cache, or can include some combination/variation thereof. In various embodiments, storage 2625 can store user input data and/or other data collected by HCP device 150. Storage 2625 can also be used to store volumes of analyte data received from analyte sensor system 2608 for analyzation. Additionally, storage 2625 can store analyzing programs 2630 that, when executed using processor 2635, for example, analyze sensor data ultimately received from analyte sensor system 2608 and can be configured to generate one or more patient reports corresponding to an analysis of the sensor data.

In various embodiments, a user can interact with analyzing programs 2630 via GUI 2640, which can be provided by display 2645 of HCP device 150.

In various embodiments, HCP device 150 can further comprise an electromagnet 2695 configured to generate a unique electromagnetic sequence and/or signal configured to wake one or more portions of an analyte sensor system 2608 from a low-power, sleep, or shelf mode in preparation for transmission of logged data from analyte sensor system to HCP device 150, for example after a data logging session for analyte sensor system 2608 is complete. A bus (not shown here) can be used to interconnect the various elements of health care provider device 150 and transfer data between these elements.

As illustrated in FIG. 26, system 2602 can further include analyte sensor system 2608 communicatively couplable to HCP device 150 via communication medium 305. As shown, analyte sensor system 2608 can include substantially the same elements, having substantially the same functionality, as analyte sensor system 308 as previously described in connection with FIG. 3B, however, further including a magnetic sensor 2690 configured to generate a signal configured to wake one or more components of analyte sensor system 2608 (e.g., FIG. 4) responsive to receiving a predetermined signal from electromagnet 2695 of HCP device 150 in preparation for transmission of logged data from analyte sensor system to HCP device 150.

Several example operations of HCP device 150 and analyte sensor system 2608 will be now be described below. In some embodiments, a patient can wear analyte sensor system 2608, which can measure analyte concentrations of the patient (e.g., utilizing sensor 375 and sensor measurement circuitry 370) and log those analyte concentrations (e.g., utilizing storage 365). In some embodiments, analyte sensor system 2608 may not immediately transmit logged analyte concentrations to a display device or to HCP device 150. Accordingly, in such embodiments, the patient may not be immediately notified of the analyte concentrations. Rather, analyte sensor system 2608 can be configured to log analyte concentrations for an entire session (e.g., 1 day, 10 days, etc.) and, after the data-collecting session has ended, analyte sensor system 2608 can be configured to revert to a low-power, sleep or shelf mode until awakened by HCP device 150 for transferring the logged analyte concentrations and/or other data to HCP device 150 and/or to another server (e.g., server system 334 of FIG. 3A) for subsequent analyzation.

After the data-collecting session has ended, analyte sensor system 2608 can be mailed or otherwise physically delivered to the health care provider (e.g., a doctor or pharmacist), where the logged data can be downloaded, analyzed and one or more reports of the analysis can be generated by HCP device 150.

In some embodiments, the health care provider can be providing care to more than one patient and, therefore, multiple analyte sensor systems, such as system 2608, can be deployed to multiple patients at a given time. Accordingly, HCP device 150 can have access to a range of transmitter identifications (IDs) corresponding to all or a subset of the analyte sensor systems currently deployed.

Upon receipt by the health care provider, analyte sensor system 2608 can be woken from its low-power, sleep or shelf mode by HCP device 150. HCP device 150 can be configured to generate a signal having a unique sequence configured to wake one or more portions of an analyte sensor system 2608 from the low-power, sleep, or shelf mode. For example, HCP device 150 can be configured to cause electromagnet 2695 to generate such an electromagnetic wake signal. Alternatively, HCP device 150 can be configured to cause transceiver 2620 to transmit such a wake signal.

Responsive to receiving the wake signal, analyte sensor system 2608 can be configured to wake from the low-power, sleep or shelf mode. For example, magnetic sensor 2690 can be configured to generate a wake signal configured to wake one or more components of analyte sensor system 2608 (see, e.g., FIG. 4). Alternatively, transceiver 360, connectivity interface 355 or processor/microcontroller 380 can be configured to generate the wake signal.

Upon waking, analyte sensor system 2608 can be configured to transmit an indication of its corresponding transmitter ID to HCP device 150 in one or more beacon or other messages. In some embodiments, analyte sensor system 2608 can be configured to only pair and communicate with HCP device 150 after the data logging session has ended. Accordingly, responsive to receiving the transmitter ID, HCP device 150 can compare the received transmitter ID to the range of transmitter IDs corresponding to the analyte sensor systems currently deployed. Based on a determination that the received transmitter ID is within the range of transmitter IDs currently deployed, HCP device 150 and analyte sensor system 2608 can pair with one another and establish a wireless connection according to any pairing protocol described herein or any other suitable pairing protocol. HCP device 150 can then download the logged analyte concentration data and/or other data from analyte sensor system 2608. The logged analyte concentration data and/or other data can be stored locally in storage 2625 and/or can be stored remotely in another server, for example, server system 334 of FIG. 3A. The logged analyte concentration data and/or other data can then be analyzed, and one or more patient reports can be generated based thereon.

In some embodiments, the above session logging, end-of-session downloading and subsequent analyzation of downloaded data for report generation can be repeated or concurrently carried out for a plurality of analyte sensor systems, for example in a bulk upload operation.

Figure 27A:
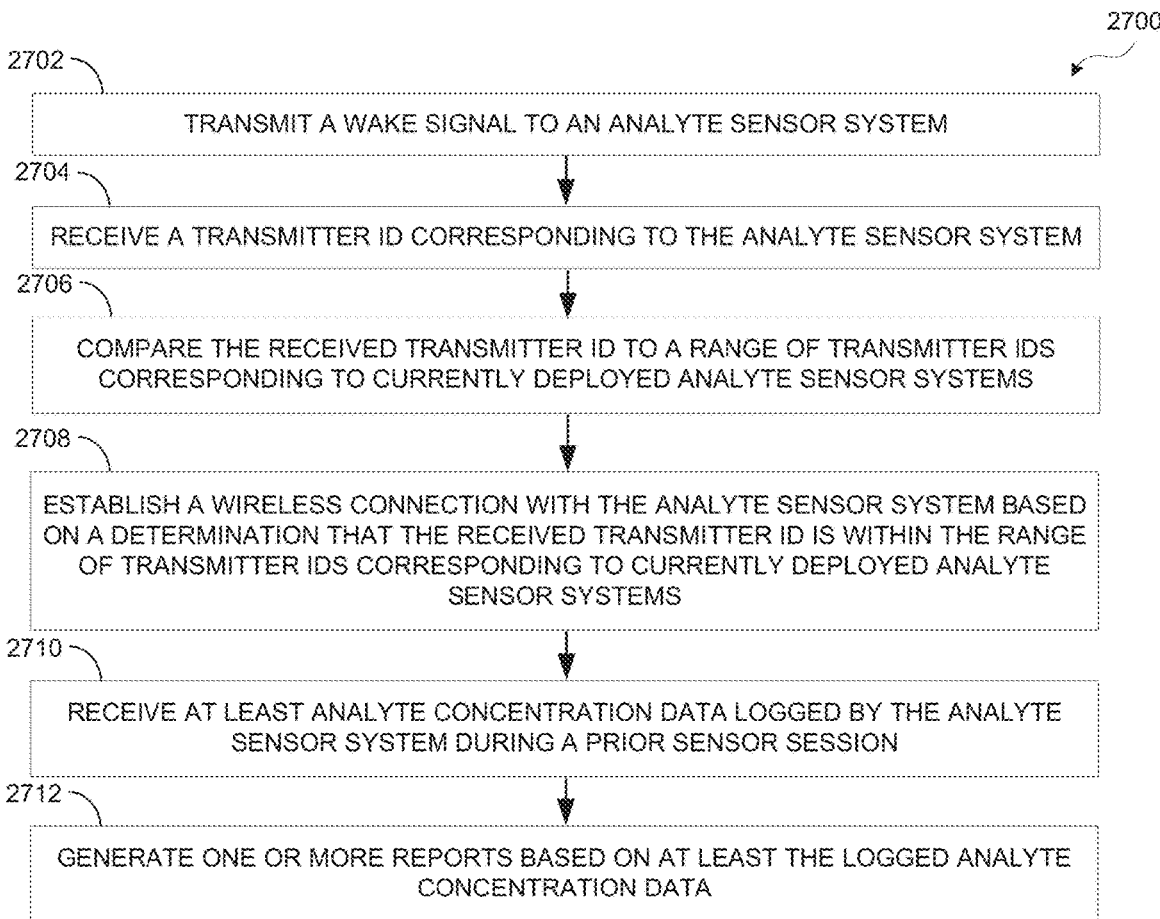
FIG. 27A is an operational flow diagram illustrating various operations that can be performed in accordance with embodiments of the disclosure.

Description now turns to flowchart 2700 of FIG. 27A, describing operations of, for example, HCP device 150, as previously described in connection with FIG. 26. Block 2702 includes transmitting a wake signal to an analyte sensor system. For example, HCP device 150 can utilize electromagnet 2695 and/or transceiver 2620 to generate a unique electromagnetic sequence and/or signal configured to wake one or more portions of an analyte sensor system 2608 from a low-power, sleep, or shelf mode.

Block 2704 includes receiving a transmitter ID corresponding to the analyte sensor system. For example, HCP device 150 can receive an indication of the transmitter ID corresponding to analyte sensor system 2608 from analyte sensor system 2608 in one or more beacon messages or other messages.

Block 2706 includes comparing the received transmitter ID to a range of transmitter IDs corresponding to analyte sensor systems currently deployed. For example, HCP device 150 may have prior knowledge of the range of transmitter IDs corresponding to analyte sensor systems currently deployed and can be configured to compare the received transmitter ID from analyte sensor system 2608 to that range to determine whether analyte sensor system 2608 is one of those deployed systems.

Block 2708 includes establishing a wireless connection with the analyte sensor system based on a determination that the received transmitter ID is within the range of transmitter IDs corresponding to currently deployed analyte sensor systems. For example, HCP device 150 and analyte sensor system 2608 can pair with one another and establish a wireless connection according to any pairing protocol described herein or any other suitable pairing protocol.

Block 2710 includes receiving at least analyte concentration data logged by the analyte sensor system during a prior sensor session. For example, HCP device 150 can download the logged analyte concentration data and/or other data from analyte sensor system 2608.

Block 2712 includes generating one or more reports based on at least the logged analyte concentration data. For example, HCP device 150 can analyze the logged analyte concentration data and/or other data, and one or more patient reports can be generated based thereon.

Figure 27B:
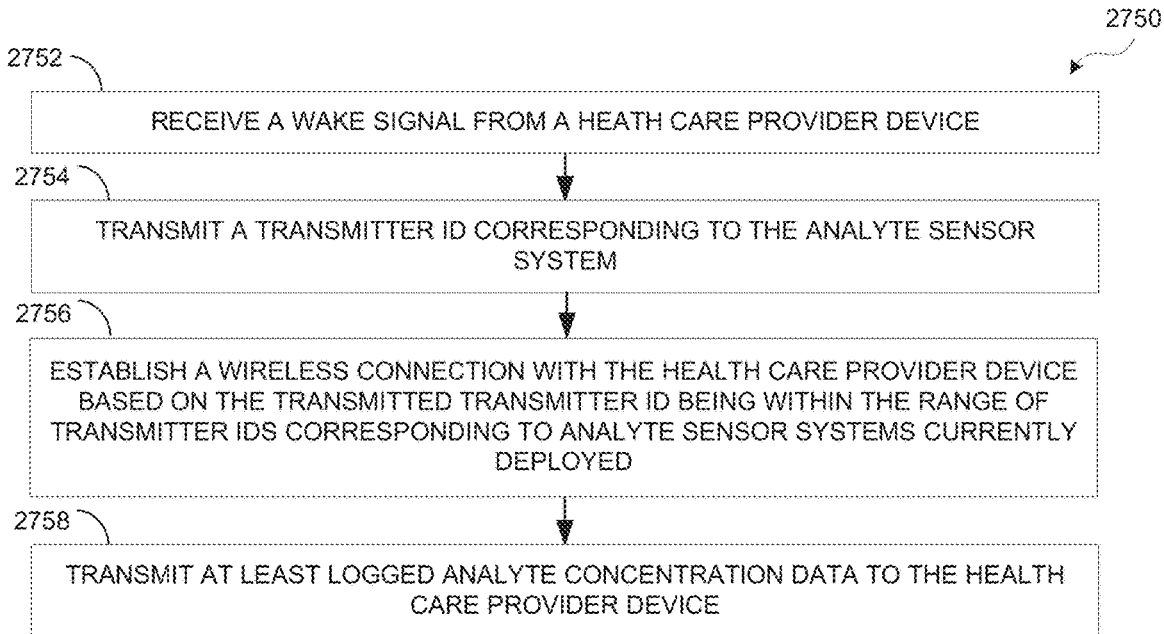
FIG. 27B is an operational flow diagram illustrating various operations that can be performed in accordance with embodiments of the disclosure.

Description now turns to flowchart 2750 of FIG. 27B, describing operations of, for example, analyte sensor system 2608, as previously described in connection with FIG. 26. Block 2752 includes receiving a wake signal from a heath care provider device. For example, analyte sensor system 2608 can receive a unique electromagnetic sequence and/or signal configured to wake one or more portions of an analyte sensor system 2608 from a low-power, sleep, or shelf mode. The sequence or signal can be generated by electromagnet 2695 and/or transceiver 2620 of HCP device 150 and received by magnetic sensor 2690 and/or transceiver 360, respectively.

Block 2754 includes transmitting a transmitter ID corresponding to the analyte sensor system. For example, analyte sensor system 2608 can transmit an indication of the transmitter ID corresponding to analyte sensor system 2608 in one or more beacon messages or other messages.

Block 2756 includes establishing a wireless connection with the health care provider device based on the transmitted transmitter ID being within the range of transmitter IDs corresponding to currently deployed analyte sensor systems. For example, HCP device 150 and analyte sensor system 2608 can pair with one another and establish a wireless connection according to any pairing protocol described herein or any other suitable pairing protocol.

Block 2758 includes transmitting at least logged analyte concentration data to the health care provider device. For example, HCP device 150 can download the logged analyte concentration data and/or other data from analyte sensor system 2608. One or more reports can be generated based on at least the logged analyte concentration data from the analyte sensor system.

Delaying Processing of Logged Analyte Data Until After a Session is Complete

In some embodiments, it may be desirable to sample analyte concentrations (e.g., blood glucose concentrations) periodically, log the raw data, and delay processing and/or conversion of the raw data until a sensor session has concluded (e.g., after a 1- or 10-day sensor session, which can correspond to an intended usable life of the analyte sensor system). Post-processing and/or other conversion of the raw data to estimated glucose values can then be carried out after the sensor session has concluded to, for example, determine the nature of the diabetes of the patient (e.g., Type 1, Type 2). By delaying the conversion of the raw data to estimated glucose values, computational and operational burden on the analyte sensor system (e.g., any analyte sensor system described herein) can be greatly reduced, since alarms and/or alerts would not be generated in real-time or near real-time (i.e., when the user is using the analyte sensor system). In such embodiments, the analyte sensor system would essentially function as a data logger during the sensor session.

Figure 28:
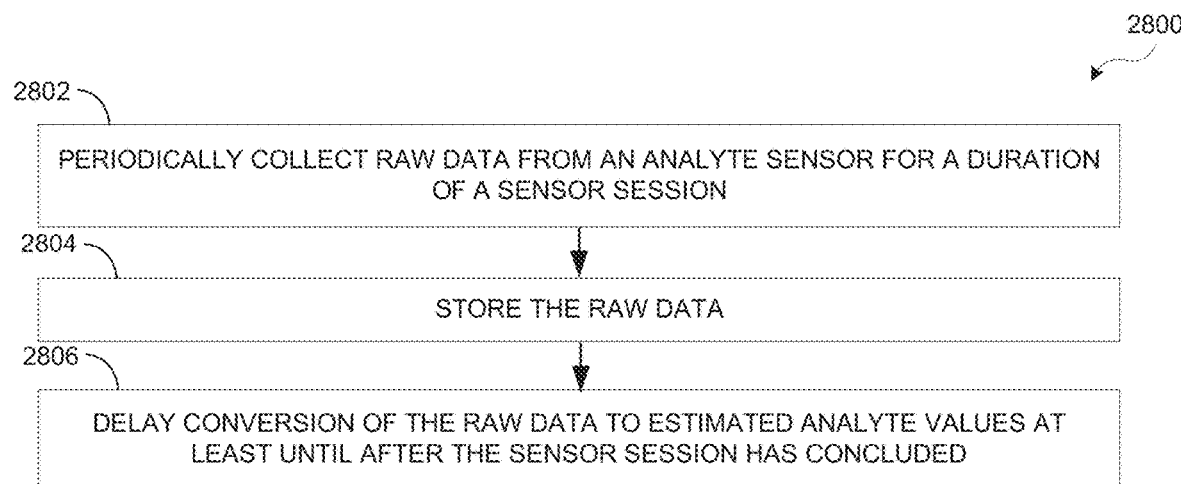
FIG. 28 is an operational flow diagram illustrating various operations that can be performed in accordance with embodiments of the disclosure.

Flowchart 2800 of FIG. 28 describes example operations of an analyte sensor system, for example analyte sensor system 308 or any other analyte sensor system described herein, according to such data logging and conversion/processing delaying embodiments. Block 2802 includes periodically collecting raw data from an analyte sensor for a duration of a sensor session. For example, analyte sensor system 308 can sample blood glucose every 30 seconds, every 1 minute or according to any other suitable periodic or aperiodic interval and generate raw analyte data for the duration of a sensor session (e.g., a 1- or 10-day sensor session, which can correspond to an intended user interval of the analyte sensor system). In some embodiments, the raw analyte data can comprise numerical indications of a voltage or current generated by an analyte sensor, for example, sensor 375, as determined by, for example, sensor measurement circuitry 370.

Block 2804 includes storing the raw data. For example, analyte sensor system 308 can be configured to log the raw data generated by sensor measurement circuitry 370, for example, in storage 365.

Block 2806 includes delaying conversion of the raw data to estimated analyte values until at least after the sensor session has concluded. For example, analyte sensor system 308 can be configured to not convert or otherwise process the raw data stored in storage 365 during the sensor session. In some embodiments, analyte sensor system 308 can be configured to convert and/or process the raw data after the sensor session has concluded. Alternatively or additionally, analyte sensor system 308 can be configured to transmit the raw data and/or a processed version of the raw data, processed by analyte sensor system 308 after conclusion of the sensor session, to another device, e.g., HCP device 150 (FIG. 26), server system 334 (FIG. 3A), or any other display device described herein, during or after the sensor session, for processing, analyzing and/or displaying after the sensor session has concluded.

Logging and Transfer of Analyte Data Without a Display Device

In some embodiments, a user of an analyte sensor system, e.g., analyte sensor system 308, may not have a smartphone, smartwatch or other peripheral display device but can still want to be able to send their analyte concentration data to their health care provider. Accordingly, some embodiments of analyte sensor systems, as described herein, can be further configured to communicate utilizing one or more cellular communication protocols, which can allow such analyte sensor systems to push data to a cloud, server or directly to a health care provider device, e.g., server system 334 and/or HCP device 150, without requiring any prior user pairing operation with the cloud, server, or HCP device and, in some cases, without necessarily providing visual indication or display of the analyte concentration data to the patient or user of the analyte sensor system. For example, transceiver 360 of any analyte sensor system described herein can comprise a cellular network-enabled radio chip and/or transmitter. In some embodiments, the analyte sensor system can additionally or alternatively be configured to communicate the analyte concentration data to the cloud, server or health care provider device through a mesh network where enough intervening devices between the analyte sensor system and the cloud, server or HCP device are available and appropriately configured.

Figure 29:
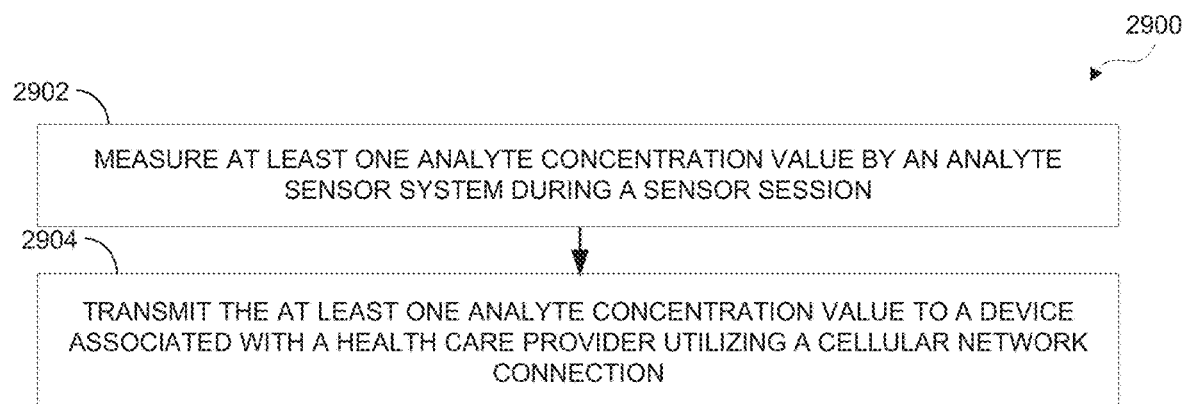
FIG. 29 is an operational flow diagram illustrating various operations that can be performed in accordance with embodiments of the disclosure.

Flowchart 2900 of FIG. 29 describes example operations of an analyte sensor system, for example analyte sensor system 308 or any other analyte sensor system described herein, according to such cellular network-enabled embodiments. Block 2902 includes measuring at least one analyte concentration value by an analyte sensor system during a sensor session. For example, sensor 375 and/or sensor measurement circuitry 370 of analyte sensor system 308 (or any other analyte sensor system described herein) can be configured to measure at least one analyte concentration value (e.g., blood glucose) during a sensor session.

Block 2904 includes transmitting the at least one analyte concentration value to a device associated with a health care provider utilizing a cellular network connection. For example, transceiver 360 of analyte sensor system 308 (or any other analyte sensor system described herein) can comprise a cellular network-enabled radio chip configured to push data to a cloud, server or directly to a health care provider device, e.g., server system 334 and/or HCP device 150. Such data transmission can occur without necessarily providing visual indication or display of the analyte concentration data to the patient or user of analyte sensor system 308.

Facilitating Troubleshooting of Customer Complaints

Use of analyte sensor systems, as those disclosed herein, can sometimes require technical trouble shooting. In some instances, a user can contact customer support with a complaint relating to the analyte sensor system, for example, repeated connection losses, inability to connect, etc. While such complaints can be a result of a dead battery within the analyte sensor system, customer support representatives can have limited, if any, real-time information about the analyte sensor system that can be used to determine what, if any, issues actually exist.

Accordingly, the present disclosure contemplates embodiments in which analyte sensor systems can be configured with NFC circuitry that allows an NFC communication from a separate display device to temporarily provide power to portions of the analyte sensor system necessary for triggering and executing a download of data stored on the analyte sensor system, via another communication protocol, for example BLE, to the display device for subsequent retransmission to another server or device accessible to the customer service representative for troubleshooting the customer complaint.

For example, as previously described, display device 310 (FIG. 3B) can include transceiver 320 comprising an NFC controller, as well as circuitry configured for communicating according to at least two other communication protocols (e.g., BLE and Wi-Fi). Display device 310 can also comprise storage 325 having stored thereon analyte sensor application 330, which in some cases can further include programming, code or instructions sufficient to direct a user, with or without the assistance of a customer service representative, to perform the troubleshooting process described according to these embodiments.

Analyte sensor system 308 (FIG. 3B) can include transceiver 360 comprising an NFC antenna and associated circuitry configured to receive power, via NFC, from the NFC controller of transceiver 320 within display device 310 when display device 310 is so instructed and brought sufficiently close to analyte sensor system 308. Transceiver 360 can be configured to direct and/or otherwise use this received power to power itself and any other elements within analyte sensor system 308 necessary to communicate data stored in storage 365 to display device 310, for example processor/microcontroller 380, real time clock 385 and/or storage 365.

Upon receiving the power via NFC and powering up the necessary elements, analyte sensor system 308 can be configured to cause transceiver 360 to transmit data stored in storage 365 and/or data generated according to one or more operations of the troubleshooting procedure to display device 310 utilizing a first communication protocol (e.g., BLE). Upon receipt of the data from analyte sensor system 308, via the first communication protocol, display device 310 can be configured to retransmit the data, utilizing a second communication protocol (e.g., Wi-Fi) to another server or device accessible to the customer service representative, e.g., server system 334 (FIG. 3A). In such embodiments, the analyte sensor application 330 can be preloaded with an address or URL of the server or device to which the data is to be transmitted.

Once the customer service representative has access to the data, the customer service representative can utilize the data to determine or facilitate a determination of an appropriate diagnosis, e.g., the transmitter is bad, return to the manufacturer; there is a sensor issue, ask the user to try another sensor; the transmitter is out of useful life, the warranty has expired and the transmitter worked appropriately for the expected duration; or some other diagnosable condition.

In some embodiments, where this procedure is used in-factory for already-returned analyte sensor systems, the process can be shortened by applying NFC power to analyte sensor system 308, utilizing a factory diagnostic tool having similar relevant functionality to display device 310, and transferring the data from analyte sensor system 308 to the diagnostic tool via the first communication protocol (e.g., BLE). Such a method could similarly be utilized for powering up malfunctioning or inoperable receivers or other dedicated display devices and initiating a similar data transmission from the receiver or other dedicated display device.

Figure 30A:
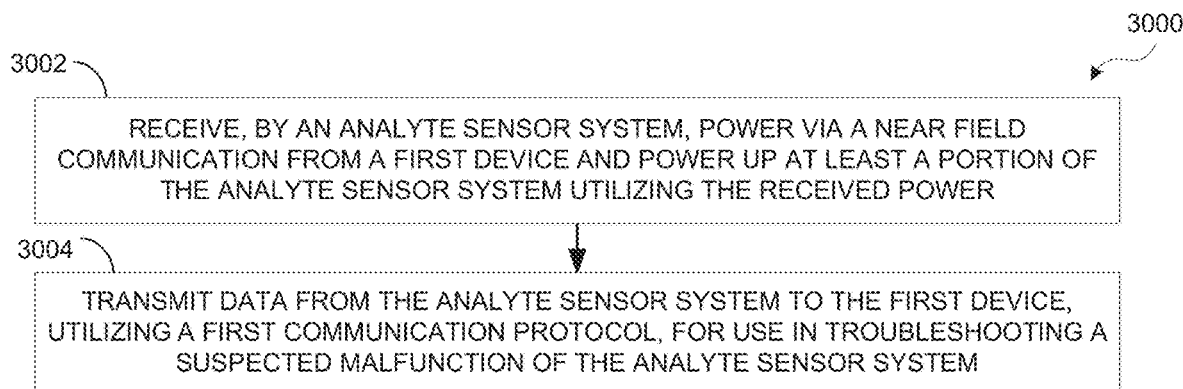
FIG. 30A is an operational flow diagram illustrating various operations that can be performed in accordance with embodiments of the disclosure.

Description now turns to flowchart 3000 of FIG. 30A, describing operations of, for example, analyte sensor system 308, as described above. Block 3002 includes receiving, by an analyte sensor system, power via a near field communication from a first device and powering up at least a portion of an analyte sensor system utilizing the received power. For example, analyte sensor system 308 can be configured to receive power via NFC, from display device 310, and to power up at least some of its elements for subsequent transmission of data.

Block 3004 includes transmitting data from the analyte sensor system to the first device, utilizing a first communication protocol, for use in troubleshooting a suspected malfunction of the analyte sensor system. For example, analyte sensor system 308 can be configured to cause transceiver 360 to transmit data stored in storage 365 and/or data generated according to one or more operations of the troubleshooting procedure to display device 310 utilizing a first communication protocol (e.g., BLE).

Figure 30B:
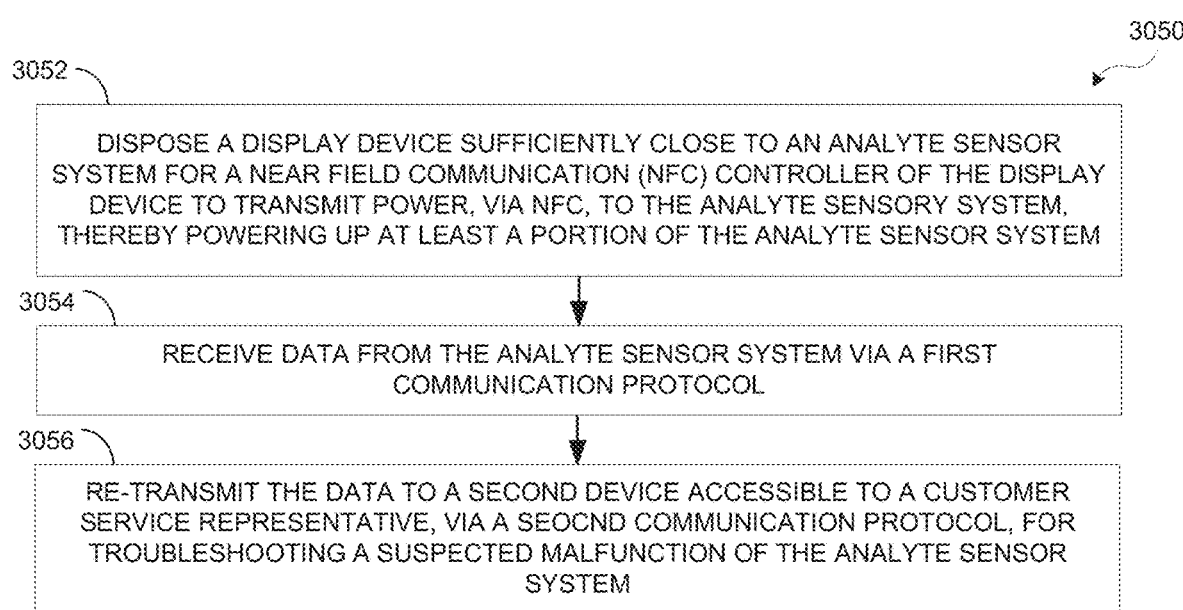
FIG. 30B is an operational flow diagram illustrating various operations that can be performed in accordance with embodiments of the disclosure.

Description now turns to flowchart 3050 of FIG. 30B, describing operations of, for example, display device 310, as described above. Block 3052 includes disposing a display device sufficiently close to an analyte sensor system for a short-term wireless communication protocol controller of the display device to transmit power, utilizing the short-term wireless communication protocol, to the analyte sensory system, thereby powering up at least a portion of the analyte sensor system. For example, display device 310 can be disposed sufficiently close to analyte sensor system 308 for a near field communication (NFC) controller of transceiver 320 of display device 310 to transmit power, via NFC, to analyte sensory system 308, thereby powering up at least a portion of analyte sensor system 308.

Block 3054 includes receiving data from the analyte sensor system via a first communication protocol. For example, upon transmitting the power, via NFC, display device 310 can receive data from analyte sensor system 308 utilizing a first communication protocol (e.g., BLE).

Block 3056 includes re-transmitting the data to a second device accessible to a customer service representative, via a second communication protocol, for troubleshooting a suspected malfunction of the analyte sensor system. For example, upon receipt of the data from analyte sensor system 308, via the first communication protocol, display device 310 can be configured to retransmit the data, utilizing a second communication protocol (e.g., Wi-Fi) to another server or device accessible to the customer service representative, e.g., server system 334 (FIG. 3A).

Additional Embodiments

One of skill in the art will appreciate upon studying the present disclosure that various additional embodiments not described explicitly herein are within the spirit and scope of the present disclosure.

Figure 31:
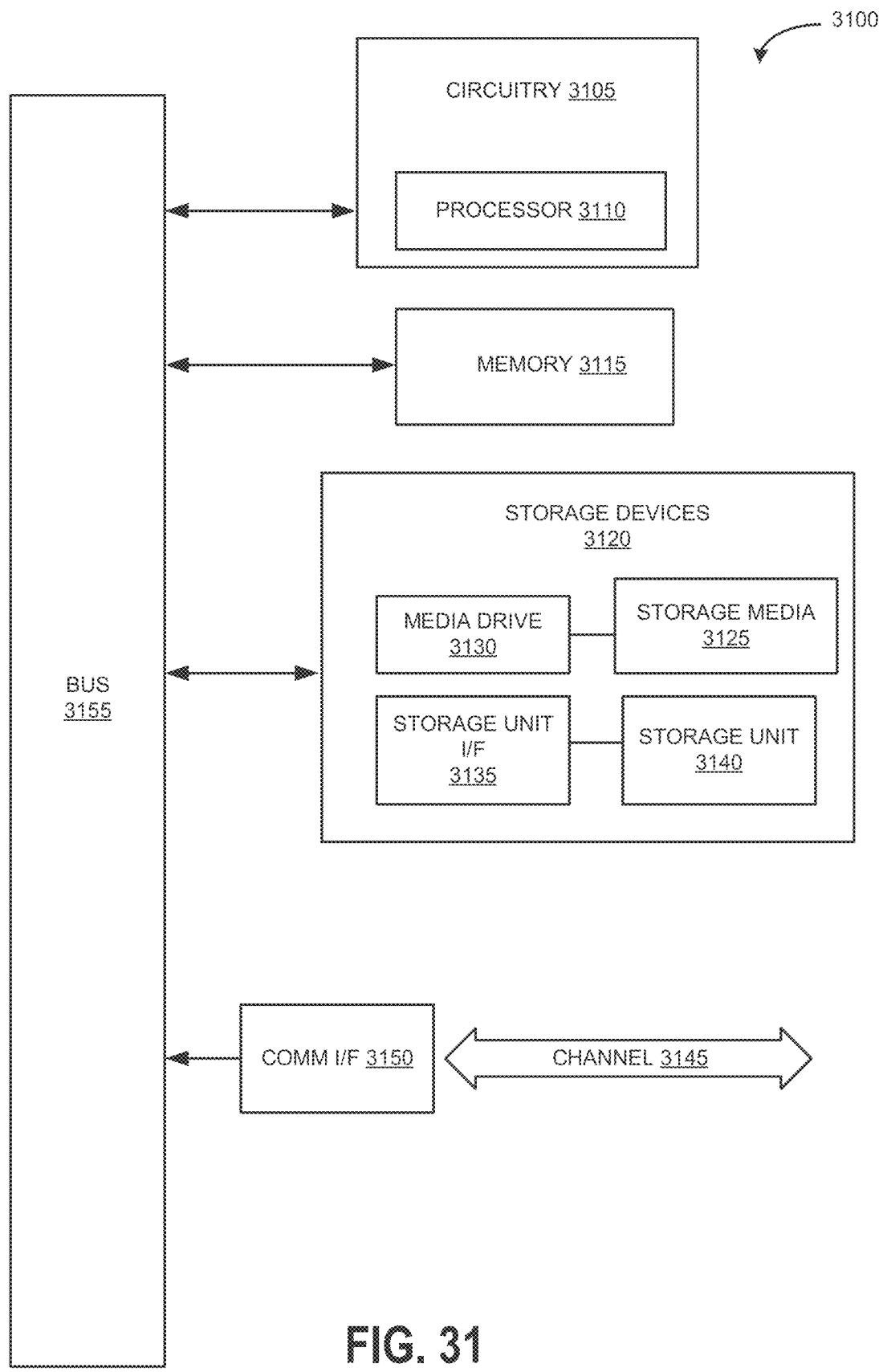
FIG. 31 illustrates an example computing module in accordance with embodiments of the present disclosure.

FIG. 31 illustrates example computing module 3100, which can in some instances include a processor/microprocessor/controller resident on a computer system (e.g., in connection with server system 334, any of the display devices described herein (e.g., display devices 120, 130, 140, 310(*a, b*), as well as analyte display device 110, medical device 136, HCP device 150), and/or analyte sensor system 8, 308, etc.) Computing module 3100 can be used to implement various features and/or functionality of embodiments of the systems, devices, apparatuses, and methods disclosed herein. With regard to the above-described embodiments set forth herein in the context of systems, devices, apparatuses, and methods described with reference to the various FIGS. of the present disclosure, one of skill in the art will appreciate additional variations and details regarding the functionality of these embodiments that can be carried out by computing module 3100. In this connection, it will also be appreciated by one of skill in the art that features and aspects of the various embodiments (e.g., systems, devices, and/or apparatuses, and the like) described herein can be implemented with respected to other embodiments (e.g., methods, processes, and/or operations, and the like) described herein without departing from the spirit of the disclosure.

As used herein, the term module can describe a given unit of functionality that can be performed in accordance with one or more embodiments of the present application. As used herein, a module can be implemented utilizing any form of hardware, software, or a combination thereof. For example, one or more processors, controllers, ASICs, PLAs, PALs, CPLDs, FPGAs, logical components, software routines or other mechanisms can be implemented to make up a module. In implementation, the various modules described herein can be implemented as discrete modules or the functions and features described can be shared in part or in total among one or more modules. In other words, as would be apparent to one of ordinary skill in the art after reading this description, the various features and functionality described herein can be implemented in any given application and can be implemented in one or more separate or shared modules in various combinations and permutations. Even though various features or elements of functionality can be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the application are implemented in whole or in part using software, in one embodiment, these software elements can be implemented to operate with a computing or processing module capable of carrying out the functionality described with respect thereto. One such example computing module is shown in FIG. 31. Various embodiments are described in terms of example computing module 3100. After reading this description, it will become apparent to a person skilled in the relevant art how to implement the application using other computing modules or architectures.

Returning to FIG. 31, computing module 3100 can represent, for example, computing or processing capabilities found within mainframes, supercomputers, workstations or servers; desktop, laptop, notebook, or tablet computers; hand-held computing devices (tablets, PDA's, smartphones, cell phones, palmtops, etc.); other display devices, application-specific devices, or other electronic devices, and the like, depending on the application and/or environment for which computing module 3100 is specifically purposed.

Computing module 3100 can include, for example, one or more processors, microprocessors, controllers, control modules, or other processing devices, such as a processor 3110, and such as can be included in circuitry 3105. Processor 3110 can be implemented using a special-purpose processing engine such as, for example, a microprocessor, controller, or other control logic. In the illustrated example, processor 3110 is connected to bus 3155 by way of circuitry 3105, although any communication medium can be used to facilitate interaction with other components of computing module 3100 or to communicate externally.

Computing module 3100 can also include one or more memory modules, simply referred to herein as main memory 3115. For example, random access memory (RAM) or other dynamic memory can be used for storing information and instructions to be executed by processor 3110 or circuitry 3105. Main memory 3115 can also be used for storing temporary variables or other intermediate information during execution of instructions to be executed by processor 3110 or circuitry 3105. Computing module 3100 can likewise include a read only memory (ROM) or other static storage device coupled to bus 3155 for storing static information and instructions for processor 3110 or circuitry 3105.

Computing module 3100 can also include one or more various forms of information storage devices 3120, which can include, for example, media drive 3130 and storage unit interface 3135. Media drive 3130 can include a drive or other mechanism to support fixed or removable storage media 3125. For example, a hard disk drive, a floppy disk drive, a magnetic tape drive, an optical disk drive, a CD or DVD drive (R or RW), or other removable or fixed media drive can be provided. Accordingly, removable storage media 3125 can include, for example, a hard disk, a floppy disk, magnetic tape, cartridge, optical disk, a CD or DVD, or other fixed or removable medium that is read by, written to or accessed by media drive 3130. As these examples illustrate, removable storage media 3125 can include a computer usable storage medium having stored therein computer software or data.

In alternative embodiments, information storage devices 3120 can include other similar instrumentalities for allowing computer programs or other instructions or data to be loaded into computing module 3100. Such instrumentalities can include, for example, fixed or removable storage unit 3140 and storage unit interface 3135. Examples of such removable storage units 3140 and storage unit interfaces 3135 can include a program cartridge and cartridge interface, a removable memory (for example, a flash memory or other removable memory module) and memory slot, a PCMCIA slot and card, and other fixed or removable storage units 3140 and storage unit interfaces 3135 that allow software and data to be transferred from removable storage unit 3140 to computing module 3100.

Computing module 3100 can also include a communications interface 3150. Communications interface 3150 can be used to allow software and data to be transferred between computing module 3100 and external devices. Examples of communications interface 3150 include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface configured to operation with the communication media described herein. Software and data transferred via communications interface 3150 can typically be carried on signals, which can be electronic, electromagnetic (which includes optical) or other signals capable of being exchanged by a given communications interface 3150. These signals can be provided to/from communications interface 3150 via channel 3145. Channel 3145 can carry signals and can be implemented using a wired or wireless communication medium. Some non-limiting examples of channel 3145 include a phone line, a cellular or other radio link, an RF link, an optical link, a network interface, a local or wide area network, and other wired or wireless communications channels.

In this document, the terms "computer program medium" and "computer usable medium" and "computer readable medium", as well as variations thereof, are used to generally refer to transitory or non-transitory media such as, for example, main memory 3115, storage unit interface 3135, removable storage media 3125, and/or channel 3145. These and other various forms of computer program media or computer usable/readable media can be involved in carrying one or more sequences of one or more instructions to a processing device for execution. Such instructions embodied on the medium, can generally be referred to as "computer program code" or a "computer program product" or "instructions" (which can be grouped in the form of computer programs or other groupings). When executed, such instructions can enable the computing module 3100, circuitry related thereto, and/or a processor thereof or connected thereto to perform features or functions of the present disclosure as discussed herein (for example, in connection with methods described above and/or in the claims), including for example when the same is/are incorporated into a system, apparatus, device and/or the like.

Various embodiments have been described with reference to specific example features thereof. It will, however, be evident that various modifications and changes can be made thereto without departing from the broader spirit and scope of the various embodiments as set forth in the appended claims. The specification and figures are, accordingly, to be regarded in an illustrative rather than a restrictive sense.

Although described above in terms of various example embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the present application, whether or not such embodiments are described and whether or not such features are presented as being a part of a described embodiment. Thus, the breadth and scope of the present application should not be limited by any of the above-described example embodiments.

Terms and phrases used in the present application, and variations thereof, unless otherwise expressly stated, should be construed as open ended as opposed to limiting. As examples of the foregoing: the term "including" should be read as meaning "including, without limitation" or the like; the term "example" is used to provide illustrative instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Similarly, the plural can in some cases be recognized as applicable to the singular and vice versa. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases can be absent. The use of the term "module" does not imply that the components or functionality described or claimed as part of the module are all configured in a common package. Indeed, any or all of the various components of a module, whether control logic, circuitry, or other components, can be combined in a single package or separately maintained and can further be distributed in multiple groupings or packages or across multiple locations.

Additionally, the various embodiments set forth herein are described in terms of example block diagrams, flow charts, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration. Moreover, the operations and sub-operations of various methods described herein are not necessarily limited to the order described or shown in the figures, and one of skill in the art will appreciate, upon studying the present disclosure, variations of the order of the operations described herein that are within the spirit and scope of the disclosure.

In addition, the operations and sub-operations of methods described herein can be carried out or implemented, in some cases, by one or more of the components, elements, devices, modules, circuitry, processors, etc. of systems, apparatuses, devices, environments, and/or computing modules described herein and referenced in various of FIGS. of the present disclosure, as well as one or more sub-components, elements, devices, modules, processors, circuitry, and the like depicted therein and/or described with respect thereto. In such instances, the description of the methods or aspects thereof can refer to a corresponding component, element, etc., but regardless of whether an explicit reference is made, one of skill in the art will recognize upon studying the present disclosure when the corresponding component, element, etc. can be used. Further, it will be appreciated that such references do not necessarily limit the described methods to the particular component, element, etc. referred to. Thus, it will be appreciated by one of skill in the art that aspects and features described above in connection with (sub-) components, elements, devices, modules, and circuitry, etc., including variations thereof, can be applied to the various operations described in connection with methods described herein, and vice versa, without departing from the scope of the present disclosure.

What is claimed is:

1. A method for wireless communication of continuous analyte concentration data, the method comprising:
    transmitting one or more first advertising messages utilizing a first set of parameters during a predetermined communication interval;
    transmitting one or more second advertising messages utilizing a second set of parameters during the predetermined communication interval;
    establishing a first communication session between an analyte sensor system and a first device and a second communication session between the analyte sensor system and a second device during the predetermined communication interval based on at least one of the first advertising messages and the second advertising messages; and
    transmitting, during the predetermined communication interval, analyte concentration data directly to: (i) the first device utilizing at least one of the first communication session and the second communication session, and (ii) the second device utilizing the second communication session, wherein the first communication session and the second communication session are maintained concurrently, and the first device is agnostic of the first communication session and the second communication session for receiving the analyte concentration data.

2. The method of claim 1, wherein:
    the one or more first advertising messages advertise availability of the analyte sensor system for connection with one or more devices not currently listed on a whitelist of one or more previously authenticated devices; and
    the one or more second advertising messages advertise availability of the analyte sensor system for connection with one or more devices currently listed on the whitelist.

3. The method of claim 1, wherein the one or more first advertising messages are transmitted after the one or more second advertising messages.

4. The method of claim 1, wherein the one or more first advertising messages are transmitted before the one or more second advertising messages.

5. The method of claim 1, further comprising not transmitting the one or more first advertising messages during the predetermined communication interval if a whitelist of previously authenticated devices is full.

6. The method of claim 1, further comprising not transmitting the one or more second advertising messages during the predetermined communication interval if a whitelist of previously authenticated devices is empty.

7. The method of claim 1, further comprising not transmitting the one or more second advertising messages during the predetermined communication interval if all devices currently listed on a whitelist of previously authenticated devices connect to the analyte sensor system responsive to the one or more first advertising messages.

8. The method of claim 1, wherein the first set of parameters define one or more of:
    a first duration of a first advertising interval for transmitting the one or more first advertising messages;
    a first periodic interval for transmission of the one or more first advertising messages; and
    a first power for transmission of the one or more first advertising messages.

9. The method of claim 8, wherein the second set of parameters define one or more of:
    a second duration of a second advertising interval for transmitting the one or more second advertising messages;
    a second periodic interval for transmission of the one or more second advertising messages; and
    a second power for transmission of the one or more second advertising messages.

10. The method of claim 9, wherein the first power for transmission of the one or more first advertising messages is lower than the second power for transmission of the one or more second advertising messages.

11. The method of claim 1, wherein devices utilized by consumers and devices utilized by medical professionals are both eligible for inclusion in a whitelist of previously authenticated devices.

12. The method of claim 1, wherein transmitting at least one of the one or more first advertising messages or the one or more second advertising messages is based on a whitelist of devices previously authenticated for connection to the analyte sensor system, the whitelist comprising a plurality of at least three entries.

13. An analyte sensor system configured for wireless communication of analyte concentration data, comprising:
a transceiver radio configured to:
transmit one or more first advertising messages utilizing a first set of parameters during a predetermined communication interval; and
transmit one or more second advertising messages utilizing a second set of parameters during the predetermined communication interval;
one or more processors configured to:
establish a first communication session between the analyte sensor system and a first device and a second communication session between the analyte sensor system and a second device based on at least one of the first advertising messages and the second advertising messages; and
causing the transceiver radio to transmit, during the predetermined communication interval, analyte concentration data directly to (i) the first device utilizing at least one of the first communication session and the second communication session, and (ii) the second device utilizing the second communication session, wherein the first communication session and the second communication session are maintained concurrently, and the first device is agnostic of the first communication session and the second communication session for receiving the analyte concentration data.

14. The analyte sensor system of claim 13, wherein the one or more processors are configured to cause the transceiver radio to not transmit the one or more first advertising messages during the predetermined communication interval if a whitelist of one or more previously authenticated devices is full.

15. The analyte sensor system of claim 13, wherein the one or more processors are configured to cause the transceiver radio to not transmit the one or more second advertising messages during the predetermined communication interval if a whitelist of previously authenticated devices is empty.

16. The analyte sensor system of claim 13, wherein the one or more processors are configured to cause the transceiver radio to not transmit the one or more second advertising messages during the predetermined communication interval if all devices currently listed on a whitelist of previously authenticated devices connect to the analyte sensor system responsive to the one or more first advertising messages.

* * * * *